US008399483B2

(12) United States Patent
Allen et al.

(10) Patent No.: US 8,399,483 B2
(45) Date of Patent: Mar. 19, 2013

(54) QUINOXALINE AND QUINOLINE DERIVATIVES AS KINASE INHIBITORS

(75) Inventors: Daniel Rees Allen, Saffron Walden (GB); George Martin Buckley, Slough (GB); Roland Bürli, Saffron Walden (GB); John Richard Davenport, Slough (GB); Natasha Kinsella, Slough (GB); Christopher James Lock, Slough (GB); Christopher Lowe, Slough (GB); Stephen Robert Mack, Slough (GB); William Ross Pitt, Slough (GB); Andrew James Ratcliffe, Slough (GB); Marianna Dilani Richard, Slough (GB); Verity Margaret Sabin, Slough (GB); Andrew Sharpe, Saffron Walden (GB); Laura Jane Tait, Slough (GB); Graham John Warrellow, Slough (GB); Sophie Caroline Williams, Slough (GB)

(73) Assignee: UCB Pharma S.A., Brussels (BE)

( * ) Notice: Subject to any disclaimer, the term of this patent is extended or adjusted under 35 U.S.C. 154(b) by 100 days.

(21) Appl. No.: 12/809,394

(22) PCT Filed: Dec. 17, 2008

(86) PCT No.: PCT/GB2008/004171
§ 371 (c)(1),
(2), (4) Date: Dec. 13, 2010

(87) PCT Pub. No.: WO2009/081105
PCT Pub. Date: Jul. 2, 2009

(65) Prior Publication Data
US 2011/0105508 A1 May 5, 2011

(30) Foreign Application Priority Data

Dec. 21, 2007 (GB) .................................. 0725030.1
Aug. 19, 2008 (GB) .................................. 0815177.1

(51) Int. Cl.
*A61K 31/47* (2006.01)
(52) U.S. Cl. ...................................... 514/311; 546/152
(58) Field of Classification Search .................. 514/311; 546/152
See application file for complete search history.

(56) References Cited

FOREIGN PATENT DOCUMENTS

| DE | 258 228 A1 | 7/1988 |
|---|---|---|
| WO | WO 2007/030360 A | 3/2007 |
| WO | WO 2007/079999 A | 7/2007 |
| WO | WO 2007/088999 A | 8/2007 |
| WO | WO 2007/129052 A | 11/2007 |
| WO | WO 2008/118455 A | 10/2008 |
| WO | WO 2008/118468 A | 10/2008 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Pullman, et al. Theoret. Chim. Acta (Berl.), 15, 1969, 265-268.*
Vekariya N.A. et al.: "Synthesis of isoxazoles and quinoalines as potential anticancer agents," Indian Journal of Chemistry, Section B: Organic and Medicinal Chemistry, Scientific Publishers, Jodhpur, IN, vol. 42B, No. 2, Feb. 1, 2003, pp. 421-421.
Starke I. et al.: "Evidence for an aryl migration during the electron impact induced fragmentation of substituted aryloxymethylquinoxalines," Rapid Communications in Mass Spectrometry: RCM 2002, vol. 16, No. 3, 2002, pp. 169-175.

* cited by examiner

*Primary Examiner* — Douglas M Willis
(74) *Attorney, Agent, or Firm* — McDonnell Boehnen Hulbert & Berghoff LLP

(57) ABSTRACT

A series of heteroaryl-substituted quinoxaline and quinoline derivatives, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions, said substituted derivatives having the general formula

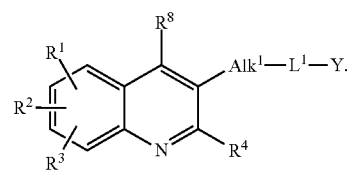

(IA)

12 Claims, No Drawings

QUINOXALINE AND QUINOLINE DERIVATIVES AS KINASE INHIBITORS

This application is a US national phase of International Application No. PCT/GB2008/004171 filed on Dec. 17, 2008, the disclosure of which is incorporated herein by reference in its entirety.

The present invention relates to the use of a class of quinoxaline and quinoline derivatives in therapy. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds of use in the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human PI3K enzymes.

German Patent Application No. DD 258228 describes the preparation of 2-(heterocyclyloxymethyl)quinoxalines, including 2-phenyl-3-[(8-quinolinyloxy)-methyl]quinoxaline, as intermediates for biologically active compounds.

The specific compound 2,2'-(1,2-ethanediyl)bis[3-phenyl]quinoxaline is disclosed in the integrated spectral database system of organic compounds from the National Institute of Advanced Industrial Science and Technology in Japan; but no therapeutic utility is ascribed to this compound.

The *Indian Journal of Chemistry, Section B: Organic Chemistry including Medicinal Chemistry*, 2003, 42B(2), 421-424, (Vekariya, N. A. et al.) discloses a class of substituted 2-(benzimidazol-2-ylmethyl)phenylquinoxaline derivatives, including 2-(1H-benzimidazol-2-ylmethyl)-3-phenylquinoxaline, 2-(1H-benzimidazol-2-ylmethyl)-3-(3-bromophenyl)quinoxaline, 2-(1H-benzimidazol-2-ylmethyl)-3-(2-chlorophenyl)-quinoxaline, 2-(1H-benzimidazol-2-ylmethyl)-3-(3-chlorophenyl)quinoxaline, 2-(1H-benzimidazol-2-ylmethyl)-3-[4-(N,N-dimethylamino)phenyl]quinoxaline, 2-(1H-benzimidazol-2-ylmethyl)-3-(2-hydroxyphenyl)quinoxaline, 2-(1H-benzimidazol-2-ylmethyl)-3-(2-methoxyphenyl)quinoxaline, 2-(1H-benzimidazol-2-ylmethyl)-3-(4-methoxyphenyl)quinoxaline, 2-(1H-benzimidazol-2-ylmethyl)-3-(4-methylphenyl)-quinoxaline, 2-(1H-benzimidazol-2-ylmethyl)-3-[4-(methylthio)phenyl]quinoxaline and 2-(1H-benzimidazol-2-ylmethyl)-3-(2-furanyl)quinoxaline, as anticancer agents.

WO 2008/118454, WO 2008/118455 and WO 2008/118468, all published on 2 Oct. 2008, describe various series of quinoline and quinoxaline derivatives that are structurally related to each other and are stated to be useful to inhibit the biological activity of human PI3Kδ and to be of use in treating PI3K-mediated conditions or disorders.

The compounds of use in the present invention are potent and selective PI3K inhibitors having a binding affinity (IC$_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower IC$_{50}$ figure denotes a more active compound). The compounds of use in the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides the use of a compound of formula (I) or an N-oxide thereof, or a pharmaceutically acceptable salt or solvate thereof:

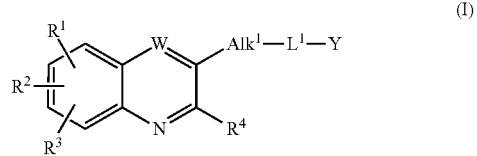

(I)

wherein

W represents CR$^8$ or N;

Alk$^1$ represents a straight or branched C$_{1-3}$ alkylene chain;

L$^1$ represents oxygen, sulfur, NR$^9$ or a covalent bond;

Y represents an optionally substituted mono- or bicyclic heteroaryl group containing at least one nitrogen atom;

R$^1$, R$^2$ and R$^3$ independently represent hydrogen, halogen, cyano, nitro, C$_{1-6}$ alkyl, trifluoromethyl, aryl(C$_{1-6}$)alkyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkyl-amino, C$_{2-6}$ alkylcarbonylamino, C$_{2-6}$ alkoxycarbonylamino, C$_{1-6}$ alkylsulfonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl or di(C$_{1-6}$)alkylaminosulfonyl; and $R^4$ represents a group of formula (a):

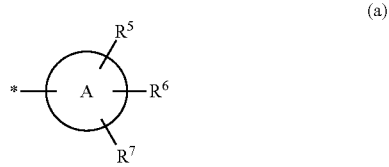

(a)

in which *―― represents the bond attaching the ring A to the rest of the molecule;

A represents a monocyclic aryl or heteroaryl group;

$R^5$, $R^6$ and $R^7$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylamino-sulfonyl, $C_{3-7}$ cycloalkyl or $C_{3-6}$ heterocycloalkyl, or optionally substituted monocyclic aryl or heteroaryl;

$R^8$ represents hydrogen, halogen, $C_{1-6}$ alkyl or $C_{1-6}$ alkoxy; and $R^9$ represents hydrogen or $C_{1-6}$ alkyl;

for the manufacture of a medicament for the treatment and/or prevention of disorders for which the administration of a selective PI3K inhibitor is indicated.

The present invention also provides a method for the treatment and/or prevention of disorders for which the administration of a selective PI3K inhibitor is indicated which comprises administering to a patient in need of such treatment an effective amount of a compound of formula (I) as depicted above or an N-oxide thereof, or a pharmaceutically acceptable salt or solvate thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope the use of solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

For the compounds as represented by formula (I) and the more detailed description hereinafter certain of the general terms used in relation to substituents are to be understood to include the following atoms or groups unless specified otherwise.

The term "$C_{1-6}$ alkyl" as used herein refers to straight or branched alkyl groups containing from 1 to 6 carbon atoms. Suitable groups include $C_{1-3}$ alkyl groups, such as methyl, ethyl, propyl or isopropyl.

The expression "$C_{1-3}$ alkylene chain" refers to a divalent straight or branched alkylene chain containing 1 to 3 carbon atoms. Typical examples include methylene, ethylene, methylmethylene, ethylmethylene and dimethylmethylene.

The term "$C_{1-6}$ alkoxy" as used herein is intended to include straight or branched —O($C_{1-6}$ alkyl) groups, for example methoxy, ethoxy, n-propoxy or isopropoxy. Typical examples include methoxy and isopropoxy.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-6}$ heterocycloalkyl" refers to a four- to seven-membered saturated cyclic group containing 3 to 6 carbon atoms and at least one heteroatom, typically one or two heteroatoms, preferably selected from oxygen, nitrogen and sulfur. The nitrogen heteroatom may optionally be substituted with a $C_{1-6}$ alkyl group, typically methyl. It will be appreciated that the $C_{3-6}$ heterocycloalkyl group may be linked through any available carbon or nitrogen atom. Suitable examples include azetidinyl, tetrahydrofuranyl, pyrrolidinyl, imidazolidinyl, tetrahydropyranyl, piperidinyl, piperazinyl, morpholinyl and thiomorpholinyl.

The expression "monocyclic aryl group" is intended to include monocyclic ring $C_6$ aromatic groups, such as phenyl.

The expression "monocyclic heteroaryl group" includes for example five- or six-membered aromatic groups containing one, two, three or four heteroatoms selected from oxygen, sulfur and nitrogen atoms. Suitable examples of heteroaryl groups of this type include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl.

The expression "mono- or bicyclic heteroaryl group containing at least one nitrogen atom" in relation to the group Y refers in particular to a mono- or bicyclic aromatic ring system containing one, two, three or four heteroatoms selected from oxygen, sulfur and nitrogen atoms, with at least one of the heteroatoms being nitrogen. The ring Y may be linked to the group $L^1$ through any available carbon or nitrogen atom. Suitable examples include pyrrolyl, pyridinyl, indolyl, quinolinyl, isoquinolinyl, imidazolyl, pyrazolyl, triazolyl, pyridazinyl, pyrimidinyl, pyrazinyl, triazinyl, indazolyl, benzimidazolyl, furopyridinyl, benzoxazolyl, benzothiazolyl, cinnolinyl, phthalazinyl, quinazolinyl, quinoxalinyl, imidazopyridinyl, pyrazolopyridinyl, purinyl, pyrazolo-pyrimidinyl, pyrrolopyrimidinyl, triazolopyrimidinyl, naphthyridinyl and pteridinyl. A further example is pyridopyrimidinyl.

The term "halogen" as used herein is intended to include fluorine, chlorine, bromine and iodine atoms, typically fluorine, chlorine or bromine.

The term "amino" represents a group of formula —NH$_2$. The terms "C$_{1-6}$ alkylamino" and "di(C$_{1-6}$)alkylamino" represent the groups —N(H)(C$_{1-6}$ alkyl) and —N(C$_{1-6}$ alkyl)$_2$ respectively, in which it will be appreciated that the C$_{1-6}$ alkyl groups may be the same or different.

The terms "C$_{1-6}$ alkylthio", "C$_{1-6}$ alkylsulfinyl" and "C$_{1-6}$ alkylsulfonyl" respectively represent the groups —S(C$_{1-6}$ alkyl), —SO(C$_{1-6}$ alkyl) and —SO$_2$(C$_{1-6}$ alkyl).

The terms "C$_{2-6}$ alkylcarbonylamino" and "C$_{1-6}$ alkylsulfonylamino" respectively represent the groups —NHC(O)(C$_{1-5}$ alkyl) and —NHS(O)$_2$(C$_{1-6}$ alkyl).

The terms "C$_{2-6}$ alkylcarbonyl" and "C$_{2-6}$ alkoxycarbonyl" respectively represent the groups —C(O)(C$_{1-5}$ alkyl) and —C(O)O(C$_{1-5}$ alkyl).

The terms "aminocarbonyl", "C$_{1-6}$ alkylaminocarbonyl" and "di(C$_{1-6}$)alkyl-aminocarbonyl" respectively represent the groups —CONH$_2$, —CON(H)(C$_{1-6}$ alkyl) and —CON(C$_{1-6}$ alkyl)$_2$, in which it will be appreciated that the C$_{1-6}$ alkyl groups may be the same or different.

The terms "aminosulfonyl", "C$_{1-6}$ alkylaminosulfonyl" and "di(C$_{1-6}$)alkyl-aminosulfonyl" respectively represent the groups —SO$_2$NH$_2$, —SO$_2$N(H)(C$_{1-6}$ alkyl) and —SO$_2$N(C$_{1-6}$ alkyl)$_2$, in which it will be appreciated that the C$_{1-6}$ alkyl groups may be the same or different.

The terms "C$_{3-6}$ cycloalkylcarbonyl" and "C$_{3-6}$ heterocycloalkylcarbonyl" represent the groups —C(O)(C$_{3-6}$ cycloalkyl) and —C(O)(C$_{3-6}$ heterocycloalkyl) respectively, in which the heterocycloalkyl group may be linked to the carbonyl group through any available carbon or nitrogen atom.

The term "cyano" represents a —CN group.

The term "formyl" represents a —CHO group.

The term "carboxy" represents a —COOH group.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C═O) ↔ enol (CH═COH) tautomers or amide (NHC═O) ↔ hydroxyimine (N═COH) tautomers. Formula (I) and the formulae depicted hereinafter are intended to represent all individual tautomers and all possible mixtures thereof, unless stated or shown otherwise.

Specific sub-classes of compounds of use in the present invention are represented by the compounds of formula (IA) and (IB):

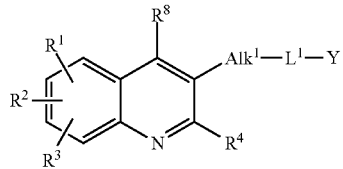

(IA)

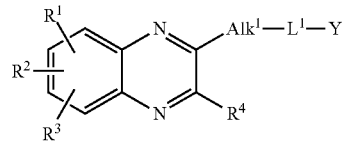

(IB)

wherein Alk$^1$, L$^1$, Y, R$^1$, R$^2$, R$^3$, R$^4$ and R$^8$ are as defined above.

Certain compounds falling within the definition of formula (I) above are novel. Accordingly, in one aspect, the present invention provides a compound of formula (IA) as depicted above or an N-oxide thereof, or a pharmaceutically acceptable salt or solvate thereof, wherein Alk$^1$, L$^1$, Y, R$^1$, R$^2$, R$^3$, R$^4$ and R$^8$ are as defined above; provided that Y does not represent an optionally substituted heteroaryl group selected from the following:

pyridin-4-yl, when Alk$^1$ represents —CH$_2$—, —CH(CH$_3$)—, —CH(CH$_2$CH$_3$)— or —C(CH$_3$)$_2$—;

pyrimidin-4-yl, when Alk$^1$ represents —CH$_2$—, —CH(CH$_3$)—, —CH(CH$_2$CH$_3$)— or —C(CH$_3$)$_2$—;

imidazo[4,5-b]pyridin-7-yl, when Alk$^1$ represents —CH$_2$—, —CH(CH$_3$)—, —CH(CH$_2$CH$_3$)— or —C(CH$_3$)$_2$—;

imidazo[4,5-c]pyridin-1-yl, when Alk$^1$ represents —CH$_2$—, —CH(CH$_3$)—, —CH(CH$_2$CH$_3$)— or —C(CH$_3$)$_2$— and L$^1$ represents a covalent bond;

pyrazolo[4,3-c]pyridin-1-yl, when Alk$^1$ represents —CH$_2$—, —CH(CH$_3$)—, —CH(CH$_2$CH$_3$)— or —C(CH$_3$)$_2$— and L$^1$ represents a covalent bond;

pyrrolo[2,3-b]pyridin-4-yl, when Alk$^1$ represents —CH$_2$—, —CH(CH$_3$)—, —CH(CH$_2$CH$_3$)— or —C(CH$_3$)$_2$—;

pyrrolo[3,2-c]pyridin-1-yl, when Alk$^1$ represents —CH$_2$—, —CH(CH$_3$)—, —CH(CH$_2$CH$_3$)— or —C(CH$_3$)$_2$— and L$^1$ represents a covalent bond;

9H-purin-6-yl, when Alk$^1$ represents —CH$_2$—, —CH(CH$_3$)—, —CH(CH$_2$CH$_3$)— or —C(CH$_3$)$_2$—;

purin-9-yl, when Alk$^1$ represents —CH$_2$—, —CH(CH$_3$)—, —CH(CH$_2$CH$_3$)— or —C(CH$_3$)$_2$— and L$^1$ represents a covalent bond;

pyrazolo[3,4-d]pyrimidin-1-yl, when Alk$^1$ represents —CH$_2$—, —CH(CH$_3$)—, —CH(CH$_2$CH$_3$)— or —C(CH$_3$)$_2$— and L$^1$ represents a covalent bond;

pyrrolo[2,3-d]pyrimidin-1-yl, when Alk$^1$ represents —CH$_2$—, —CH(CH$_3$)—, —CH(CH$_2$CH$_3$)— or —C(CH$_3$)$_2$— and L$^1$ represents a covalent bond;

pyrrolo[2,3-d]pyrimidin-4-yl, when Alk$^1$ represents —CH$_2$—, —CH(CH$_3$)—, —CH(CH$_2$CH$_3$)— or —C(CH$_3$)$_2$—;

pyrido[3,2-c]pyridin-1-yl, when Alk$^1$ represents —CH$_2$—, —CH(CH$_3$)—, —CH(CH$_2$CH$_3$)— or —C(CH$_3$)$_2$— and L$^1$ represents a covalent bond; and pyrido[2,3-d]pyrimidin-1-yl, when Alk$^1$ represents —CH$_2$—, —CH(CH$_3$)—, —CH(CH$_2$CH$_3$)— or —C(CH$_3$)$_2$— and L$^1$ represents a covalent bond.

In another aspect, the present invention provides a compound of formula (I) as depicted above or an N-oxide thereof, or a pharmaceutically acceptable salt or solvate thereof, wherein Y represents pyrrolyl, pyridinyl [except pyridin-4-yl, when Alk$^1$ represents —CH$_2$—, —CH(CH$_3$)—, —CH(CH$_2$CH$_3$)— or —C(CH$_3$)$_2$—], indolyl, isoquinolinyl, imidazolyl, pyrazolyl, triazolyl, pyridazinyl, pyrimidinyl [except pyrimidin-4-yl, when Alk$^1$ represents —CH$_2$—, —CH(CH$_3$)—, —CH(CH$_2$CH$_3$)— or —C(CH$_3$)$_2$—], pyrazinyl, triazinyl, indazolyl, furopyridinyl, benzoxazoyl, benzothiazolyl, cinnolinyl, phthalazinyl, quinazolinyl, imidazopyridinyl [except (i) imidazo[4,5-b]pyridin-7-yl, when $Alk^1$ represents —$CH_2$—, —$CH(CH_3)$—, —$CH(CH_2CH_3)$— or —$C(CH_3)_2$—; and (ii) imidazo[4,5-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond], pyrazolopyridinyl [except pyrazolo[4,3-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond], purinyl [except (i) 9H-purin-6-yl, when $Alk^1$ represents —$CH_2$—, —$CH(CH_3)$—, —$CH(CH_2CH_3)$— or —$C(CH_3)_2$—; and (ii) purin-9-yl, when $Alk^1$ represents —$CH_2$—, —$CH(CH_3)$—, —$CH(CH_2CH_3)$— or —$C(CH_3)_2$— and $L^1$ represents a covalent bond], pyrazolopyrimidinyl [except pyrazolo[3,4-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond], pyrrolo-pyrimidinyl [except (i) pyrrolo[2,3-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond; and (ii) pyrrolo[2,3-d]pyrimidin-4-yl, when $Alk^1$ represents —$CH_2$—, —$CH(CH_3)$—, —$CH(CH_2CH_3)$— or —$C(CH_3)_2$—], triazolopyrimidinyl, naphthyridinyl, pteridinyl or pyridopyrimidinyl [except pyrido[2,3-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond], any of which groups may be optionally substituted by one or more substituents; and $W, Alk^1, L^1, R^1, R^2, R^3$ and $R^4$ are as defined above.

In another aspect, the present invention provides a compound of formula (I) as depicted above or an N-oxide thereof, or a pharmaceutically acceptable salt or solvate thereof, wherein Y represents pyrrolyl, pyridinyl [except pyridin-4-yl, when $Alk^1$ represents —$CH_2$—, —$CH(CH_3)$—, —$CH(CH_2CH_3)$— or —$C(CH_3)_2$—], indolyl, isoquinolinyl, imidazolyl, pyrazolyl, triazolyl, pyridazinyl, pyrimidinyl [except pyrimidin-4-yl, when $Alk^1$ represents —$CH_2$—, —$CH(CH_3)$—, —$CH(CH_2CH_3)$— or —$C(CH_3)_2$—], pyrazinyl, triazinyl, indazolyl, furopyridinyl, benzoxazoyl, benzothiazolyl, cinnolinyl, phthalazinyl, quinazolinyl, imidazopyridinyl [except (i) imidazo[4,5-b]pyridin-7-yl, when $Alk^1$ represents —$CH_2$—, —$CH(CH_3)$—, —$CH(CH_2CH_3)$— or —$C(CH_3)_2$—; and (ii) imidazo[4,5-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond], pyrazolopyridinyl [except pyrazolo[4,3-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond], purinyl [except (i) 9H-purin-6-yl, when $Alk^1$ represents —$CH_2$—, —$CH(CH_3)$—, —$CH(CH_2CH_3)$— or —$C(CH_3)_2$—; and (ii) purin-9-yl, when $Alk^1$ represents —$CH_2$—, —$CH(CH_3)$—, —$CH(CH_2CH_3)$— or —$C(CH_3)_2$— and $L^1$ represents a covalent bond], pyrazolopyrimidinyl [except pyrazolo[3,4-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond], pyrrolo-pyrimidinyl [except (i) pyrrolo[2,3-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond; and (ii) pyrrolo[2,3-d]pyrimidin-4-yl, when $Alk^1$ represents —$CH_2$—, —$CH(CH_3)$—, —$CH(CH_2CH_3)$— or —$C(CH_3)_2$—], triazolopyrimidinyl, naphthyridinyl or pteridinyl, any of which groups may be optionally substituted by one or more substituents; and $W, Alk^1, L^1, R^1, R^2, R^3$ and $R^4$ are as defined above.

In another aspect, the present invention provides a compound of formula (I) as depicted above or an N-oxide thereof, or a pharmaceutically acceptable salt or solvate thereof, wherein Y represents pyrrolyl, pyridin-2-yl, pyridin-3-yl, indolyl, isoquinolinyl, imidazolyl, pyrazolyl, triazolyl, pyridazinyl, pyrimidin-2-yl, pyrimidin-5-yl, pyrazinyl, triazinyl, indazolyl, furopyridinyl, benzoxazoyl, benzothiazolyl, cinnolinyl, phthalazinyl, quinazolinyl, purin-1-yl, purin-2-yl, purin-3-yl, 7H-purin-6-yl, purin-7-yl, purin-8-yl, pyrazolo[3,4-d]pyrimidin-4-yl, triazolopyrimidinyl, naphthyridinyl, pteridinyl, pyrido[2,3-d]pyrimidin-4-yl or pyrido[3,4-d]pyrimidin-4-yl, any of which groups may be optionally substituted by one or more substituents; and $W, Alk^1, L^1, R^1, R^2, R^3$ and $R^4$ are as defined above.

In another aspect, the present invention provides a compound of formula (I) as depicted above or an N-oxide thereof, or a pharmaceutically acceptable salt or solvate thereof, wherein Y represents pyrrolyl, pyridin-2-yl, indolyl, isoquinolinyl, imidazolyl, pyrazolyl, triazolyl, pyridazinyl, pyrimidin-2-yl, pyrimidin-5-yl, pyrazinyl, triazinyl, indazolyl, furopyridinyl, benzoxazoyl, benzothiazolyl, cinnolinyl, phthalazinyl, quinazolinyl, purin-1-yl, purin-2-yl, purin-3-yl, 7H-purin-6-yl, purin-7-yl, purin-8-yl, pyrazolo[3,4-d]pyrimidin-4-yl, triazolopyrimidinyl, naphthyridinyl or pteridinyl, any of which groups may be optionally substituted by one or more substituents; and $W, Alk^1, L^1, R^1, R^2, R^3$ and $R^4$ are as defined above.

In a further aspect, the present invention provides a compound of formula (I) as depicted above or an N-oxide thereof, or a pharmaceutically acceptable salt or solvate thereof, wherein $W, Alk^1, Y, R^1, R^2, R^3$ and $R^4$ are as defined above; provided that Y does not represent an optionally substituted heteroaryl group selected from the following:

pyridin-4-yl, when $Alk^1$ represents —$CH_2$—, —$CH(CH_3)$—, —$CH(CH_2CH_3)$— or —$C(CH_3)_2$—;

pyrimidin-4-yl, when $Alk^1$ represents —$CH_2$—, —$CH(CH_3)$—, —$CH(CH_2CH_3)$— or —$C(CH_3)_2$—;

imidazo[4,5-b]pyridin-7-yl, when $Alk^1$ represents —$CH_2$—, —$CH(CH_3)$—, —$CH(CH_2CH_3)$— or —$C(CH_3)_2$—;

imidazo[4,5-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond;

pyrazolo[4,3-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond;

pyrrolo[2,3-b]pyridin-4-yl, when $Alk^1$ represents —$CH_2$—, —$CH(CH_3)$—, —$CH(CH_2CH_3)$— or —$C(CH_3)_2$—;

pyrrolo[3,2-c]pyridin-1-yl, when $Alk^1$ represents —$CH_2$—, —$CH(CH_3)$—, —$CH(CH_2CH_3)$— or —$C(CH_3)_2$— and $L^1$ represents a covalent bond;

9H-purin-6-yl, when $Alk^1$ represents —$CH_2$—, —$CH(CH_3)$—, —$CH(CH_2CH_3)$— or —$C(CH_3)_2$—;

purin-9-yl, when $Alk^1$ represents —$CH_2$—, —$CH(CH_3)$—, —$CH(CH_2CH_3)$— or —$C(CH_3)_2$— and $L^1$ represents a covalent bond;

pyrazolo[3,4-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond;

pyrrolo[2,3-d]pyrimidin-1-yl, when $Alk^1$ represents —$CH_2$—, —$CH(CH_3)$—, —$CH(CH_2CH_3)$— or —$C(CH_3)_2$— and $L^1$ represents a covalent bond;

pyrrolo[2,3-d]pyrimidin-4-yl, when $Alk^1$ represents —$CH_2$—, —$CH(CH_3)$—, —$CH(CH_2CH_3)$— or —$C(CH_3)_2$—;

pyrido[3,2-c]pyridin-1-yl, when Alk$^1$ represents —CH$_2$—, —CH(CH$_3$)—, —CH(CH$_2$CH$_3$)— or —C(CH$_3$)$_2$— and L$^1$ represents a covalent bond; and pyrido[2,3-d]pyrimidin-1-yl, when Alk$^1$ represents —CH$_2$—, —CH(CH$_3$)—, —CH(CH$_2$CH$_3$)— or —C(CH$_3$)$_2$— and L$^1$ represents a covalent bond; provided also that, when W represents N, then -Alk$^1$-L$^1$-Y is other than quinolin-8-yloxymethyl, 2-(3-phenyl-quinoxalin-2-yl)ethyl or benzimidazol-2-ylmethyl.

A particular sub-class in accordance with the present invention is represented by the group (IA).

In one embodiment, W represents CR$^8$. In another embodiment, W represents N.

Suitable values of Alk$^1$ include —CH$_2$— (methylene), —CH(CH$_3$)— (methylmethylene) and —CH(CH$_2$CH$_3$)— (ethylmethylene).

In one embodiment, Alk$^1$ represents —CH$_2$— (methylene). In another embodiment, Alk$^1$ represents —CH(CH$_3$)— (methylmethylene). In a further embodiment, Alk$^1$ represents —CH(CH$_2$CH$_3$)— (ethylmethylene).

Alk$^1$ typically represents methylene.

L$^1$ suitably represents oxygen, sulfur or a covalent bond. In one embodiment, L$^1$ represents oxygen. In another embodiment, L$^1$ represents sulfur. In a further embodiment, L$^1$ represents a covalent bond. In a still further embodiment, L$^1$ represents NR$^9$.

In one embodiment, Y represents optionally substituted pyridinyl or an optionally substituted mono- or bicyclic ring system containing at least two nitrogen atoms.

In one embodiment, Y represents optionally substituted pyridin-2-yl. In another embodiment, Y represents optionally substituted pyridin-3-yl. In a further embodiment, Y represents optionally substituted pyridin-4-yl.

In one embodiment, Y represents an optionally substituted mono- or bicyclic ring system containing at least two nitrogen atoms.

Generally, Y may represent pyrrolyl, pyridinyl, indolyl, quinolinyl, isoquinolinyl, imidazolyl, pyrazolyl, triazolyl, pyridazinyl, pyrimidinyl, pyrazinyl, triazinyl, indazolyl, benzimidazolyl, furopyridinyl, benzoxazolyl, benzothiazolyl, cinnolinyl, phthalazinyl, quinazolinyl, quinoxalinyl, imidazopyridinyl, pyrazolopyridinyl, purinyl, pyrazolo-pyrimidinyl, pyrrolopyrimidinyl, triazolopyrimidinyl, naphthyridinyl, pteridinyl or pyridopyrimidinyl, any of which groups may be optionally substituted by one or more substituents.

More particularly, Y may represent pyrrolyl, pyridin-2-yl, pyridin-3-yl, indolyl, isoquinolinyl, imidazolyl, pyrazolyl, triazolyl, pyridazinyl, pyrimidin-5-yl, pyrazinyl, triazinyl, indazolyl, furopyridinyl, benzoxazolyl, benzothiazolyl, cinnolinyl, phthalazinyl, quinazolinyl, purin-1-yl, purin-2-yl, purin-3-yl, 7H-purin-6-yl, purin-7-yl, purin-8-yl, pyrazolo[3,4-c]pyrimidin-4-yl, triazolopyrimidinyl, naphthyridinyl, pteridinyl or pyridopyrimidin-4-yl, any of which groups may be optionally substituted by one or more substituents.

Representative values of Y include isoquinolinyl, pyrimidinyl, triazinyl, quinoxalinyl, purinyl, pyrazolopyrimidinyl and pyridopyrimidinyl, any of which groups may be optionally substituted by one or more substituents.

Illustrative values of Y include isoquinolinyl, pyrimidinyl, triazinyl, quinoxalinyl, purinyl and pyridopyrimidinyl, any of which groups may be optionally substituted by one or more substituents.

Definitive values of Y include isoquinolinyl, pyrimidin-2-yl, triazinyl, quinoxalinyl, purin-3-yl, 7H-purin-6-yl, purin-7-yl, pyrazolo[3,4-d]pyrimidin-4-yl, pyrido[2,3-d]pyrimidin-4-yl and pyrido[3,4-d]pyrimidin-4-yl, any of which groups may be optionally substituted by one or more substituents.

Selected values of Y include isoquinolinyl, pyrimidin-2-yl, triazinyl, quinoxalinyl, purin-3-yl, 7H-purin-6-yl, purin-7-yl, pyrido[2,3-d]pyrimidin-4-yl and pyrido[3,4-d]pyrimidin-4-yl, any of which groups may be optionally substituted by one or more substituents.

In one embodiment, Y represents optionally substituted isoquinolinyl.

In another embodiment, Y represents optionally substituted pyrimidin-2-yl.

In another embodiment, Y represents optionally substituted triazinyl.

In another embodiment, Y represents optionally substituted quinoxalinyl.

In another embodiment, Y represents optionally substituted purin-3-yl.

In another embodiment, Y represents optionally substituted 7H-purin-6-yl.

In another embodiment, Y represents optionally substituted purin-7-yl.

In another embodiment, Y represents optionally substituted pyrazolo[3,4-d]pyrimidin-4-yl.

In another embodiment, Y represents optionally substituted pyrido[2,3-d]pyrimidin-4-yl.

In another embodiment, Y represents optionally substituted pyrido[3,4-d]pyrimidin-4-yl.

Suitably, Y represents optionally substituted pyrimidinyl or optionally substituted purinyl.

In one embodiment, Y represents optionally substituted pyrimidinyl. In one aspect of that embodiment, Y represents optionally substituted pyrimidin-2-yl. In another aspect of that embodiment, Y represents optionally substituted pyrimidin-5-yl.

In another embodiment, Y represents optionally substituted purinyl. In one aspect of that embodiment, Y represents optionally substituted purin-1-yl. In another aspect of that embodiment, Y represents optionally substituted purin-2-yl. In another aspect of that embodiment, Y represents optionally substituted purin-3-yl. In another aspect of that embodiment, Y represents optionally substituted 7H-purin-6-yl. In another aspect of that embodiment, Y represents optionally substituted purin-7-yl. In a further aspect of that embodiment, Y represents optionally substituted purin-8-yl.

Examples of optional substituents which may be present on the group Y include one, two or three atoms or groups independently selected from halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkyl-amino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl. Further examples include oxo and arylamino. An additional example is C$_{1-6}$ alkoxyaryl(C$_{1-6}$)alkylamino.

Selected examples of optional substituents on the group Y include halogen, C$_{1-6}$ alkyl, hydroxy, oxo, amino, C$_{1-6}$ alkylamino, di(C$_{1-6}$)alkylamino, arylamino and C$_{1-6}$ alkoxyaryl(C$_{1-6}$)alkylamino.

Typical examples of optional substituents on the group Y include halogen, C$_{1-6}$ alkyl, hydroxy, oxo, amino, C$_{1-6}$ alkylamino, di(C$_{1-6}$)alkylamino and arylamino.

Examples of particular substituents on the group Y include fluoro, chloro, bromo, cyano, nitro, methyl, trifluoromethyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, cyclopropylcarbonyl, azetidinylcarbonyl, N-methylazetidinylcarbonyl, pyrrolidinylcarbonyl, N-methylpyrrolidinylcarbonyl, piperidinylcarbonyl, N-methylpiperidinylcarbonyl, piperazinylcarbonyl, N-methylpiperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl. Further examples include isopropyl, oxo, tert-butylamino and phenylamino. An additional example is methoxybenzylamino.

Specific examples of particular substituents on the group Y include chloro, methyl, isopropyl, hydroxy, oxo, amino, methylamino, tert-butylamino, dimethylamino, phenylamino and methoxybenzylamino. Favoured examples include chloro, methyl, isopropyl, hydroxy, oxo, amino, methylamino, tert-butylamino, dimethylamino and phenylamino. Illustrative examples include amino and methyl.

Definitive values of Y include aminoisoquinolinyl, (chloro)(methyl)pyrimidinyl, aminopyrimidinyl, (amino)(methyl)pyrimidinyl, (amino)(isopropyl)pyrimidinyl, (amino)(hydroxy)pyrimidinyl, di(amino)pyrimidinyl, (methyl)(methylamino)pyrimidin-2-yl, (tert-butylamino)pyrimidinyl, (dimethylamino)(methyl)pyrimidinyl, (phenylamino)-pyrimidinyl, aminotriazinyl, (amino)(methyl)triazinyl, (amino)(methyl)(oxo)triazinyl, (methoxybenzylamino)(methyl)triazinyl, quinoxalinyl, 7H-purin-6-yl, 6-aminopurin-3-yl, 6-aminopurin-7-yl, pyrazolo[3,4-d]pyrimidin-4-yl and pyridopyrimidin-4-yl.

Suitable values of Y include aminoisoquinolinyl, (chloro)(methyl)pyrimidinyl, aminopyrimidinyl, (amino)(methyl)pyrimidinyl, (amino)(isopropyl)pyrimidinyl, (amino)(hydroxy)pyrimidinyl, di(amino)pyrimidinyl, (methyl)(methylamino)pyrimidin-2-yl, (tert-butylamino)pyrimidinyl, (dimethylamino)(methyl)pyrimidinyl, (phenylamino)-pyrimidinyl, (amino)(methyl)triazinyl, (amino)(methyl)(oxo)triazinyl, quinoxalinyl, 7H-purin-6-yl, 6-aminopurin-3-yl, 6-aminopurin-7-yl and pyridopyrimidin-4-yl.

Specific values of Y include aminoisoquinolinyl, (methyl)(methylamino)-pyrimidin-2-yl, aminotriazinyl, (amino)(methyl)triazinyl, (amino)(methyl)(oxo)triazinyl, (methoxybenzylamino)(methyl)triazinyl, quinoxalinyl, 7H-purin-6-yl, 6-aminopurin-3-yl, 6-aminopurin-7-yl, pyrazolo[3,4-d]pyrimidin-4-yl and pyridopyrimidin-4-yl.

Typical values of Y include purin-6-yl, 6-aminopurin-3-yl and 2-amino-4-methylpyrimidin-6-yl.

Suitable values for the group -Alk$^1$-L$^1$-Y include purin-6-ylthiomethyl, 6-aminopurin-3-ylmethyl and (2-amino-4-methylpyrimidin-6-yl)oxymethyl.

Typically, $R^1$, $R^2$ and $R^3$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, aminosulfonyl, $C_{1-6}$ alkylaminosulfonyl or di($C_{1-6}$)alkylaminosulfonyl.

Suitable values of $R^1$, $R^2$ and/or $R^3$ include hydrogen, halogen, cyano, $C_{1-6}$ alkyl, aryl($C_{1-6}$)alkyl and $C_{1-6}$ alkoxy.

Typical values of $R^1$, $R^2$ and/or $R^3$ include hydrogen, halogen, $C_{1-6}$ alkyl, aryl($C_{1-6}$)alkyl and $C_{1-6}$ alkoxy.

Suitably, $R^1$, $R^2$ and $R^3$ independently represent hydrogen, fluoro, chloro, bromo, cyano, nitro, methyl, trifluoromethyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethyl-aminocarbonyl, aminosulfonyl, methylaminosulfonyl or dimethylaminosulfonyl. Additionally, $R^1$, $R^2$ and/or $R^3$ may suitably represent ethyl or benzyl.

Appositely, $R^1$ represents hydrogen, halogen, cyano, $C_{1-6}$ alkyl, aryl($C_{1-6}$)alkyl or $C_{1-6}$ alkoxy.

Typically, $R^1$ represents hydrogen, halogen, $C_{1-6}$ alkyl, aryl($C_{1-6}$)alkyl or $C_{1-6}$ alkoxy.

Suitably, $R^1$ represents hydrogen or $C_{1-6}$ alkyl, typically methyl.

In one embodiment, $R^1$ represents hydrogen. In another embodiment, $R^1$ represents halogen, particularly fluoro or chloro. In one aspect of that embodiment, $R^1$ represents fluoro. In another aspect of that embodiment, $R^1$ represents chloro. In another embodiment, $R^1$ represents cyano. In a further embodiment, $R^1$ represents $C_{1-6}$ alkyl, particularly methyl or ethyl. In one aspect of that embodiment, $R^1$ represents methyl. In another aspect of that embodiment, $R^1$ represents ethyl. In a still further embodiment, $R^1$ represents aryl($C_{1-6}$)alkyl, especially benzyl. In an additional embodiment, $R^1$ represents $C_{1-6}$ alkoxy, especially methoxy.

Typically, $R^2$ represents hydrogen or halogen.

In one embodiment, $R^2$ represents hydrogen. In another embodiment, $R^2$ represents halogen, particularly fluoro or chloro. In one aspect of that embodiment, $R^2$ represents fluoro. In another aspect of that embodiment, $R^2$ represents chloro.

Typically, $R^3$ represents hydrogen.

In a particular embodiment, $R^2$ and $R^3$ both represent hydrogen.

Typical values for the moiety A include phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl.

Suitable values of A include phenyl, thienyl, oxazolyl, isoxazolyl, pyrazolyl and pyridinyl.

In one embodiment, A represents phenyl. In another embodiment, A represents thienyl. In a further embodiment, A represents oxazolyl. In a further embodiment, A represents isoxazolyl. In a still further embodiment, A represents pyrazolyl. In an additional embodiment, A represents pyridinyl.

The group A typically represents phenyl.

Typically, $R^5$, $R^6$ and $R^7$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, aminosulfonyl, $C_{1-6}$ alkylaminosulfonyl, di($C_{1-6}$)alkylaminosulfonyl, $C_{3-7}$ cycloalkyl or $C_{3-6}$ heterocycloalkyl, or optionally substituted monocyclic aryl or heteroaryl.

Typical values of $R^5$, $R^6$ and/or $R^7$ include hydrogen, halogen, $C_{1-6}$ alkyl, trifluoromethyl, $C_{1-6}$ alkoxy, trifluoromethoxy, $C_{2-6}$ alkylcarbonylamino and aryl.

Suitably, $R^5$, $R^6$ and $R^7$ independently represent hydrogen, fluoro, chloro, bromo, cyano, nitro, methyl, trifluoromethyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethyl-aminocarbonyl, aminosulfonyl, methylaminosulfonyl, dimethylaminosulfonyl, cyclopropyl, azetidinyl, N-methylazetidinyl, tetrahydropyranyl, pyrrolidinyl, N-methylpyrrolidinyl, imidazolidinyl, N-methylimidazolidinyl, tetrahydropyranyl, piperidinyl, N-methylpiperidinyl, piperazinyl, N-methylpiperazinyl, morpholinyl or thiomorpholinyl, or optionally substituted phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl or triazinyl. Additional values include ethyl, isopropyl and isopropoxy.

Optional substituents which may be present on the aryl or heteroaryl groups represented by $R^5$, $R^6$ or $R^7$ include halogen, cyano, $C_{1-3}$ alkyl, $C_{1-3}$ alkoxy, trifluoromethyl, difluoromethoxy, trifluoromethoxy, $C_{1-3}$ alkylthio, $C_{1-3}$ alkylsulfinyl, $C_{1-3}$ alkylsulfonyl, amino, $C_{1-3}$ alkylamino, di($C_{1-3}$) alkylamino, $C_{2-3}$ alkylcarbonylamino, $C_{1-3}$ alkylsulfonylamino, formyl, $C_{2-3}$ alkylcarbonyl, carboxy, $C_{2-3}$ alkoxycarbonyl, aminocarbonyl, $C_{1-3}$ alkylaminocarbonyl, di($C_{1-3}$)alkylaminocarbonyl, aminosulfonyl, $C_{1-3}$ alkylaminosulfonyl and di($C_{1-3}$)alkylaminosulfonyl.

Typically, $R^5$ represents hydrogen, halogen, $C_{1-6}$ alkyl, trifluoromethyl, $C_{1-6}$ alkoxy, trifluoromethoxy, $C_{2-6}$ alkylcarbonylamino or aryl.

In one embodiment, $R^5$ represents hydrogen. In another embodiment, $R^5$ represents halogen, particularly fluoro or chloro. In one aspect of that embodiment, $R^5$ represents fluoro. In another aspect of that embodiment, $R^5$ represents chloro. In a further embodiment, $R^5$ represents $C_{1-6}$ alkyl, particularly methyl, ethyl or isopropyl. In one aspect of that embodiment, $R^5$ represents methyl. In another aspect of that embodiment, $R^5$ represents ethyl. In a further aspect of that embodiment, $R^5$ represents isopropyl. In a further embodiment, $R^5$ represents trifluoromethyl. In a further embodiment, $R^5$ represents $C_{1-6}$ alkoxy, particularly methoxy or isopropoxy. In a further embodiment, $R^5$ represents trifluoromethoxy. In a still further embodiment, $R^5$ represents $C_{2-6}$ alkylcarbonylamino, especially acetylamino. In an additional embodiment, $R^5$ represents aryl, especially phenyl.

Suitably, $R^5$ represents hydrogen, trifluoromethyl or $C_{1-6}$ alkyl, typically methyl.

Typically, $R^6$ represents hydrogen, halogen or $C_{1-6}$ alkyl.

In one embodiment, $R^6$ represents hydrogen. In another embodiment, $R^6$ represents halogen, particularly fluoro or chloro. In one aspect of that embodiment, $R^6$ represents fluoro. In another aspect of that embodiment, $R^6$ represents chloro. In a further embodiment, $R^6$ represents $C_{1-6}$ alkyl, especially methyl.

Typically, $R^7$ represents hydrogen.

In a particular embodiment, $R^6$ and $R^7$ both represent hydrogen.

Typically, $R^8$ represents hydrogen or $C_{1-6}$ alkyl.

In one embodiment, $R^8$ represents hydrogen. In another embodiment, $R^8$ represents halogen, particularly fluoro or chloro. In one aspect of that embodiment, $R^8$ represents fluoro. In another aspect of that embodiment, $R^8$ represents chloro. In a further embodiment, $R^8$ represents $C_{1-6}$ alkyl, especially methyl. In an additional embodiment, $R^8$ represents $C_{1-6}$ alkoxy, especially methoxy.

Suitable values of the group $R^8$ include hydrogen, fluoro, chloro, bromo, methyl and methoxy. Suitably, $R^8$ represents hydrogen or methyl. $R^8$ typically represents hydrogen.

In one embodiment, $R^9$ represents hydrogen. In another embodiment, $R^9$ represents $C_{1-6}$ alkyl, especially methyl.

Suitable values of the group $R^9$ include hydrogen and methyl.

One sub-class of compounds of use according to the invention is represented by the compounds of formula (IIA) and N-oxides thereof, and pharmaceutically acceptable salts and solvates thereof:

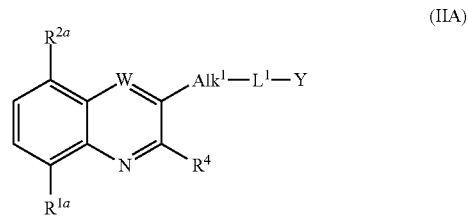

(IIA)

wherein $R^{1a}$ is as defined above for $R^1$, $R^{2a}$ is as defined above for $R^2$, and W, $Alk^1$, $L^1$, Y and $R^4$ are as defined above.

In a specific embodiment, $R^{2a}$ represents hydrogen.

One particular subclass of novel compounds according to the invention is represented by the compounds of formula (IIA) and N-oxides thereof, and pharmaceutically acceptable salts and solvates thereof, wherein $R^{1a}$ and $R^{2a}$ are as defined above in relation to formula (IIA); $Alk^1$, $L^1$ and $R^4$ are as defined above in relation to formula (I); W represents $CR^8$; and Y is as defined above in relation to the novel compounds of formula (IA).

Specific novel compounds in accordance with the present invention include each of the compounds whose preparation is described in the accompanying Examples, and pharmaceutically acceptable salts and solvates thereof.

The present invention also provides a pharmaceutical composition which comprises a novel compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds of use in the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

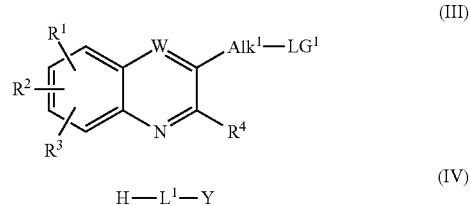

wherein $Alk^1$, Y, W, $R^2$, $R^3$ and $R^4$ are as defined above, and $LG^1$ represents a suitable leaving group.

The leaving group $LG^1$ is typically a halogen atom, e.g. bromo.

The reaction is conveniently effected at ambient or elevated temperature in a suitable solvent, e.g. N,N-dimethylformamide or acetonitrile. The reaction may be performed in the presence of a suitable base, e.g. an inorganic base such as potassium carbonate, cesium carbonate, sodium hydride or aqueous sodium hydroxide.

The intermediates of formula (III) above wherein $LG^1$ is bromo may be prepared from a compound of formula (V):

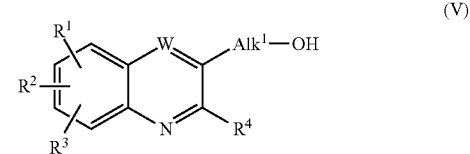

wherein $Alk^1$, W, $R^1$, $R^2$, $R^3$ and $R^4$ are as defined above; by bromination.

The reaction is conveniently effected by stirring compound (V) with an appropriate brominating agent, e.g. phosphorus tribromide, in a suitable solvent, e.g. a halogenated hydrocarbon such as dichloromethane.

Alternatively, the intermediates of formula (III) above wherein $Alk^1$ represents methylene and $LG^1$ is bromo may be prepared from a compound of formula (VI):

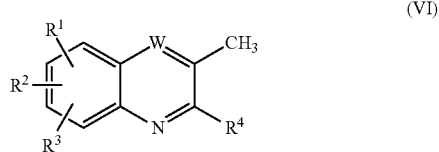

wherein W, $R^1$, $R^2$, $R^3$ and $R^4$ are as defined above; by bromination.

The reaction is conveniently effected at an elevated temperature in a suitable solvent, e.g. a halogenated solvent such as carbon tetrachloride, in the presence of a suitable brominating agent, e.g. N-bromosuccinimide, typically in the presence of a catalyst such as benzoyl peroxide.

In another procedure, the compounds of formula (I) wherein $L^1$ represents oxygen may be prepared by a process which comprises reacting a compound of formula (V) as defined above with a compound of formula $LG^2$-Y, in which Y is as defined above and $LG^2$ represents a suitable leaving group.

The leaving group $LG^2$ is typically a halogen atom, e.g. chloro.

The reaction is conveniently effected by stirring compound (V) with a compound $LG^2$-Y in a suitable solvent, e.g. N,N-dimethylformamide or 1,4-dioxane, typically under basic conditions, e.g. in the presence of an inorganic base such as sodium hydride.

In a further procedure, compounds of formula (I) where W represents N, $Alk^1$ represents methylene, $L^1$ represents a covalent bond and Y represents 6-aminopurin-3-yl may be prepared by a one-pot process which involves reacting a diamine of formula (VII) with a dione of formula (VIII):

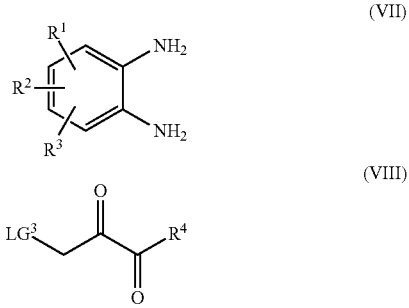

wherein $R^1$, $R^2$, $R^3$ and $R^4$ are as defined above, and $LG^3$ represents a suitable leaving group; in the presence of 6-aminopurine (adenine).

The leaving group $LG^3$ is typically a halogen atom, e.g. bromo.

The reaction is conveniently effected at an elevated temperature in a suitable solvent, e.g. an alcohol such as ethanol.

In another procedure, the compounds of formula (I) wherein $L^1$ represents sulfur may be prepared by a process which comprises reacting a compound of formula $LG^2$-Y with a compound of formula (IX):

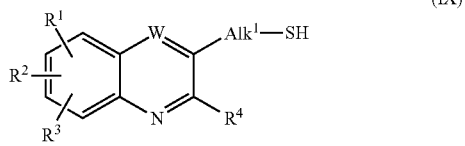

wherein Y, $LG^2$, $Alk^1$, W, $R^1$, $R^2$, $R^3$ and $R^4$ are as defined above.

The reaction is conveniently effected by stirring compound (IX) with a compound $LG^2$-Y in a suitable solvent, e.g. a lower alkanol such as methanol, typically under basic conditions, e.g. in the presence of an alkali metal alkoxide such as sodium methoxide.

The intermediates of formula (IX) may typically be prepared by treating a suitable compound of formula (III) above with thioacetic acid; followed by treatment of the resulting compound with a base, e.g. an alkali metal alkoxide such as sodium methoxide.

In another procedure, the compounds of formula (I) wherein $L^1$ represents $NR^9$ may be prepared by a process which comprises reacting a compound of formula $LG^2$-Y with a compound of formula (X):

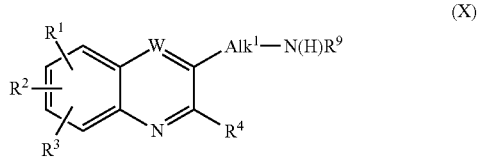

wherein Y, $LG^2$, $Alk^1$, W, $R^1$, $R^2$, $R^3$, $R^4$ and $R^9$ are as defined above.

The reaction is conveniently effected at an elevated temperature in a suitable solvent, e.g. tetrahydrofuran, n-butanol or 1-methyl-2-pyrrolidinone (NMP). The reaction may be performed in the presence of a suitable base, e.g. an organic base such as N,N-diisopropylethylamine.

The intermediates of formula (X) wherein $R^9$ represents hydrogen may be prepared by treating a suitable compound of formula (III) above with potassium phthalimide; followed by treatment of the resulting compound with hydrazine. Alternatively, they may be prepared by treating a suitable compound of formula (III) above with sodium azide; followed by treatment of the resulting compound with triphenylphosphine.

In an additional procedure, the compounds of formula (I) wherein $Alk^1$ represents methylene and $L^1$ represents $NR^9$ may be prepared by a process which comprises reacting a compound of formula Y—$N(H)R^9$ with a compound of formula (XI):

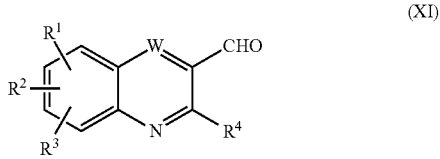

wherein Y, W, $R^1$, $R^2$, $R^3$, $R^4$ and $R^9$ are as defined above; under reducing conditions.

The reaction is conveniently effected by stirring compound (XI) with a compound Y—$N(H)R^9$ at an elevated temperature in a suitable solvent, e.g. a cyclic ether such as tetrahydrofuran, in the presence of a reducing agent. A suitable reducing agent comprises a mixture of di-n-butyltin dichloride and phenylsilane.

The intermediates of formula (X) wherein $Alk^1$ represents methylene and $R^9$ represents $C_{1-6}$ alkyl, e.g. methyl, may be prepared by treating a suitable compound of formula (XI) above with a $C_{1-6}$ alkylamine, e.g. methylamine, in the presence of titanium(IV) n-propoxide and a base, e.g. an organic base such as N,N-diisopropylamine; followed by treatment of the resulting compound with a reducing agent, e.g. triacetoxyborohydride.

Where they are not commercially available, the starting materials of formula (IV), (V), (VI), (VII), (VIII) and (XI) may be prepared by methods analogous to those described in the accompanying Examples, or by standard methods well known from the art. By way of illustration, the intermediates of formula (V) wherein $Alk^1$ represents methylene may be prepared from the corresponding aldehyde precursor of formula (XI) by treatment with a reducing agent, e.g. sodium borohydride. Furthermore, the group $R^4$ may be introduced into the molecule by standard techniques, such as Suzuki conditions, as described in several of the accompanying Examples.

It will be understood that any compound of formula (I) initially obtained from any of the above processes may, where appropriate, subsequently be elaborated into a further compound of formula (I) by techniques known from the art. By way of illustration, a compound of formula (I) wherein the moiety Y is substituted by a halogen atom, e.g. chloro, may be converted into the corresponding compound wherein Y is substituted by amino (—$NH_2$) by treatment with ammonia. Similarly, a compound of formula (I) wherein the moiety Y is substituted by a halogen atom, e.g. chloro, may be converted into the corresponding compound wherein Y is substituted by $C_{1-6}$ alkylamino (e.g. methylamino or tert-butylamino), di($C_{1-6}$)alkylamino (e.g. dimethylamino) or arylamino (e.g. phenylamino) by treatment with the appropriate $C_{1-6}$ alkylamine (e.g. methylamine or tert-butylamine), di($C_{1-6}$)alkylamine (e.g. dimethylamine) or arylamine (e.g. aniline) respectively.

Where a mixture of products is obtained from any of the processes described above for the preparation of compounds of use in the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds of use in the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The following Examples illustrate the preparation of compounds according to the invention.

The compounds of use in this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 µM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 µM or better.

EXAMPLES

Abbreviations

| Abbreviations | |
|---|---|
| EtOAc: | ethyl acetate |
| MeOH: | methanol |
| MeCN: | acetonitrile |
| $NH_4OAc$: | ammonium acetate |
| DMF: | N,N-dimethylformamide |
| Pd(OAc)$_2$: | palladium(II) acetate |
| PPh$_3$: | triphenylphosphine |
| THF: | tetrahydrofuran |
| MTBE: | tert-butyl methyl ether |
| DIPEA: | N,N-diisopropylethylamine |
| Me: | methyl |
| Ph: | phenyl |
| TFA: | trifluoroacetic acid |
| Pd(PPh$_3$)$_4$: | tetrakis(triphenylphosphine)palladium(0) |
| r.t.: | room temperature |
| SiO$_2$: | silica |
| br.: | broad |
| HPLC: | High Performance Liquid Chromatography |
| LCMS: | Liquid Chromatography Mass Spectrometry |
| ES+: | Electrospray Positive Ionisation |
| DCM: | dichloromethane |
| EtOH: | ethanol |
| NBS: | N-bromosuccinimide |
| AcOH: | acetic acid |
| DME: | ethylene glycol dimethyl ether |
| TBAB: | tetra-n-butylammonium bromide |
| DMSO: | dimethylsulfoxide |
| Et$_2$O: | diethyl ether |
| NMP: | 1-methyl-2-pyrrolidinone |
| TFA: | trifluoroacetic acid |
| Et: | ethyl |
| n-BuOH: | n-butanol |
| DIBAL-H: | diisobutylaluminium hydride |
| RT: | retention time |
| h: | hour |
| M: | mass |

Analytical Conditions

All NMRs were obtained either at 300 MHz or 400 MHz.

Compounds were named with the aid of ACD Labs Name (v. 9.0 or 10.0) supplied by Advanced Chemical Development, Toronto, Canada; or with the aid of Beilstein Autonom.

All reactions involving air- or moisture-sensitive reagents were performed under a nitrogen atmosphere using dried solvents and glassware. Degassing was performed by bubbling nitrogen through the reaction mixture.

Compounds that required preparative HPLC were purified using Method 1, 2 or 8 below.

Method 1: Phenomenex Luna C18(2) 250×21.2 mm, 5 μm column. Mobile phase A: 99.92% water, 0.08% formic acid. Mobile phase B: 99.92% MeCN, 0.08% formic acid. Gradient program (flow rate 25.0 mL/min), column temperature: ambient, variable gradient.

Method 2: Phenomenex Luna C18(2) 250×21.2 mm, 5 μm column. Mobile phase A: 10 mM ammonium acetate in water. Mobile Phase B: 10 mM ammonium acetate in MeCN. Gradient program (flow rate 25.0 mL/min), column temperature: ambient, variable gradient.

Method 8: Winters Sunfire C18 100×19 mm, 5 μm column. Mobile phase A: 10 mM ammonium hydrogencarbonate. Mobile phase B: MeCN. Gradient program (flow rate 20.0 mL/min), column temperature: ambient, variable gradient.

Analytical methods used for LCMS were Methods 3 to 7 below.

Method 3: Phenomenex Luna C18(2) 100×4.6 mm, 5 μm column. Mobile phase A: 99.92% water, 0.08% formic acid. Mobile phase B: 99.92% MeCN, 0.08% formic acid. Gradient program (flow rate 3.0 mL/min, column temperature 35° C.):

| Time | A % | B % |
|------|-----|-----|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 4: Phenomenex Luna C18(2) 100×4.6 mm, 5 μm column. Mobile phase A: 5 mM NH$_4$OAc, pH 5.8. Mobile phase B: 95:5 MeCN:100 mM NH$_4$OAc, pH 5.8. Gradient program (flow rate 3.0 mL/min, column temperature 35° C.):

| Time | A % | B % |
|------|-----|-----|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 5: Phenomenex Luna C18(2) 100×4.6 mm, 5 μm column. Mobile phase A: 99.9% water, 0.1% formic acid. Mobile phase B: 99.9% MeCN, 0.1% formic acid. Gradient program (flow rate 2.0 mL/min):

| Time | A % | B % |
|------|-----|-----|
| 0.00 | 95.0 | 5.0 |
| 0.50 | 95.0 | 5.0 |
| 3.50 | 5.0 | 95.0 |
| 4.50 | 5.0 | 95.0 |
| 4.60 | 95.0 | 5.0 |
| 5.00 | 95.0 | 5.0 |

Method 6: Phenomenex Luna C18(2) 100×4.6 mm, 5 μm column. Mobile phase A: 99.9% water, 0.1% formic acid. Mobile phase B: 99.9% MeCN, 0.1% formic acid. Gradient program (flow rate 2.0 mL/min):

| Time | A % | B % |
|------|-----|-----|
| 0.00 | 95.0 | 5.0 |
| 3.50 | 5.0 | 95.0 |
| 5.50 | 5.0 | 95.0 |
| 5.60 | 95.0 | 5.0 |
| 6.50 | 95.0 | 5.0 |

Method 7: Waters Xterra MS C18 100×4.6 mm, 5 μm column. Mobile phase A: water with 10 mM ammonium hydrogencarbonate. Mobile phase B: MeCN. Gradient program (flow rate 2.0 mL/min):

| Time | A % | B % |
|------|-----|-----|
| 0.00 | 95.0 | 5.0 |
| 0.50 | 95.0 | 5.0 |
| 4.00 | 5.0 | 95.0 |
| 5.50 | 5.0 | 95.0 |
| 5.60 | 95.0 | 5.0 |
| 6.50 | 95.0 | 5.0 |

Intermediate 1

2-(Bromomethyl)-3-phenylquinoxaline

A mixture of 2-methyl-3-phenylquinoxaline (2.00 g, 9.08 mmol), NBS (1.45 g, 8.17 mmol) and benzoyl peroxide (catalytic amount) in carbon tetrachloride (75 mL) was heated at reflux for 5 h, then allowed to cool to r.t. The reaction mixture was filtered, the filtrate was concentrated in vacuo and the residue purified by column chromatography (SiO$_2$, 0-20% EtOAc in heptane) to give the title compound (1.22 g, 45%) as a cream-coloured solid. $\delta_H$ (CDCl$_3$) 8.11-8.19 (m, 2H), 7.75-7.85 (m, 4H), 7.52-7.62 (m, 3H), 4.76 (s, 2H). LCMS (ES+) 299.1, 301.1 (M+H)$^+$, RT 4.10 minutes (Method 3).

Intermediate 2

2-Methyl-3-[3-(trifluoromethyl)phenyl]quinoxaline

A mixture of 1,2-phenylenediamine (1.00 g, 9.25 mmol) and 1-[3-(trifluoromethyl)phenyl]propane-1,2-dione (2.00 g, 9.25 mmol) in water (80 mL) was heated at 60° C. overnight, then for 5 h with vigorous stirring. The reaction mixture was allowed to cool to r.t. then acidified with 2N HCl (ca 20 mL) and extracted with EtOAc. The organic phase was washed with brine, dried (MgSO$_4$) and concentrated in vacuo. The residue was triturated with heptane to give the title compound (1.44 g, 54%) as a cream-coloured solid. $\delta_H$ (CDCl$_3$) 8.05-8.16 (m, 2H), 7.96 (s, 1H), 7.85-7.90 (m, 1H), 7.72-7.82 (m, 3H), 7.64-7.71 (m, 1H), 2.79 (s, 3H). LCMS (ES+) 289.3 (M+H)$^+$, RT 4.21 minutes (Method 3).

Intermediate 3

2-(Bromomethyl)-3-[3-(trifluoromethyl)phenyl]quinoxaline

The title compound was prepared in a similar manner to Intermediate 1, using Intermediate 2, and was obtained as a cream-coloured waxy solid (15%) after purification by column chromatography (SiO$_2$, 0-20% EtOAc in heptane). $\delta_H$ (CDCl$_3$) 8.13-8.20 (m, 2H), 8.08 (s, 1H), 8.00-8.04 (m, 1H), 7.80-7.88 (m, 3H), 7.68-7.75 (m, 1H), 4.72 (s, 2H). LCMS (ES+) 367.1, 369.1 (M+H)$^+$, RT 4.49 minutes (Method 3).

Intermediate 4

(2-Phenylquinolin-3-yl)methanol

Sodium borohydride (45 mg, 1.18 mmol) was added to a solution of 2-phenyl-quinoline-3-carbaldehyde (212 mg, 0.91 mmol) in MeOH (7 mL) and the reaction mixture was stirred at r.t. for 1 h. The reaction was quenched by the addition of glacial AcOH (0.1 mL) and the solvent was removed in vacuo. The residue was partitioned between EtOAc and 10% aqueous $K_2CO_3$ solution. The organic phase was dried ($MgSO_4$) and the solvent removed in vacuo to give the title compound (quantitative) as a clear oil which crystallized on standing to a yellow solid. $\delta_H$ ($CDCl_3$) 8.32 (s, 1H), 8.12-8.19 (m, 1H), 7.80-7.86 (m, 1H), 7.67-7.74 (m, 1H), 7.50-7.59 (m, 3H), 7.37-7.47 (m, 3H), 4.71 (s, 2H), 2.76 (br. s, 1H). LCMS (ES+) 236.1 (M+H)$^+$, RT 3.04 minutes (Method 4).

Intermediate 5

3-(Bromomethyl)-2-phenylquinoline

Phosphorus tribromide (560 mg, 2.07 mmol) was added to a solution of Intermediate 4 (243 mg, 1.03 mmol) in DCM (3.6 mL) and the reaction mixture was stirred at r.t. for 75 minutes. Further phosphorus tribromide (144 mg, 0.53 mmol) was added and the reaction mixture left to stir overnight. The mixture was partitioned between DCM and 10% aqueous $K_2CO_3$ solution; the organic phase was dried ($MgSO_4$) and the solvent removed in vacuo to give the title compound (226 mg, 73%) as a white solid. $\delta_H$ ($CDCl_3$) 8.36 (s, 1H), 8.13-8.18 (m, 1H), 7.84-7.90 (m, 1H), 7.67-7.78 (m, 3H), 7.46-7.61 (m, 4H), 4.65 (s, 2H). LCMS (ES+) 298.0, 300.0 (M+H)$^+$, RT 3.98 minutes (Method 3).

Intermediate 6

(8-Methyl-2-phenylquinolin-3-yl)methanol

A mixture of (2-chloro-8-methylquinolin-3-yl)methanol (413 mg, 2.0 mmol) and $K_2CO_3$ (828 mg, 6.0 mmol) in DME (7.5 mL) and water (7.5 mL) was degassed (×3). Phenylboronic acid (293 mg, 2.4 mmol), $PPh_3$ (21 mg, 0.08 mmol) and $Pd(OAc)_2$ (4.5 mg, 0.02 mmol) were added, the mixture was degassed, then heated at reflux for 75 minutes. The reaction mixture was allowed to cool to r.t. then extracted with EtOAc (2×20 mL). The combined organic phases were washed with water (20 mL), dried ($MgSO_4$) and evaporated in vacuo. The residue was purified by column chromatography ($SiO_2$, 10-100% EtOAc in heptane) then by preparative HPLC (Method 1). The product obtained was partitioned between EtOAc and 10% aqueous $K_2CO_3$ solution. The organic phase was dried ($MgSO_4$) and evaporated in vacuo to give the title compound (241 mg, 49%) as a white solid. $\delta_H$ ($CDCl_3$) 8.31 (s, 1H), 7.68-7.76 (m, 3H), 7.41-7.59 (m, 5H), 4.86 (d, J 5.1 Hz, 2H), 2.82 (s, 3H), 1.85 (t, J 5.5 Hz, 1H). LCMS (ES+) 250.1 (M+H)$^+$, RT 3.52 minutes (Method 3).

Intermediate 7

3-(Bromomethyl)-8-methyl-2-phenylquinoline

Phosphorus tribromide (262 mg, 0.96 mmol) was added to a solution of Intermediate 6 (120 mg, 0.48 mmol) in DCM (2.0 mL) and the reaction mixture was stirred at r.t. for 2.7 h. Further phosphorus tribromide (262 mg, 0.96 mmol) was added and the reaction mixture left to stir overnight. The mixture was partitioned between EtOAc and 10% aqueous $K_2CO_3$ solution. The aqueous phase was reextracted with DCM and the combined organic fractions were dried ($MgSO_4$) and the solvent removed in vacuo to give the title compound (112 mg, 74%) as a white solid. $\delta_H$ ($CDCl_3$) 8.33 (s, 1H), 7.76-7.82 (m, 2H), 7.67-7.73 (m, 1H), 7.43-7.62 (m, 5H), 4.69 (s, 2H), 2.82 (s, 3H). LCMS (ES+) 312.1, 314.0 (M+H)$^+$, RT 4.78 minutes (Method 3).

Intermediate 8

[2-(2-Methylphenyl)quinolin-3-yl]methanol

A mixture of (2-chloro-3-quinolinyl)methanol (500 mg, 2.60 mmol), potassium phosphate tribasic (770 mg, 3.60 mmol), $Pd(OAc)_2$ (30 mg, 0.13 mmol), $PPh_3$ (136 mg, 0.52 mmol) and o-tolylboronic acid (530 mg, 3.90 mmol) in water (4.0 mL) was degassed. DME (13 mL) was added and the mixture was degassed further, then heated at 120° C. for 30 minutes. The solvent was removed in vacuo and the residue was partitioned between EtOAc and 10% aqueous potassium carbonate solution. The aqueous phase was extracted with further EtOAc and the combined organic fractions were dried ($MgSO_4$) and evaporated in vacuo. The residue was purified by column chromatography ($SiO_2$, 10-40% EtOAc in heptane) then by preparative HPLC (Method 2). The product obtained was partitioned between DCM and 10% aqueous $K_2CO_3$ solution. The organic phase was dried ($MgSO_4$) and evaporated in vacuo to give the title compound (240 mg, 37%) as a clear gum. $\delta_H$ ($CDCl_3$) 8.34 (s, 1H), 8.12-8.17 (m, 1H), 7.86-7.91 (m, 1H), 7.69-7.76 (m, 1H), 7.54-7.62 (m, 1H), 7.18-7.37 (m, 4H), 4.52 (br. d, J 4.3 Hz, 2H), 2.40 (br. t, J 5.1 Hz, 1H), 2.07 (s, 3H). LCMS (ES+) 250.1 (M+H)$^+$, RT 3.17 minutes (Method 4).

Intermediate 9

3-(Bromomethyl)-2-(2-methylphenyl)quinoline

The title compound was prepared in a similar manner to Intermediate 5, using Intermediate 8, and was obtained as a yellow gum (83%). $\delta_H$ ($CDCl_3$) 8.36 (s, 1H), 8.12-8.17 (m, 1H), 7.86-7.91 (m, 1H), 7.72-7.79 (m, 1H), 7.56-7.63 (m, 1H), 7.28-7.41 (m, 4H), 4.29-4.63 (br. m, 2H), 2.14 (s, 3H). LCMS (ES+) 312.0, 314.0 (M+H)$^+$, RT 4.12 minutes (Method 3).

Intermediate 10

8-Methyl-2-(thien-3-yl)quinoline-3-carboxaldehyde

A mixture of 2-chloro-8-methylquinoline-3-carboxaldehyde (258 mg, 1.26 mmol), 3-thiopheneboronic acid (193 mg, 1.51 mmol), $K_2CO_3$ (260 mg, 1.88 mmol), palladium(II) acetate (5.6 mg, 0.025 mmol) and triphenylphosphine (26.3 mg, 0.10 mmol) in water (2 mL) was degassed. 1,4-Dioxane (6 mL) was added and the mixture further degassed, then heated at 100° C. for 1 h under microwave irradiation. The reaction mixture was diluted with DCM (30 mL) and water (10 mL). The organic layer was separated, dried ($MgSO_4$) and concentrated in vacuo. Purification by column chromatography ($SiO_2$, 10% EtOAc in heptane) gave the title compound (297 mg, 93%) as a colourless crystalline solid. $\delta_H$ ($CDCl_3$) 10.40 (s, 1H), 8.75 (s, 1H), 7.83 (d, J 9 Hz, 1H), 7.60-7.73 (m, 3H), 7.46-7.54 (m, 2H), 2.85 (s, 3H). LCMS (ES+) 254.2 (M+H)$^+$, RT 4.29 minutes (Method 3).

Intermediate 11

2-(2-Acetamidophenyl)-8-methylquinoline-3-carboxaldehyde

The title compound was prepared in a similar manner to Intermediate 10, using 2-chloro-8-methylquinoline-3-carboxaldehyde, and was obtained as a buff-coloured solid (323 mg, 89%) after purification by column chromatography (SiO$_2$, 50% EtOAc in heptane). $\delta_H$ (CDCl$_3$) CHO not visible, 8.75 (d, J 12 Hz, 1H), 8.22 (s, 1H), 7.71 (d, J 9 Hz, 1H), 7.62 (d, J 9 Hz, 1H), 7.34-7.56 (m, 4H), 7.30 (m, 1H), 2.99-2.86 (m, 4H), 2.35 (s, 3H). LCMS (ES+) 305.1 (M+H)$^+$, RT 3.52 minutes (Method 3).

Intermediate 12

8-Methyl-2-[2-(trifluoromethoxy)phenyl]quinoline-3-carboxaldehyde

The title compound was prepared in a similar manner to Intermediate 6, using 2-chloro-8-methylquinoline-3-carboxaldehyde, and was obtained as a white solid (344 mg, 91%) after purification by column chromatography (SiO$_2$, 10% EtOAc in heptane). $\delta_H$ (CDCl$_3$) 10.00 (s, 1H), 8.80 (s, 1H), 7.87 (d, J 12 Hz, 1H), 7.70-7.75 (m, 2H), 7.45-7.60 (m, 3H), 7.40-7.45 (m, 1H), 2.85 (s, 3H). LCMS (ES+) 332.2 (M+H)$^+$, RT 4.69 minutes (Method 4).

Intermediate 13

8-Methyl-2-(2-ethylphenyl)quinoline-3-carboxaldehyde

The title compound was prepared in a similar manner to Intermediate 6, using 2-chloro-8-methylquinoline-3-carboxaldehyde, and was obtained as a clear oil (500 mg, 75%) after purification by column chromatography (SiO$_2$, 5% EtOAc in heptane). $\delta_H$ (CDCl$_3$) 9.92 (s, 1H), 8.81 (s, 1H), 7.87 (d, J 8.3 Hz, 1H), 7.70-7.74 (m, 1H), 7.53 (dd, J 8.1, 7.2 Hz, 1H), 7.45 (m, 2H), 7.31-7.37 (m, 1H), 7.26-7.31 (m, 1H), 2.81 (s, 3H), 2.52-2.69 (m, 2H), 1.12 (t, J 7.5 Hz, 3H). LCMS (ES+) 276.27 (M+H)$^+$, RT 4.68 minutes (Method 3).

Intermediate 14

8-Methyl-2-(1,3-oxazol-2-yl)quinoline-3-carboxaldehyde

To a solution of 2-chloro-8-methylquinoline-3-carboxaldehyde (250 mg, 1.21 mmol) in DME (3 mL) was added 2-(tributylstannyl)oxazole (0.31 mL, 1.76 mmol) and Pd(PPh$_3$)$_4$ (70 mg, 0.06 mmol). The reaction mixture was heated in a microwave at 100° C. for 45 minutes. More Pd(PPh$_3$)$_4$ (50 mg, 0.04 mmol) was added to the mixture, which was heated at 100° C. for 2 h. Purification by column chromatography (SiO$_2$, 0-100% EtOAc in heptane) gave the title compound as a cream solid (99 mg, 34%). $\delta_H$ (DMSO-d$_6$) 10.85 (s, 1H), 8.91 (s, 1H), 8.52 (d, J 0.6 Hz, 1H), 8.12 (d, J 8.1 Hz, 1H), 7.86 (d, J 7.0 Hz, 1H), 7.64-7.72 (m, 2H), 2.81 (s, 3H). LCMS (ES+) 239 (M+H)$^+$, RT 3.65 minutes (Method 3).

Intermediate 15

2-(3,5-Dimethylisoxazol-4-yl)-8-methylquinoline-3-carboxaldehyde

The title compound was prepared in a similar manner to Intermediate 6, using 2-chloro-8-methylquinoline-3-carboxaldehyde, and was obtained as a yellow solid (187 mg, 72%). $\delta_H$ (CDCl$_3$) 10.10 (s, 1H), 8.81 (s, 1H), 7.87 (d, J 8.1 Hz, 1H), 7.75 (d, J 8.1 Hz, 1H), 7.56 (dd, J 8.1, 7.2 Hz, 1H), 2.82 (s, 3H), 2.44 (s, 3H), 2.39 (s, 3H). LCMS (ES+) 267 (M+H)$^+$, RT 3.79 minutes (Method 3).

Intermediate 16

8-Methyl-2-(2-fluoro-6-methoxyphenyl)quinoline-3-carboxaldehyde

The title compound was prepared in a similar manner to Intermediate 6, using 2-chloro-8-methylquinoline-3-carboxaldehyde, and was obtained as an off-white solid (131 mg, 39%) after purification by column chromatography (SiO$_2$; 10% EtOAc in heptane). $\delta_H$ (CDCl$_3$) 9.92 (s, 1H), 8.79 (s, 1H), 7.86 (d, J 12 Hz, 1H), 7.69 (d, J 9 Hz, 1H), 7.40-7.58 (m, 2H), 6.87-6.97 (m, 1H), 6.80 (d, J 12 Hz, 1H), 3.76 (s, 3H), 2.82 (s, 3H). LCMS (ES+) 296.2 (M+H)$^+$, RT 4.31 minutes (Method 4).

Intermediate 17

2-Chloro-5-fluoro-8-methylquinoline-3-carboxaldehyde

To a stirred solution of DMF (3 mL) at 0° C. was added phosphorus oxychloride (12 mL, 126 mmol) over 30 minutes, keeping the internal temperature below 7° C. N-(5-Fluoro-2-methylphenyl)acetamide (2 g, 12 mmol) was added to the solution and heated to 85° C. overnight. The reaction was cooled to room temperature and added dropwise to water (50 mL). The precipitate was collected by filtration, washed with water and dried in the vacuum oven to give the title compound (274 mg, 10%) as a yellow solid. $\delta_H$ (CDCl$_3$) 10.58 (s, 1H), 9.01 (s, 1H), 7.60-7.70 (m, 1H), 7.15-7.25 (m, 1H), 2.75 (s, 3H).

Intermediate 18

6-Methyl-2-phenylquinoline-3-carboxaldehyde

The title compound was prepared in a similar manner to Intermediate 6, using 2-chloro-6-methylquinoline-3-carboxaldehyde, and was obtained as a white solid (475 mg, 84%). $\delta_H$ (CDCl$_3$) 10.17 (s, 1H), 8.76 (s, 1H), 8.11 (d, J 8.7 Hz, 1H), 7.77 (br s, 1H), 7.66-7.74 (m, 3H), 7.52-7.60 (m, 3H), 2.59 (s, 3H). LCMS (ES+) 248.03 (M+H)$^+$, RT 3.93 minutes (Method 3).

Intermediate 19

7-Methyl-2-phenylquinoline-3-carboxaldehyde

The title compound was prepared in a similar manner to Intermediate 6, using 2-chloro-7-methylquinoline-3-carboxaldehyde, and was obtained as a yellow solid (437 mg, 74%) after purification by column chromatography (SiO$_2$, 5-20% EtOAc in heptane). $\delta_H$ (CDCl$_3$) 10.16 (s, 1H), 8.81 (s, 1H), 8.00 (d, J 0.7 Hz, 1H), 7.91 (d, J 8.5 Hz, 1H), 7.66-7.70 (m, 2H), 7.52-7.60 (m, 3H), 7.47 (dd, J 8.5, 1.5 Hz, 1H), 2.62 (s, 3H). LCMS (ES+) 248.2 (M+H)$^+$, RT 4.06 minutes (Method 4).

Intermediate 20

7-Methyl-2-(2-methylphenyl)quinoline-3-carboxaldehyde

The title compound was prepared in a similar manner to Intermediate 6, using 2-chloro-7-methylquinoline-3-carboxaldehyde, and was obtained as a yellow solid (636 mg, quantitative) after purification by column chromatography (SiO$_2$, 5-20% EtOAc in heptane). $\delta_H$ (CDCl$_3$) 9.90 (s, 1H), 8.56 (s, 1H), 7.97 (s, 1H), 7.93 (d, J 9 Hz, 1H), 7.46-7.50 (m, 1H), 7.20-7.45 (m, 4H), 2.62 (s, 3H), 2.19 (s, 3H). LCMS (ES+) 262.22 (M+H)$^+$, RT 4.16 minutes (Method 4).

Intermediate 21

2-Chloro-7-fluoro-8-methylquinoline-3-carboxaldehyde

To a stirred solution of DMF (3 mL, 39 mmol) at 0° C. was added POCl$_3$ (12 mL, 126 mmol) over 50 minutes. The reaction mixture was allowed to warm to 20° C. before the addition of N-(3-fluoro-2-methylphenyl)acetamide (2.00 g, 12 mmol) took place. The reaction mixture was heated to 85° C. for 18 hours. The mixture was allowed to cool before being poured portionwise into water (100 mL) over 70 minutes. The resultant solid was filtered off, washed with ice-cold water and dried in vacuo to give the title compound as a beige solid (1.28 g, 48%). $\delta_H$ (CDCl$_3$) 10.56 (s, 1H), 8.72 (s, 1H), 7.83 (dd, J 9, 12 Hz, 1H), 7.41 (t, J 12 Hz, 1H), 2.68 (d, J 3 Hz, 3H). LCMS (ES+) 242.1 (M+H)$^+$, RT 4.04 minutes (Method 3).

Intermediate 22

8-Ethyl-2-phenylquinoline-3-carboxaldehyde

The title compound was prepared in a similar manner to Intermediate 6, using 2-chloro-8-ethylquinoline-3-carboxaldehyde, and was obtained as a white solid (218 mg, 73%) after purification by column chromatography (SiO$_2$, 10% EtOAc in heptane). $\delta_H$ (CDCl$_3$) 10.23 (s, 1H), 8.81 (s, 1H), 7.85 (d, J 8.5 Hz, 1H), 7.70-7.78 (m, 3H), 7.50-7.62 (m, 4H), 3.37 (q, J 7.3 Hz, 2H), 1.41 (t, J 7.5 Hz, 3H). LCMS (ES+) 262.0 (M+H)$^+$, RT 4.55 minutes (Method 3).

Intermediate 23

8-Methyl-2-(pyridin-3-yl)quinoline-3-carboxaldehyde

The title compound was prepared in a similar manner to Intermediate 6, using 2-chloro-8-methylquinoline-3-carboxaldehyde, and was obtained as a white solid (261 mg, quantitative). $\delta_H$ (CDCl$_3$) 10.26 (s, 1H), 9.00 (d, J 2.1 Hz, 1H), 8.85 (s, 1H), 8.79 (dd, J 4.9, 1.7 Hz, 1H), 8.05-8.11 (m, 1H), 7.88 (d, J 8.1 Hz, 1H), 7.76 (d, J 7.2 Hz, 1H), 7.49-7.60 (m, 2H), 2.86 (s, 3H). LCMS (ES+) 249.0 (M+H)$^+$, RT 2.75 minutes (Method 3).

Intermediate 24

[8-Methyl-2-(3-thienyl)quinolin-3-yl]methanol

The title compound was prepared in a similar manner to Intermediate 4, using Intermediate 10, and was obtained as a white crystalline solid (306 mg, quantitative). $\delta_H$ (CDCl$_3$) 8.25 (s, 1H), 7.94-7.95 (m, 1H), 7.76-7.78 (m, 1H), 7.68 (d, J 12 Hz, 1H), 7.55 (d, J 9 Hz, 1H), 7.40-7.48 (m, 2H), 4.98 (d, J 9 Hz, 2H), 2.83 (s, 3H), 1.86 (t, J 9 Hz, 1H). LCMS (ES+) 256.1 (M+H)$^+$, RT 3.55 minutes (Method 3).

Intermediate 25

N-{2-[3-(Hydroxymethyl)-8-methylquinolin-2-yl]phenyl}acetamide

The title compound was prepared in a similar manner to Intermediate 4, using Intermediate 11, and was obtained as a yellow solid (343 mg, quantitative). $\delta_H$ (CDCl$_3$) 10.20 (br s, 1H), 8.52 (s, 1H), 8.38 (d, J 12 Hz, 1H), 7.78 (d, J 12 Hz, 1H), 7.63 (d, J 9 Hz, 1H), 7.40-7.58 (m, 3H), 7.18-7.30 (m, 1H), 4.88 (d, J 9 Hz, 2H), 2.83 (s, 3H), 2.02 (s, 3H), 1.91-1.96 (m, 1H). LCMS (ES+) 307.1 (M+H)$^+$, RT 2.70 minutes (Method 3).

Intermediate 26

{8-Methyl-2-[2-(trifluoromethoxy)phenyl]quinolin-3-yl}methanol

The title compound was prepared in a similar manner to Intermediate 4, using Intermediate 12, and was obtained as a colourless oil (341 mg, 99%). $\delta_H$ (CDCl$_3$) 8.30 (s, 1H), 7.67 (d, J 9 Hz, 1H), 7.54 (d, J 9 Hz, 1H), 7.35-7.50 (m, 5H), 4.60 (br s, 2H), 2.75 (s, 3H), 2.30 (br s, 1H). LCMS (ES+) 334.2 (M+H)$^+$, RT 4.14 minutes (Method 4).

Intermediate 27

[8-Methyl-2-(2-methylphenyl)quinolin-3-yl]methanol

The title compound was prepared in a similar manner to Intermediate 6, using (2-chloro-8-methylquinolin-3-yl)methanol, and was obtained as a white solid (206 mg, 33%) after purification by column chromatography (SiO$_2$, 5-20% EtOAc in heptane) followed by preparative HPLC (Method 1). $\delta_H$ (CDCl$_3$) 8.29 (s, 1H), 7.70-7.75 (m, 1H), 7.54-7.58 (m, 1H), 7.42-7.48 (m, 1H), 7.27-7.37 (m, 4H), 4.60 (d, J 5.3 Hz, 2H), 2.78 (s, 3H), 2.14 (s, 3H), 1.75 (t, J 5.8 Hz, 1H). LCMS (ES+) 264.16 (M+H)$^+$, RT 3.5 minutes (Method 3).

Intermediate 28

[2-(2-Ethylphenyl)-8-methylquinolin-3-yl]methanol

The title compound was prepared in a similar manner to Intermediate 4, using Intermediate 13, and was obtained as a clear oil (240 mg, 91%). $\delta_H$ (CDCl$_3$) 8.28, (s, 1H), 7.71 (d, J 8.1 Hz, 1H), 7.53-7.58 (m, 1H), 7.41-7.48 (m, 1H), 7.35-7.40 (m, 2H), 7.20-7.30 (m, 2H), 4.56 (d, J 5.1 Hz, 2H), 2.77 (s, 3H), 2.34-2.50 (m, 2H), 1.80 (t, J 5.8 Hz, 1H), 1.09 (t, J 7.5 Hz, 3H). LCMS (ES+) 278.2 (M+H)$^+$, RT 3.84 minutes (Method 3).

Intermediate 29

[6-Fluoro-2-(2-methylphenyl)quinolin-3-yl]methanol

A mixture of (2-chloro-6-fluoroquinolin-3-yl)methanol (200 mg, 0.95 mmol), K$_2$CO$_3$ (198 mg, 1.43 mmol) and o-tolylboronic acid (143 mg, 1.05 mmol) in DME (10 mL) and water (1 mL) was degassed by bubbling N$_2$ through it for 5 minutes. Pd(PPh$_3$)$_4$ (55 mg, 0.05 mmol) was added and the mixture heated in the microwave at 120° C. for 1 h. The solvent was removed in vacuo. Purification by column chromatography (SiO$_2$, 0-50% EtOAc in heptane) then by preparative HPLC (Method 1) gave the title compound (58 mg, 23%) as a white solid. $\delta_H$ (CDCl$_3$) 8.32 (s, 1H), 8.10-8.15 (m, 1H), 7.45-7.55 (m, 2H), 7.20-7.35 (m, 4H), 4.58 (s, 2H), 2.09 (s, 3H). LCMS (ES+) 268 (M+H)$^+$, RT 2.89 minutes (Method 3).

Intermediate 30

[8-Methyl-2-(1-methyl-1H-pyrazol-4-yl)quinolin-3-yl]methanol

The title compound was prepared in a similar manner to Intermediate 29, using (2-chloro-8-methylquinolin-3-yl)methanol, and was obtained as a white solid (134 mg, 44%) after purification by column chromatography (SiO$_2$, 0-100% EtOAc in heptane) and then by preparative HPLC (Method 1). $\delta_H$ (DMSO-d$_6$) 8.32 (s, 2H), 8.11 (s, 1H), 7.75-7.80 (m, 1H), 7.50-7.55 (m, 1H), 7.38-7.45 (m, 1H), 5.55-5.60 (t, J 5.5 Hz, 1H), 4.30-4.35 (m, 2H), 3.95 (s, 3H), 2.75 (s, 3H). LCMS (ES+) 254 (M+H)$^+$, RT 2.38 minutes (Method 3).

Intermediate 31

[2-(2-Isopropoxyphenyl)-8-methylquinolin-3-yl]methanol

The title compound was prepared in a similar manner to Intermediate 29, using (2-chloro-8-methylquinolin-3-yl)methanol, and was obtained as a clear, colourless oil (254 mg, 34%) after purification by column chromatography (SiO$_2$, 0-50% EtOAc in heptane) and then by preparative HPLC (Method 1). $\delta_H$ (CDCl$_3$) 8.24 (s, 1H), 7.71 (d, J 9 Hz, 1H), 7.55 (d, J 9 Hz, 1H), 7.38-7.50 (m, 3H), 7.15 (t, J 9 Hz, 1H), 7.04 (d, J 9 Hz, 1H), 4.20-4.95 (m, 2H), 4.38 (quin, J 6 Hz, 1H), 2.92 (br s, 1H), 2.80 (s, 3H), 1.19-1.29 (m, 3H), 0.92-1.00 (m, 3H). LCMS (ES+) 308.1 (M+H)$^+$, RT 3.50 minutes (Method 3).

Intermediate 32

[2-(2-Isopropylphenyl)-8-methylquinolin-3-yl]methanol

The title compound was prepared in a similar manner to Intermediate 29, using (2-chloro-8-methylquinolin-3-yl)methanol, and was obtained as a clear, colourless oil (394 mg, 56%) after purification by column chromatography (SiO$_2$, 5-40% EtOAc in heptane). $\delta_H$ (CDCl$_3$) 8.26 (s, 1H), 7.70 (d, J 9 Hz, 1H), 7.56 (d, J 9Hz, 1H), 7.35-7.50 (m, 3H), 7.22-7.29 (m, 1H), 7.15-7.20 (m, 1H), 4.45-4.65 (m, 2H), 2.77 (s, 3H), 2.59-2.70 (m, 1H), 1.91 (t, J 5.7 Hz, 1H), 1.16-1.23 (m, 3H), 1.07-1.14 (m, 3H). LCMS (ES+) 292.2 (M+H)$^+$, RT 4.12 minutes (Method 3).

Intermediate 33

[8-Methyl-2-(4-methylphenyl)quinolin-3-yl]methanol

The title compound was prepared in a similar manner to Intermediate 29, using (2-chloro-8-methylquinolin-3-yl)methanol, and was obtained as an off-white solid (89 mg, 28%) after purification by column chromatography (SiO$_2$, 0-50% EtOAc in heptane) and then by preparative HPLC (Method 1). $\delta_H$ (CDCl$_3$) 8.28 (s, 1H), 7.70 (d, J 7.9 Hz, 1H), 7.62 (d, J 8.1 Hz, 2H), 7.55-7.58 (m, 1H), 7.40-7.45 (m, 1H), 7.31 (d, J 7.9 Hz, 2H), 4.88 (d, J 5.7 Hz, 2H), 2.81 (s, 3H), 2.44 (s, 3H), 1.75-1.80 (m, 1H). LCMS (ES+) 264 (M+H)$^+$, RT 3.70 minutes (Method 3).

Intermediate 34

[8-Methyl-2-(3-methylphenyl)quinolin-3-yl]methanol

The title compound was prepared in a similar manner to Intermediate 29, using (2-chloro-8-methylquinolin-3-yl)methanol, and was obtained as an off-white solid (115 mg, 36%) after purification by column chromatography (SiO$_2$, 0-50% EtOAc in heptane) and then by preparative HPLC (Method 1). $\delta_H$ (CDCl$_3$) 8.27 (s, 1H), 7.65-7.70 (m, 1H), 7.52-7.57 (m, 1H), 7.35-7.50 (m, 4H), 7.20-7.25 (m, 1H), 4.82 (s, 2H), 2.82 (s, 3H), 2.44 (s, 3H). LCMS (ES+) 264 (M+H)$^+$, RT 3.73 minutes (Method 3).

Intermediate 35

[2-(Biphenyl-2-yl)-8-methylquinolin-3-yl]methanol

A mixture of (2-chloro-8-methylquinolin-3-yl)methanol (342 mg, 1.65 mmol), 2-biphenylboronic acid (392 mg, 1.98 mmol) and K$_3$PO$_4$ (399 mg, 1.88 mmol) in DME (4 mL) and water (1 mL) was degassed. Pd(PPh$_3$)$_4$ (95 mg, 0.08 mmol) was added, the mixture was degassed and heated in the microwave at 120° C. for 1 h. The reaction mixture was allowed to cool and extracted with EtOAc (150 mL). The organic layer was washed with water (50 mL), separated, dried (MgSO$_4$) and concentrated in vacuo. Purification by column chromatography (SiO$_2$, 0-100% EtOAc in heptane) gave the title compound (145 mg, 27%) as a white crystalline solid. $\delta_H$ (MeOD-d$_4$) 8.19 (s, 1H), 7.71 (d, J 8.1 Hz, 1H), 7.40-7.66 (m, 6H), 7.15-7.20 (m, 2H), 7.08-7.12 (m, 3H), 4.30-4.40 (br m, 1H), 4.11-4.22 (br m, 1H), 2.70 (s, 3H). LCMS (ES+) 326.3 (M+H)$^+$, RT 3.98 minutes (Method 3).

Intermediate 36

[8-Methyl-2-(1H-pyrazol-4-yl)quinolin-3-yl]methanol

The title compound was prepared in a similar manner to Intermediate 35, using (2-chloro-8-methylquinolin-3-yl)methanol, and was obtained as a white solid (67 mg, 23%) after purification by column chromatography (SiO$_2$, 0-100% EtOAc in heptane). $\delta_H$ (DMSO-d$_6$) 13.16 (br s, 1H), 8.32-8.35 (m, 2H), 8.17-8.19 (m, 1H), 7.25-7.80 (m, 1H), 7.54-7.59 (m, 1H), 7.40-7.45 (m, 1H), 5.54-5.60 (m, 1H), 4.79-4.82 (m, 2H), 2.74 (s, 3H). LCMS (ES+) 240.2, (M+H)$^+$, RT 2.06 minutes (Method 3).

Intermediate 37

[2-(2-Chlorophenyl)-8-methylquinolin-3-yl]methanol

The title compound was prepared in a similar manner to Intermediate 35, using (2-chloro-8-methylquinolin-3-yl)methanol, and was obtained as a clear, hard, yellow, glassy solid (282 mg, 83%) after purification by column chromatography (SiO$_2$, 0-100% EtOAc in heptane). $\delta_H$ (DMSO-d$_6$) 8.44 (s, 1H), 7.89-7.93 (m, 1H), 7.60-7.65 (m, 2H), 7.45-7.57 (m, 4H), 5.45 (t, J 5.3 Hz, 1H), 4.40 (br s, 2H), 2.66 (s, 3H). LCMS (ES+) 284.3, 286.2 (M+H)+, RT 3.68 minutes (Method 3).

Intermediate 38

{8-Methyl-2-[2-(trifluoromethyl)phenyl]quinolin-3-yl}methanol

The title compound was prepared in a similar manner to Intermediate 35, using (2-chloro-8-methylquinolin-3-yl) methanol, and was obtained as a clear, hard, glassy solid (305 mg, 80%) after purification by column chromatography (SiO$_2$, 0-100% EtOAc in heptane). $\delta_H$ (DMSO-d$_6$) 8.43 (s, 1H), 7.89-7.95 (m, 2H), 7.69-7.85 (m, 2H), 7.50-7.65 (m, 3H), 5.46 (t, J 5.3 Hz, 1H), 4.40-4.52 (br m, 1H), 4.22-4.32 (br m, 1H), 2.62 (s, 3H). LCMS (ES+) 318.2 (M+H)+, RT 3.81 minutes (Method 3).

Intermediate 39

[8-Methyl-2-(1,3-oxazol-2-yl)quinolin-3-yl]methanol

The title compound was prepared in a similar manner to Intermediate 4, using Intermediate 14, and was obtained as an off-white solid (101 mg, quantitative). $\delta_H$ (DMSO-d$_6$) 8.61 (s, 1H), 8.41 (s, 1H), 7.91 (d, J 7.7 Hz, 1H), 7.64-7.69 (m, 1H), 7.54-7.60 (m, 2H), 5.62 (t, J 5.7 Hz, 1H), 5.09-5.12 (m, 2H), 2.79 (s, 3H). LCMS (ES+) 241 (M+H)+, RT 3.22 minutes (Method 3).

Intermediate 40

[2-(3,5-Dimethylisoxazol-4-yl)-8-methylquinolin-3-yl]methanol

The title compound was prepared in a similar manner to Intermediate 4, using Intermediate 15, and was obtained as a pale cream gum (200 mg, quantitative). $\delta_H$ (MeOD-d$_4$) 8.45 (s, 1H), 7.81-7.85 (m, 1H), 7.61-7.65 (m, 1H), 7.49-7.56 (m, 1H), 4.63 (d, J 0.8 Hz, 2H), 2.77 (s, 3H), 2.36 (s, 3H), 2.20 (s, 3H). LCMS (ES+) 269 (M+H)+, RT 3.08 minutes (Method 3).

Intermediate 41

[2-(2,6-Difluorophenyl)-8-methylquinolin-3-yl]methanol

The title compound was prepared in a similar manner to Intermediate 35, using (2-chloro-8-methylquinolin-3-yl) methanol, and was obtained as a colourless glass (132 mg, 39%) after purification by column chromatography (SiO$_2$, 0-100% EtOAc in heptane) followed by preparative HPLC (Method 1). $\delta_H$ (CDCl$_3$) 8.38 (s, 1H), 7.74-7.79 (m, 1H), 7.58-7.62 (m, 1H), 7.39-7.54 (m, 3H), 7.04-7.10 (m, 2H), 4.74 (s, 2H), 2.81 (s, 3H). LCMS (ES+) 286.3 (M+H)+, RT 3.62 minutes (Method 3).

Intermediate 42

[2-(2-Fluoro-6-methoxyphenyl)-8-methylquinolin-3-yl]methanol

The title compound was prepared in a similar manner to Intermediate 4, using Intermediate 16, and was obtained as a colourless oil (123 mg, 93%). $\delta_H$ (CDCl$_3$) 8.30 (s, 1H), 7.70-7.76 (m, 1H), 7.53-7.57 (m, 1H), 7.33-7.49 (m, 2H), 6.81-6.90 (m, 2H), 4.53-4.58 (m, 2H), 3.76 (s, 3H), 2.80 (s, 3H), 1.96 (t, 1H). LCMS (ES+) 298.2 (M+H)+, RT 3.64 minutes (Method 4).

Intermediate 43

[8-Methyl-2-(pyridin-3-yl)quinolin-3-yl]methanol

The title compound was prepared in a similar manner to Intermediate 4, using Intermediate 23, and was obtained as a beige solid (138 mg, 92%). $\delta_H$ (CDCl$_3$) 9.01 (d, J 1.5 Hz, 1H), 8.70 (dd, J 4.7, 1.5 Hz, 1H), 8.36 (s, 1H), 8.12-8.18 (m, 1H), 7.73 (d, J 8.1 Hz, 1H), 7.60 (d, J 8.1 Hz, 1H), 7.41-7.52 (m, 2H), 4.89 (s, 2H), 2.82 (s, 3H). LCMS (ES+) 251.2 (M+H)+, RT 2.07 minutes (Method 3).

Intermediate 44

[8-Methyl-2-(2-thienyl)quinolin-3-yl]methanol

A mixture of 2-chloro-8-methylquinoline-3-carboxaldehyde (234 mg, 1.14 mmol), 2-thiopheneboronic acid (248 mg, 1.94 mmol), K$_2$CO$_3$ (315 mg, 2.28 mmol), palladium(II) acetate (10 mg, 0.045 mmol) and triphenylphosphine (48 mg, 0.182 mmol) in water (2 mL) was degassed. 1,4-Dioxane (6 mL) was added and the mixture further degassed, then heated at 115° C. for 2 h under microwave irradiation. The reaction mixture was filtered through Celite, washed with DCM and water and the filtrate was concentrated in vacuo. The residue was partitioned between DCM (100 mL) and H$_2$O (50 mL). The aqueous layer was re-extracted with DCM (50 mL) and the combined organic layers were dried (MgSO$_4$) and concentrated in vacuo. Purification by column chromatography (SiO$_2$, DCM) gave 8-methyl-2-(thien-2-yl)quinoline-3-carboxaldehyde (219 mg) as a yellow solid. This was dissolved in MeOH/DCM (6 mL/3 mL) and to it was added sodium borohydride (59 mg, 1.56 mmol). The reaction mixture was stirred at room temperature, quenched by the addition of glacial AcOH (0.1 mL) and the solvent removed in vacuo. The residue was partitioned between DCM (200 mL) and 5% aqueous Na$_2$CO$_3$ solution (40 mL). The aqueous layer was re-extracted with DCM (60 mL) and the combined organic layers were dried (MgSO$_4$) and concentrated in vacuo. Purification by column chromatography (SiO$_2$, 3% EtOAc in DCM) gave the title compound as a yellow solid (110 mg, 38%). $\delta_H$ (CDCl$_3$) 8.27 (s, 1H), 7.70 (d, J 6 Hz, 1H), 7.65 (d, J 12 Hz, 1H), 7.55 (d, J 12 Hz, 1H), 7.48 (d, J 9 Hz, 1H), 7.36-7.45 (m, 1H), 7.15-7.20 (m, 1H), 5.10 (d, J 5.8 Hz, 2H), 2.85 (s, 3H), 1.94 (t, J 12 Hz, 1H). LCMS (ES+) 256.2 (M+H)+, RT 4.06 minutes (Method 4).

Intermediate 45

(2-Chloro-5-fluoro-8-methylquinolin-3-yl)methanol

The title compound was prepared in a similar manner to Intermediate 4, using Intermediate 17, and was obtained as a beige solid (511 mg, 94%). $\delta_H$ (CDCl$_3$) 8.53 (s, 1H), 7.48 (td, J 7.2, 0.9 Hz, 1H), 7.13 (dd, J 9.6, 8.1 Hz, 1H), 4.95 (d, J 4.3 Hz, 2H), 2.71 (s, 3H), 2.13-2.19 (m, 1H). LCMS (ES+) 226.2, 228.2 (M+H)+, RT 3.49 minutes (Method 3).

Intermediate 46

(5-Fluoro-8-methyl-2-phenylquinolin-3-yl)methanol

The title compound was prepared in a similar manner to Intermediate 29, using Intermediate 45, and was obtained as a white solid (57 mg, 80%). $\delta_H$ (CDCl$_3$) 8.61 (s, 1H), 7.69-7.75 (m, 2H), 7.43-7.56 (m, 4H), 7.08-7.16 (m, 1H), 4.90 (dd, J 5.7, 0.8 Hz, 2H), 2.76 (s, 3H), 1.83 (t, J 5.7 Hz, 1H). LCMS (ES+) 268.2 (M+H)$^+$, RT 3.94 minutes (Method 3).

Intermediate 47

(6-Methyl-2-phenylquinolin-3-yl)methanol

The title compound was prepared in a similar manner to Intermediate 4, using Intermediate 18, and was obtained as a white solid (290 mg, 96%). $\delta_H$ (CDCl$_3$) 8.25 (s, 1H), 8.04 (d, J 8.5 Hz, 1H), 7.54-7.64 (m, 4H), 7.42-7.50 (m, 3H), 4.78 (d, J 4.3 Hz, 2H), 2.56 (s, 3H), 2.00-2.10 (m, 1H). LCMS (ES+) 250.2 (M+H)$^+$, RT 2.03 minutes (Method 3).

Intermediate 48

(6-Methoxy-2-phenylquinolin-3-yl)methanol

The title compound was prepared in a similar manner to Intermediate 6, using (2-chloro-6-methoxyquinolin-3-yl)methanol, and was obtained as a white solid (412 mg, 74%) after filtering off the precipitate. $\delta_H$ (DMSO-d$_6$) 8.39 (s, 1H), 7.92 (d, J 9.2 Hz, 1H), 7.61-7.66 (m, 2H), 7.44-7.52 (m, 4H), 7.34-7.40 (m, 1H), 5.47 (t, J 5.3 Hz, 1H), 4.61 (d, J 4.7 Hz, 2H), 3.90 (s, 3H). LCMS (ES+) 266.15 (M+H)$^+$, RT 2.06 minutes (Method 3).

Intermediate 49

[7-Fluoro-2-(2-methylphenyl)quinolin-3-yl]methanol

A mixture of 2-chloro-7-fluoroquinoline-3-carboxaldehyde (1 g, 4.8 mmol), K$_2$CO$_3$ (990 mg, 7.2 mmol) and o-tolylboronic acid (710 mg, 5.2 mmol) in DME (15 mL) and water (1.5 mL) was degassed by bubbling N$_2$ through it for 5 minutes. Pd(PPh$_3$)$_4$ (276 mg, 0.2 mmol) was added and the mixture heated in the microwave at 120° C. for 1 h. The reaction mixture was concentrated in vacuo and purified by column chromatography (SiO$_2$, 0-60% EtOAc in heptane) to give a yellow gum (1.04 g, 82%). To a solution of this gum (1 g, 3.77 mmol) in MeOH/DCM (15 mL/5 mL) was added sodium borohydride (186 mg, 1.18 mmol) and the mixture was stirred at r.t. for 1 h. The reaction was quenched by the addition of glacial AcOH (0.4 mL) and the solvent was removed in vacuo. The residue was partitioned between EtOAc (100 mL) and 10% aqueous Na$_2$CO$_3$ solution (30 mL). The organic layer was separated, dried (MgSO$_4$) and the solvent removed in vacuo. Purification by column chromatography (SiO$_2$, 0-50% EtOAc in heptane) then by preparative HPLC (Method 1) gave the title compound as a white solid (111 mg, 11%). $\delta_H$ (CDCl$_3$) 8.36 (s, 1H), 7.87-7.93 (m, 1H), 7.75-7.80 (m, 1H), 7.20-7.40 (m, 5H), 4.58 (d, J 5.7 Hz, 2H), 2.10 (s, 3H), 1.81 (m, J 9 Hz, 1H). LCMS (ES+) 268 (M+H)$^+$, RT 2.89 minutes (Method 3).

Intermediate 50

(7-Methyl-2-phenylquinolin-3-yl)methanol

The title compound was prepared in a similar manner to Intermediate 4, using Intermediate 19, and was obtained as a brown gum (420 mg, 95%). $\delta_H$ (CDCl$_3$) 8.29 (s, 1H), 7.93 (s, 1H), 7.75 (d, J 12 Hz, 1H), 7.55-7.60 (m, 2H), 7.41-7.50 (m, 3H), 7.39 (dd, J 8.3, 1.5 Hz, 1H), 4.77 (s, 2H), 2.57 (s, 3H). LCMS (ES+) 250.25 (M+H)$^+$, RT 3.14 minutes (Method 4).

Intermediate 51

[7-Methyl-2-(2-methylphenyl)quinolin-3-yl]methanol

The title compound was prepared in a similar manner to Intermediate 4, using Intermediate 20, and was obtained as a white gum (500 mg, 99%). $\delta_H$ (CDCl$_3$) 8.29 (s, 1H), 7.92 (s, 1H), 7.78 (d, J 8.3 Hz, 1H), 7.41 (dd, J 8.3, 1.5 Hz, 1H), 7.20-7.35 (m, 4H), 4.52 (s, 2H), 2.57 (s, 3H), 2.08 (s, 3H). LCMS (ES+) 264.26 (M+H)$^+$, RT 3.31 minutes (Method 4).

Intermediate 52

(2-Chloro-7-fluoro-8-methylquinolin-3-yl)methanol

The title compound was prepared in a similar manner to Intermediate 4, using Intermediate 21, and was obtained as a light beige crystalline solid (1.26 g, 98%). $\delta_H$ (DMSO-d$_6$) 8.40 (s, 1H), 7.92 (dd, J 9, 12 Hz, 1H), 7.45 (t, J 12 Hz, 1H), 5.61 (t, J 7.5 Hz, 1H), 4.58 (d, J 4.5 Hz, 2H), 2.45 (d, J 3 Hz, 3H). LCMS (ES+) 226.3 (M+H)$^+$, RT 3.41 minutes (Method 3).

Intermediate 53

(8-Ethyl-2-phenylquinolin-3-yl)-methanol

The title compound was prepared in a similar manner to Intermediate 4, using Intermediate 22, and was obtained as a white solid (208 mg, quantitative). $\delta_H$ (CDCl$_3$) 8.32 (s, 1H), 7.68-7.76 (m, 3H), 7.42-7.61 (m, H), 4.88 (d, J 5.8 Hz, 2H), 3.33 (q, J 7.5 Hz, 2H), 1.39 (t, J 7.5 Hz, 3H). LCMS (ES+) 264.0 (M+H)$^+$, RT 3.97 minutes (Method 3).

Intermediate 54

(8-Benzyl-2-chloroquinolin-3-yl)methanol

The title compound was prepared in a similar manner to Intermediate 4, using 8-benzyl-2-chloroquinoline-3-carboxaldehyde, and was obtained as a brown solid (482 mg, 48%). $\delta_H$ (CDCl$_3$) 8.24 (s, 1H), 7.65-7.71 (m, 1H), 7.40-7.50 (m, 2H), 7.15-7.35 (m, 5H), 4.92 (s, 2H), 4.60 (s, 2H). LCMS (ES+) 284/286 (M+H)$^+$, RT 4.03 minutes (Method 3).

Intermediate 55

1-(8-Methyl-2-phenylquinolin-3-yl)ethanol

To a solution of 8-methyl-2-phenylquinoline-3-carboxaldehyde (211 mg, 0.85 mmol) in THF (6 mL) cooled to −78° C. was added methyllithium (1.6N solution in ether, 0.6 mL, 0.93 mmol). After 1 h a further portion of methyllithium (0.2 mL, 0.32 mmol) was added. The reaction was allowed to warm to r.t. before being quenched with water (10 mL). The THF was removed in vacuo and the residue partitioned between DCM (100 mL) and water (30 mL). The organic layer was separated, dried (MgSO$_4$) and concentrated in vacuo. Purification by column chromatography (SiO$_2$, 5-25% EtOAc in heptane) gave the title compound as a white solid (145 mg, 65%). $\delta_H$ (CDCl$_3$) 8.42 (s, 1H), 7.70 (d, J 12 Hz, 1H), 7.60-7.63 (m, 2H), 7.42-7.55 (m, 5H), 5.23-5.31 (m, 1H), 2.80 (s, 3H), 1.87 (d, J 3.6 Hz, 1H), 1.47 (d, J 6.4 Hz, 3H). LCMS (ES+) 264.16 (M+H)+, RT 4.03 minutes (Method 4).

Intermediate 56

1-[8-Methyl-2-(pyridin-3-yl)quinolin-3-yl]ethanol

To a solution of Intermediate 23 (100 mg, 0.40 mmol) in THF (10 mL) under $N_2$ cooled to −78° C. was added methyllithium (1.6N solution in hexanes, 0.38 mL, 0.60 mmol) and the mixture was stirred at −78° C. for 45 minutes. After warming to r.t., the reaction was quenched by dropwise addition of water (1 mL). The mixture was partitioned between EtOAc (30 mL) and water (20 mL), and the aqueous layer extracted with EtOAc (30 mL). The combined organic layers were washed with water (30 mL), separated, dried ($MgSO_4$) and concentrated in vacuo. Purification by column chromatography ($SiO_2$, 5% MeOH in DCM) gave the title compound (90 mg, 84%) as an off-white solid. $\delta_H$ ($CDCl_3$) 8.89 (d, J 1.7 Hz, 1H), 8.69 (dd, J 4.9, 1.5 Hz, 1H), 8.48 (s, 1H), 7.99-8.05 (m, 1H), 7.74 (d, J 8.1 Hz, 1H), 7.55-7.61 (m, 1H), 7.41-7.51 (m, 2H), 5.24 (q, J 6.4 Hz, 1H), 2.79 (s, 3H), 1.52 (d, J 6.4 Hz, 3H). LCMS (ES+) 265.0 (M+H)+, RT 2.30 minutes (Method 3).

Intermediate 57

1-(8-Methyl-2-phenylquinolin-3-yl)propan-1-ol

The title compound was prepared in a similar manner to Intermediate 55, using 8-methyl-2-phenylquinoline-3-carboxaldehyde and ethyllithium (0.5N solution in ether, 4.6 mL, 2.3 mmol) and was obtained as a white solid (85 mg, 33%) after purification by column chromatography ($SiO_2$, 10-50% EtOAc in heptane). $\delta_H$ ($CDCl_3$) 8.35 (s, 1H), 7.66-7.72 (m, 1H), 7.40-7.62 (m, 7H), 4.96-5.04 (m, 1H), 2.80 (s, 3H), 1.97 (d, J 3.8 Hz, 1H), 1.60-1.70 (m, 2H), 0.84 (t, J 7.3 Hz, 3H). LCMS (ES+) 278 (M+H)+, RT 3.91 minutes (Method 3).

Intermediate 58

3-(Bromomethyl)-8-methyl-2-(thien-3-yl)quinoline

The title compound was prepared in a similar manner to Intermediate 5, using Intermediate 24, and was obtained as a yellow solid (359 mg, 96%). $\delta_H$ ($CDCl_3$) 8.35 (br s, 1H), 8.04-8.06 (m, 1H), 7.74-7.76 (m, 1H), 7.68 (d, J 9 Hz, 1H), 7.62 (d, J 9 Hz, 1H), 7.43-7.54 (m, 2H), 4.80 (s, 2H), 2.89 (br s, 3H). LCMS (ES+) 318.1, 320.1 (M+H)+, RT 4.75 minutes (Method 3).

Intermediate 59

N-{2-[3-(Bromomethyl)-8-methylquinolin-2-yl] phenyl}acetamide

The title compound was prepared in a similar manner to Intermediate 5, using Intermediate 25, and was obtained as a yellow oil (80 mg, 80%). $\delta_H$ ($CDCl_3$) 9.90 (m, 1H), 8.47 (s, 1H), 8.40 (d, J 9 Hz, 1H), 7.75 (d, J 9 Hz, 1H), 7.58-7.70 (m, 2H), 7.43-7.58 (m, 2H), 7.17-7.34 (m, 1H), 4.65 (s, 2H), 2.79 (s, 3H), 2.04 (s, 3H). LCMS (ES+) 369.1, 371.1 (M+H)+, RT 3.95 minutes (Method 3).

Intermediate 60

3-(Bromomethyl)-8-methyl-2-[2-(trifluoromethoxy) phenyl]quinoline

The title compound was prepared in a similar manner to Intermediate 5, using Intermediate 26, and was obtained as a pale yellow oil (186 mg, 88%). $\delta_H$ ($CDCl_3$) 8.30 (s, 1H), 7.40-7.75 (m, 7H), 4.35-4.70 (br m, 2H), 2.75 (s, 3H). LCMS (ES+) 396.1, 398.1 (M+H)+, RT 5.05 minutes (Method 4).

Intermediate 61

3-(Bromomethyl)-8-methyl-2-(2-methylphenyl) quinoline

The title compound was prepared in a similar manner to Intermediate 5, using Intermediate 27, and was obtained as a clear oil (195 mg, 76%). $\delta_H$ ($CDCl_3$) 8.30 (s, 1H), 7.70-7.75 (m, 1H), 7.55-7.60 (m, 1H), 7.30-7.50 (m, 5H), 4.49 (br s, 2H), 2.76 (s, 3H), 2.18 (s, 3H). LCMS (ES+) 326.0, 328.0 (M+H)+, RT 4.85 minutes (Method 3).

Intermediate 62

3-(Bromomethyl)-2-(2-ethylphenyl)-8-methylquinoline

The title compound was prepared in a similar manner to Intermediate 5, using Intermediate 28, and was obtained as a clear oil (107 mg, 73%). $\delta_H$ ($CDCl_3$) 8.30 (s, 1H), 7.66-7.71 (m, 1H), 7.55-7.60 (m, 1H), 7.47 (d, J 7.9 Hz, 1H), 7.39-7.44 (m, 2H), 7.28-7.38 (m, 2H), 4.32-4.58 (m, 2H), 2.76 (s, 3H), 2.35-2.55 (m, 2H), 1.12 (t, J 7.5 Hz, 3H). LCMS (ES+) 340.2, 342.1 (M+H)+, RT 5.02 minutes (Method 3).

Intermediate 63

3-(Bromomethyl)-2-(2-isopropoxyphenyl)-8-methylquinoline

The title compound was prepared in a similar manner to Intermediate 5, using Intermediate 31, and was obtained as a clear colourless oil (221 mg, quantitative). $\delta_H$ ($CDCl_3$) 8.27 (s, 1H), 7.69 (d, J 8.1 Hz, 1H), 7.38-7.56 (m, 4H), 7.13 (t, J 9 Hz, 1H), 7.00 (d, J 9 Hz, 1H), 4.53-4.76 (m, 2H), 4.38-4.50 (m, 1H), 2.68 (s, 3H), 1.24 (d, J 9 Hz, 3H), 1.04 (d, J 9 Hz, 3H). LCMS (ES+) 370.1, 372.1 (M+H)+, RT 4.90 minutes (Method 3).

Intermediate 64

3-(Bromomethyl)-2-(2-isopropylphenyl)-8-methylquinoline

The title compound was prepared in a similar manner to Intermediate 5, using Intermediate 32, and was obtained as a clear colourless oil (258 mg, 58%). $\delta_H$ ($CDCl_3$) 8.30 (s, 1H), 7.70 (d, J 9 Hz, 1H), 7.56-7.60 (m, 1H), 7.40-7.53 (m, 3H), 7.23-7.34 (m, 2H), 4.55 (d, J 9 Hz, 1H), 4.90 (d, J 9 Hz, 1H), 2.74 (s, 3H), 2.61-2.73 (m, 1H), 1.24 (d, J=9 Hz, 3H), 1.18 (d, J 9 Hz, 3H). LCMS (ES+) 354.2, 356.2 (M+H)+, RT 5.20 minutes (Method 3).

Intermediate 65

3-(Bromomethyl)-8-methyl-2-(4-methylphenyl) quinoline

The title compound was prepared in a similar manner to Intermediate 5, using Intermediate 33, and was obtained as a white solid (92 mg, 85%). $\delta_H$(CDCl$_3$) 8.31 (s, 1H), 7.65-7.75 (m, 3H), 7.50-7.63 (m, 1H), 7.40-7.45 (m, 1H), 7.30-7.35 (m, 2H), 4.72 (s, 2H), 2.81 (s, 3H), 2.47 (s, 3H). LCMS (ES+) 326.1, 328.1 (M+H)$^+$, RT 4.97 minutes (Method 3).

Intermediate 66

3-(Bromomethyl)-8-methyl-2-(3-methylphenyl) quinoline

The title compound was prepared in a similar manner to Intermediate 5, using Intermediate 34, and was obtained as a white solid (126 mg, 88%). $\delta_H$ (CDCl$_3$) 8.32 (m, 1H), 7.67-7.72 (m, 1H), 7.54-7.62 (m, 2H), 7.40-7.50 (m, 2H), 7.25-7.35 (m, 2H), 4.68 (s, 2H), 2.82 (s, 3H), 2.48 (s, 3H). LCMS (ES+) 326.2, 328.2 (M+H)$^+$, RT 4.95 minutes (Method 3).

Intermediate 67

2-(Biphenyl-2-yl)-3-(bromomethyl)-8-methylquinoline

The title compound was prepared in a similar manner to Intermediate 5, using Intermediate 35, and was obtained as a yellow solid (163 mg, 94%). $\delta_H$(MeOD-d$_4$) 9.07 (s, 1H), 8.07 (d, J 8.1 Hz, 1H), 7.70-7.94 (m, 6H), 7.18-7.28 (m, 5H), 4.65-4.70 (m, 1H), 4.47-4.51 (m, 1H), 2.64 (s, 3H). LCMS (ES+) 388.2, 390.2 (M+H)$^+$, RT 5.00 minutes (Method 3).

Intermediate 68

3-(Bromomethyl)-8-methyl-2-(1H-pyrazol-4-yl) quinoline

The title compound was prepared in a similar manner to Intermediate 5, using Intermediate 36, and was obtained as a sticky grey solid (75.5 mg, 89%). $\delta_G$(DMSO-d$_6$) 8.50 (s, 1H), 8.32-8.37 (m, 2H), 7.75-7.80 (m, 1H), 7.61-7.65 (m, 1H), 7.43-7.50 (m, 1H), 5.49 (br s, 1H), 5.11 (s, 2H), 2.75 (s, 3H). LCMS (ES+) 302.1, 304.1, (M+H)$^+$, RT 3.46 minutes (Method 3).

Intermediate 69

3-(Bromomethyl)-2-(2-chlorophenyl)-8-methylquinoline

The title compound was prepared in a similar manner to Intermediate 5, using Intermediate 37, and was obtained as a yellow, sticky, glassy solid (204 mg, quantitative). $\delta_H$ (CDCl$_3$) 8.61 (br s, 1H), 7.82-7.87 (m, 1H), 7.73-7.78 (m, 1H), 7.48-7.68 (m, 5H), 4.60-4.65 (m, 1H), 4.39-4.45 (m, 1H), 3.01 (br s, 3H). LCMS (ES+) 346.1, 348.1 (M+H)$^+$, RT 4.77 minutes (Method 3).

Intermediate 70

3-(Bromomethyl)-8-methyl-2-(1,3-oxazol-2-yl) quinoline

The title compound was prepared in a similar manner to Intermediate 5, using Intermediate 39, and was obtained as an off-white solid (81 mg, 64%). $\delta_H$ (DMSO-d$_6$) 8.65 (s, 1H), 8.45 (s, 1H), 7.88 (d, J 9 Hz, 1H), 7.74 (d, J 9 Hz, 1H), 7.60-7.68 (m, 2H), 5.50 (s, 2H), 2.78 (s, 3H). LCMS (ES+) 303.0, 305.0 (M+H)$^+$, RT 4.21 minutes (Method 3).

Intermediate 71

3-(Bromomethyl)-2-(3,5-dimethylisoxazol-4-yl)-8-methylquinoline

The title compound was prepared in a similar manner to Intermediate 5, using Intermediate 40, and was obtained as a yellow solid (186 mg, 75%). $\delta_H$ (CDCl$_3$) 8.38 (s, 1H), 7.72-7.77 (m, 1H), 7.63-7.67 (m, 1H), 7.51-7.58 (m, 1H), 4.54 (s, 2H), 2.84 (s, 3H), 2.41 (s, 3H), 2.25 (s, 3H). LCMS (ES+) 331.1, 333.1 (M+H)$^+$, RT 4.19 minutes (Method 3).

Intermediate 72

3-(Bromomethyl)-2-(2,6-difluorophenyl)-8-methylquinoline

The title compound was prepared in a similar manner to Intermediate 5, using Intermediate 41, and was obtained as a pale yellow solid (164 mg, quantitative). $\delta_H$ (CDCl$_3$) 8.30 (s, 1H), 7.72 (d, J 7.9 Hz, 1H), 7.58-7.63 (m, 1H), 7.41-7.53 (m, 2H), 7.03-7.12 (m, 2H), 4.54 (s, 2H), 2.79 (s, 3H). LCMS (ES+) 348.1, 350.1 (M+H)$^+$, RT 4.53 minutes (Method 3).

Intermediate 73

3-(Bromomethyl)-2-(2-fluoro-6-methoxyphenyl)-8-methylquinoline

The title compound was prepared in a similar manner to Intermediate 5, using Intermediate 42, and was obtained as a yellow solid (125 mg, 87%). $\delta_H$ (CDCl$_3$), 8.34 (br s, 1H), 7.70-7.75 (m, 1H), 7.55-7.62 (m, 1H), 7.39-7.56 (m, 2H), 6.81-6.95 (m, 2H), 4.50 (s, 2H), 3.80 (s, 3H), 2.83 (br s, 3H). LCMS (ES+) 360.1, 362.1 (M+H)$^+$, RT 4.56 minutes (Method 4).

Intermediate 74

3-(Bromomethyl)-8-methyl-2-(2-thienyl)quinoline

The title compound was prepared in a similar manner to Intermediate 5, using Intermediate 44, and was obtained as a yellow solid (134 mg, 99%). $\delta_H$ (CDCl$_3$) 8.47 (br s, 1H), 7.91 (d, J 6 Hz, 1H), 7.62-7.78 (m, 3H), 7.50-7.59 (m, 1H), 7.23-7.32 (m, 1H), 4.87 (s, 2H), 3.00 (s, 3H). LCMS (ES+) 318.0, 320.0 (M+H)$^+$, RT 5.04 minutes (Method 4).

Intermediate 75

3-(Bromomethyl)-5-fluoro-8-methyl-2-(2-methylphenyl)quinoline

A mixture of Intermediate 17 (270 mg, 1.21 mmol), K$_2$CO$_3$ (250 mg, 1.82 mmol) and o-tolylboronic acid (181 mg, 1.33 mmol) in DME (4 mL) and water (0.4 mL) was degassed by bubbling through N$_2$ for 5 minutes. Pd(PPh$_3$)$_4$ (70 mg, 0.06 mmol) was added and the mixture heated in the microwave at 120° C. for 1 h. The reaction mixture was concentrated in vacuo and purified by column chromatography (SiO$_2$, 0-50% EtOAc in heptane) to give a yellow oil (205 mg). To a solution of this oil in MeOH/DCM (6 mL/2 mL) was added sodium borohydride (36 mg, 0.96 mmol) and the reaction mixture was stirred at r.t. for 75 minutes. The reaction was quenched by the addition of glacial AcOH (0.2 mL) and the solvent removed in vacuo. The residue was partitioned between EtOAc (100 mL) and 10% aqueous $K_2CO_3$ solution (30 mL). The organic layer was separated, dried (MgSO$_4$) and the solvent removed in vacuo. Purification by column chromatography (SiO$_2$, 0-50% EtOAc in heptane) gave a clear oil (195 mg). To a solution of this oil (190 mg, 0.68 mmol) in DCM (8 mL) was added phosphorus tribromide (0.08 ml, 0.88 mmol) and the reaction mixture was stirred at r.t. for 75 minutes. The mixture was partitioned between DCM (100 mL) and 10% aqueous $K_2CO_3$ solution (30 mL). The organic layer was separated, dried (MgSO$_4$) and the solvent removed in vacuo to give the title compound as a clear oil (176 mg, 42%). $\delta_H$ (CDCl$_3$) 8.57 (s, 1H), 7.45-7.50 (m, 1H), 7.30-7.40 (m, 4H), 7.10-7.15 (m, 1H), 4.45-4.55 (br m, 2H), 2.69 (s, 3H), 2.18 (s, 3H). LCMS (ES+) 344.1, 346.1 (M+H)$^+$, RT 4.96 minutes (Method 3).

Intermediate 76

3-(Bromomethyl)-6-methyl-2-phenylquinoline

The title compound was prepared in a similar manner to Intermediate 5, using Intermediate 47, and was obtained as a yellow solid (122 mg, 89%). $\delta_H$ (CDCl$_3$) 8.30 (s, 1H), 8.13 (d, J 8.7 Hz, 1H), 7.68-7.74 (m, 2H), 7.58-7.64 (m, 2H), 7.48-7.56 (m, 3H), 4.63 (s, 2H), 2.57 (s, 3H). HPLC RT 4.2 minutes (Method 3).

Intermediate 77

3-(Bromomethyl)-6-fluoro-2-(2-methylphenyl)quinoline

The title compound was prepared in a similar manner to Intermediate 5, using Intermediate 29, and was obtained as a clear oil (43 mg, 63%) after purification by column chromatography (SiO$_2$, 0-50% EtOAc in heptane). $\delta_H$ (CDCl$_3$) 8.30 (s, 1H), 8.10-8.20 (m, 1H), 7.45-7.55 (m, 2H), 7.30-7.40 (m, 4H), 4.30-4.50 (br m, 2H), 2.14 (s, 3H). LCMS (ES+) 330.1, 332.1 (M+H)$^+$, RT 4.31 minutes (Method 3).

Intermediate 78

3-(Bromomethyl)-6-methoxy-2-phenylquinoline

The title compound was prepared in a similar manner to Intermediate 5, using Intermediate 48, and was obtained as a yellow oil (198 mg, 89%). $\delta_H$ (CDCl$_3$) 8.27 (s, 1H), 8.05-8.10 (m, 1H), 7.69-7.72 (m, 2H), 7.50-7.55 (m, 3H), 7.41 (dd, J 9.2, 2.6 Hz, 1H), 7.12 (d, J 2.6 Hz, 1H), 4.63 (s, 2H), 3.96 (s, 3H). HPLC RT 3.98 minutes (Method 3).

Intermediate 79

3-(Bromomethyl)-7-fluoro-2-(2-methylphenyl)quinoline

The title compound was prepared in a similar manner to Intermediate 5, using Intermediate 49, and was obtained as a yellow oil (135 mg, quantitative). $\delta_H$ (CDCl$_3$) 8.47 (s, 1H), 8.00-8.10 (br m, 1H), 7.90-8.00 (m, 1H), 7.30-7.50 (m, 5H), 4.40-4.50 (br m, 2H), 2.15 (s, 3H). LCMS (ES+) 330.1, 332.1 (M+H)$^+$, RT 4.31 minutes (Method 3).

Intermediate 80

3-(Bromomethyl)-7-methyl-2-phenylquinoline

The title compound was prepared in a similar manner to Intermediate 5, using Intermediate 50, and was obtained as an orange gum (157 mg, quantitative). $\delta_H$ (CDCl$_3$) 9.22 (s, 1H), 9.05 (s, 1H), 8.06 (d, J 8.5 Hz, 1H), 7.83-7.90 (m, 2H), 7.71 (dd, J 8.5, 1.0 Hz, 1H), 7.58-7.67 (m, 3H), 4.67 (s, 2H), 2.68 (s, 3H). LCMS (ES+) 312.1, 314.1 (M+H)$^+$, RT 4.12 minutes (Method 3).

Intermediate 81

3-(Bromomethyl)-7-methyl-2-(2-methylphenyl)quinoline

The title compound was prepared in a similar manner to Intermediate 5, using Intermediate 51, and was obtained as a white foam (139 mg, quantitative). $\delta_H$ (CDCl$_3$) 9.08 (br s, 2H), 8.11 (d, J 8.3 Hz, 1H), 7.74 (d, J 8.1 Hz, 1H), 7.47-7.55 (m, 1H), 7.30-7.47 (m, 3H), 4.47-4.54 (m, 2H), 2.67 (s, 3H), 2.28 (s, 3H). LCMS (ES+) 326.1, 328.1 (M+H)$^+$, RT 4.24 minutes (Method 3).

Intermediate 82

3-(Bromomethyl)-6-fluoro-7-methyl-2-(2-methylphenyl)quinoline

To a solution of Intermediate 52 (400 mg, 1.78 mmol) in DME (8 mL) and water (2 mL) was added potassium phosphate tribasic (431 mg, 2.03 mmol) and o-tolylboronic acid (242 mg, 1.78 mmol). The mixture was degassed before adding Pd(PPh$_3$)$_4$ (104 mg, 0.09 mmol), then heated in the microwave at 120° C. for 1 h. The mixture was partitioned between EtOAc (200 mL) and water (100 mL). The organic layer was washed with water (100 mL), separated, dried (MgSO$_4$) and the solvent removed in vacuo to give a yellow oil. Purification of the oil by column chromatography (SiO$_2$, 0-100% EtOAc in heptane) gave a pale yellow solid (410 mg). To a solution of the pale yellow solid (410 mg) in DCM (15 mL) was added phosphorus tribromide (0.27 mL, 2.91 mmol) and the mixture stirred at r.t. for 24 h. The mixture was partitioned between DCM (100 mL) and 10% aqueous $K_2CO_3$ solution (50 mL). The organic layer was separated, dried (MgSO$_4$) and the solvent removed in vacuo to give a yellow oil (419 mg, 69%). $\delta_H$ (CDCl$_3$) 8.38 (s, 1H), 7.73 (dd, J 9.0, 6.2 Hz, 1H), 7.33-7.45 (m, 5H), 4.38-4.56 (m, 2H), 2.72 (d, J 1.9 Hz, 3H), 2.18 (s, 3H). LCMS (ES+) 344.1, 346.1 (M+H)$^+$, RT 4.91 minutes (Method 3).

Intermediate 83

3-(1-Bromoethyl)-8-methyl-2-phenylquinoline

The title compound was prepared in a similar manner to Intermediate 5, using Intermediate 55, and was obtained as a yellow glass (55 mg, 56%). $\delta_H$ (CDCl$_3$) 8.57 (s, 1H), 7.70-7.78 (m, 3H), 7.46-7.61 (m, 5H), 5.46 (q, J 7 Hz, 1H), 2.84 (s, 3H), 2.08 (d, J=6.8 Hz, 3H). HPLC RT 4.9 minutes (Method 3).

Intermediate 84

3-(1-Bromoethyl)-8-methyl-2-(pyridin-3-yl)quinoline

The title compound was prepared in a similar manner to Intermediate 5, using Intermediate 56, and was obtained as a pale yellow solid (58 mg, 53%). $\delta_H$(CDCl$_3$) 9.19 (s, 1H), 8.97 (d, J 7.9 Hz, 1H), 8.91 (d, J 5.7 Hz, 1H), 8.58 (s, 1H), 8.14 (dd, J 7.9, 5.8 Hz, 1H), 7.77-7.84 (m, 1H), 7.66-7.72 (m, 1H), 7.55-7.64 (m, 1H), 5.19 (q, J 6.8 Hz, 1H), 2.77 (s, 3H), 2.21 (d, J 7.0 Hz, 3H). LCMS (ES+) 327.0, 329.0 (M+H)$^+$, RT 3.78 minutes (Method 3).

Intermediate 85

3-(1-Bromopropyl)-8-methyl-2-phenylquinoline

The title compound was prepared in a similar manner to Intermediate 5, using Intermediate 57, and was obtained as a yellow gum (321 mg, 76%). $\delta_H$(CDCl$_3$) 8.82 (s, 1H), 7.89 (d, J 7.7 Hz, 1H), 7.75-7.80 (m, 1H), 7.60-7.70 (m, 6H), 5.03-5.10 (m, 1H), 3.11 (s, 3H), 2.32-2.45 (m, 1H), 2.15-2.28 (m, 1H), 0.91-1.00 (m, 3H). LCMS (ES+) 340.1, 342.1 (M+H)$^+$, RT 5.12 minutes (Method 3).

Intermediate 86

3-(Chloromethyl)-8-methyl-2-phenylquinoline

To a solution of Intermediate 6 (640 mg, 2.57 mmol) in DCM (20 mL) under N$_2$ was added thionyl chloride (0.21 mL, 2.83 mmol) and the reaction mixture was stirred at r.t. for 1 h. The mixture was partitioned between DCM (100 mL) and water (40 mL). The aqueous layer was re-extracted with DCM (50 mL) and the combined organic layers were dried (MgSO$_4$) and the solvent removed in vacuo to give the title compound as an off-white solid (676 mg, 98%). $\delta_H$(CDCl$_3$) 8.33 (s, 1H), 7.70-7.80 (m, 3H), 7.45-7.60 (m, 5H), 4.78 (s, 2H), 2.82 (s, 3H). LCMS (ES+) 268.1, 270.1 (M+H)$^+$, RT 4.74 minutes (Method 3).

Intermediate 87

2-[(8-Methyl-2-phenylquinolin-3-yl)methyl]-1H-isoindole-1,3(2H)-dione

To a solution of Intermediate 86 (676 mg, 2.52 mmol) in DMF (10 mL) under N$_2$ was added phthalimide, potassium salt (514 mg, 2.77 mmol). The reaction mixture was stirred at r.t. for 18 h. The mixture was partitioned between EtOAc (150 mL) and water (30 mL). The organic layer was washed with water (5×30 mL), separated, dried (MgSO$_4$) and the solvent removed in vacuo to give the title compound as a white solid (950 mg, 99%). $\delta_H$ (DMSO-d$_6$) 8.23 (s, 1H), 7.87-7.92 (m, 4H), 7.76-7.85 (m, 1H), 7.70-7.75 (m, 2H), 7.45-7.60 (m, 5H), 4.95 (s, 2H), 2.70 (s, 3H). LCMS (ES+) 379.2 (M+H)$^+$, RT 4.51 minutes (Method 3).

Intermediate 88

3-(Aminomethyl)-8-methyl-2-phenylquinoline formate salt

To a solution of Intermediate 87 (700 mg, 1.85 mmol) in EtOH (100 mL) was added hydrazine monohydrate (187 mg, 3.7 mmol) and the reaction mixture was heated at reflux for 18 h. The mixture was filtered and concentrated in vacuo. Purification by preparative HPLC (Method 1) gave the title compound as an off-white solid (400 mg, 87%). $\delta_H$ (MeOD-d$_4$) 8.41 (s, 1H), 8.35 (s, 1H), 7.75-7.79 (m, 1H), 7.47-7.65 (m, 6H), 4.20 (s, 2H), 2.79 (s, 3H). LCMS (ES+) 249 (M+H)$^+$, RT 1.99 minutes (Method 3).

Intermediate 89

2-[1-(8-Methyl-2-phenylquinolin-3-yl)ethyl]-1H-isoindole-1,3(2H)-dione

The title compound was prepared in a similar manner to Intermediate 87, using Intermediate 83, and was obtained as a white solid (54 mg, 22%), after purification by preparative HPLC (Method 1). $\delta_H$(DMSO-d$_6$) 8.51 (s, 1H), 7.74 (d, J 8.1 Hz, 1H), 7.63-7.72 (m, 4H), 7.53-7.56 (m, 1H), 7.34-7.42 (m, 6H), 5.86 (q, J 7 Hz, 2H), 2.75 (s, 3H) 1.88 (d, J 7.2 Hz, 3H). LCMS (ES+) 393.2 (M+H)$^+$, RT 4.54 minutes (Method 3).

Intermediate 90

2-Chloro-3-(iodomethyl)-8-methylquinoline

To a solution of (2-chloro-8-methylquinolin-3-yl)methanol (2.0 g, 10 mmol) in DCM (200 mL) were added triphenylphosphine (2.6 g, 10 mmol), iodine (2.6 g, 10 mmol) and imidazole (0.7 g, 10 mmol) and the reaction mixture was stirred for 2 h at r.t. The mixture was washed with water (50 mL) and the organic layer was separated, dried and concentrated in vacuo. Purification by column chromatography (SiO$_2$, 50% Et$_2$O in heptane) gave the title compound as a brown solid (2.2 g, 72%). $\delta_H$(CDCl$_3$) 8.17 (s, 1H), 7.62 (d, J 9 Hz, 1H), 7.55 (d, J 9 Hz, 1H), 7.45 (t, J 9 Hz, 1H), 4.68 (s, 2H), 2.75 (s, 3H). LCMS (ES+) 318.0, 320.0 (M+H)$^+$, RT 4.53 minutes (Method 3).

Intermediate 91

3-(Azidomethyl)-2-chloro-8-methylquinoline

To a solution of Intermediate 90 (2.2 g, 6.9 mmol) in DMF (20 mL) was added sodium azide (0.6 g, 9.2 mmol) and the mixture was stirred at r.t. for 18 h. Water (100 mL) was added and the mixture was extracted with EtOAc (100 mL). The organic layer was washed with water (2×50 mL), separated, dried (MgSO$_4$) and concentrated in vacuo to give the title compound as a colourless solid (1.5 g, 93%). $\delta_H$(CDCl$_3$) 8.18 (s, 1H), 7.69 (d, J 9 Hz, 1H), 7.60 (d, J 9 Hz, 1H), 7.46 (t, J 9 Hz, 1H), 4.68 (s, 2H), 2.78 (s, 3H). LCMS (ES+) 233.1, 235.1 (M+H)$^+$, RT 4.28 minutes (Method 3).

Intermediate 92

3-[N-(tert-Butoxycarbonyl)aminomethyl]-2-chloro-8-methylquinoline

To a solution of Intermediate 91 (1.5 g, 6.4 mmol) in THF/water (30 mL/5 mL) was added triphenylphosphine (1.5 g, 5.7 mmol) and the mixture was stirred for 2 h at r.t., then heated at reflux for 1 h. The reaction mixture was allowed to cool to r.t. for the addition of di-tert-butyl dicarbonate (1.8 g, 8.3 mmol) to take place. The reaction mixture was stirred at r.t. for 18 h and concentrated in vacuo. Purification by column chromatography (SiO$_2$, 33% EtOAc in heptane) gave the title compound as a colourless solid (1.6 g, 81%). $\delta_H$(CDCl$_3$) 8.10 (s, 1H), 7.65 (d, J 9 Hz, 1H), 7.55 (d, J 9 Hz, 1H), 7.43 (t, J 9 Hz, 1H), 5.18 (br s, 1H), 4.55 (d, J 9 Hz, 2H), 2.78 (s, 3H), 1.45 (s, 9H). LCMS (ES+) 307.0, 309.0 (M+H)$^+$, RT 4.25 minutes (Method 3).

Intermediate 93

3-[N-(tert-Butoxycarbonyl)aminomethyl]-2-(3,5-dimethylisoxazol-4-yl)-8-methyl-quinoline To a solution of Intermediate 92 (100 mg, 3.25 mmol) in DME/water (2 mL/1 mL) was added 3,5-dimethylisoxazole-4-boronic acid (60 mg, 3.25 mmol) and potassium phosphate tribasic (100 mg, 4.72 mmol). The mixture was degassed by bubbling $N_2$ through it for 5 minutes before $PdCl_2(PPh_3)_2$ (20 mg, 0.03 mmol) was added and the mixture heated in a microwave at 130° C. for 1 h. The mixture was extracted with EtOAc (20 mL) and the organic layer was washed with water (10 mL), separated, dried ($MgSO_4$) and concentrated in vacuo. Purification by column chromatography ($SiO_2$, 50% EtOAc in heptane) gave the title compound as a colourless solid (60 mg, 48%). $\delta_H$ ($CDCl_3$) 8.15 (s, 1H), 7.70 (d, J 9 Hz, 1H), 7.57 (d, J 9 Hz, 1H), 7.48 (t, J 9 Hz, 1H), 4.80 (br s, 1H), 4.33 (d, J 9 Hz, 2H), 2.78 (s, 3H), 2.37 (s, 3H), 2.23 (s, 3H), 1.45 (s, 9H). LCMS (ES+) 368.2 (M+H)+, RT 3.99 minutes (Method 3).

Intermediate 94

8-Methoxy-2-oxo-1,2-dihydroquinoline-3-carboxylic acid methyl ester

To a solution/suspension of 2-amino-3-methoxybenzaldehyde (1.8 g, 11.9 mmol) in dry toluene (30 mL) under nitrogen was added acetic acid (0.1 mL) followed by dimethyl malonate (3.4 mL, 29.8 mmol) and piperidine (2.9 mL, 29.8 mmol). The reaction mixture was heated at reflux for 2 h. After cooling to r.t., the mixture was diluted with water (30 mL) and extracted with EtOAc (2×150 mL). The organic layer was separated, dried ($Na_2SO_4$), filtered and concentrated in vacuo. The residue was triturated in EtOAc/$Et_2O$ and the resulting solid was filtered off and dried in vacuo to give the title compound (1.7 g, 61%) as a pale yellow solid. $\delta_H$ (DMSO-$d_6$) 10.65 (br s, 1H), 8.52 (s, 1H), 7.42 (d, J 8.0 Hz, 1H), 7.27 (d, J 8.0 Hz, 1H), 7.21 (t, J 6.0 Hz, 1H), 3.94 (s, 3H), 3.84 (s, 3H). LCMS (ES+) 234 (M+H)+, RT 2.13 minutes (Method 5).

Intermediate 95

2-Chloro-8-methoxyquinoline-3-carboxylic acid methyl ester

A suspension of Intermediate 94 (1.7 g, 7.30 mmol) in phosphorus oxychloride (25 mL) was heated at reflux for 3 h. After cooling to r.t. the excess phosphorus oxychloride was removed in vacuo. The residue was treated cautiously with 2M NaOH solution and the resulting aqueous suspension was extracted with DCM (300 mL). The organic layer was separated, dried ($MgSO_4$), filtered and the solvent removed in vacuo. The resulting yellow solid was suspended/dissolved in dry toluene (40 mL) under nitrogen and to this mixture was added phosphorus oxychloride (1.6 mL, 17.2 mmol) and DIPEA (3.1 mL, 17.2 mmol). The mixture was heated at reflux for 4 h. The solvent was removed in vacuo and the residue dissolved in EtOAc (100 mL). This solution was poured into $NaHCO_3$ solution (100 mL) and extracted with EtOAc (100 mL). The combined organic layers were washed with $NaHCO_3$ solution (2×50 mL), washed with brine (50 mL), separated, dried ($MgSO_4$), filtered and the solvent removed in vacuo. Purification by column chromatography ($SiO_2$, 30% EtOAc in Petrol 40-60) afforded the title compound (1.16 g, 63%) as a white solid. $\delta_H$ ($CDCl_3$) 8.65 (s, 1H), 7.55 (t, J 8.0 Hz, 1H), 7.45 (dd, J 8.0, 0.8 Hz, 1H), 7.18 (dd, J 8.0, 0.8 Hz, 1H), 4.08 (s, 3H), 4.01 (s, 3H). LCMS (ES+) 252, 254 (M+H)+, RT 2.73 minutes (Method 5).

Intermediate 96

(2-Chloro-8-methoxyquinolin-3-yl)methanol

To a solution of Intermediate 95 (1.15 g, 4.56 mmol) in dry DCM (20 mL) under nitrogen cooled to 0° C. was added dropwise a solution of DIBAL-H (10 mL, 10 mmol, 1.0M in hexanes). The reaction mixture was stirred at 0° C. for 30 minutes and at r.t. for 30 minutes. The mixture was re-cooled to 0° C. and more DIBAL-H (5.0 mL, 5 mmol, 1.0M in hexanes) was added dropwise. Stirring continued at 0° C. for another 30 minutes. Saturated $Na_2SO_4$ solution (10 mL) was added to the mixture and the resulting gelatinous precipitate was filtered through celite and washed with DCM. The filtrate was collected, dried ($MgSO_4$), filtered and the solvent removed in vacuo. Purification by column chromatography ($SiO_2$, 40-60% EtOAc in Petrol 40-60) followed by trituration in DCM/$Et_2O$ afforded the title compound (180 mg, 18%) as a fawn solid. $\delta_H$ ($CDCl_3$) 8.26 (s, 1H), 7.49 (t, J 7.8 Hz, 1H), 7.41 (d, J 8.0 Hz, 1H), 7.08 (d, J 7.6 Hz, 1H), 4.94 (s, 2H), 4.07 (s, 3H). LCMS (ES+) 224, 226 (M+H)+, RT 2.21 minutes (Method 5).

Intermediate 97

(8-Methoxy-2-phenylquinolin-3-yl)methanol

To a solution/suspension of Intermediate 96 (260 mg, 1.16 mmol) in 1,4-dioxane/water (4 mL/1 mL) was added phenylboronic acid (155 mg, 1.28 mmol) and $K_2CO_3$ (240 mg, 1.74 mmol). The mixture was degassed before the addition of $Pd(PPh_3)_4$ (67 mg, 0.058 mmol) took place. Degassing was repeated and the mixture heated in a microwave at 120° C. for 1 h. Water (20 mL) was added and the mixture extracted with EtOAc (100 mL). The organic layer was washed with brine (20 mL), separated, dried ($MgSO_4$), filtered and the solvent removed in vacuo. Purification by column chromatography ($SiO_2$, 40-50% EtOAc in Petrol 40-60) afforded the title compound (190 mg, 62%) as an off-white solid. $\delta_H$ ($CDCl_3$) 8.33 (s, 1H), 7.62-7.64 (m, 2H), 7.39-7.50 (m, 5H), 7.06 (dd, J 7.2, 1.6 Hz, 1H), 4.82 (d, J 5.6 Hz, 2H), 4.06 (s, 3H), 1.84 (t, J 5.6 Hz, 1H). LCMS (ES+) 266 (M+H)+, RT 2.02 minutes (Method 5).

Intermediate 98

(8-Chloro-2-phenylquinolin-3-yl)methanol

The title compound was prepared in a similar manner to Intermediate 97, using (2,8-dichloroquinolin-3-yl)methanol, and was obtained as an off-white solid (440 mg, 93%) after purification by column chromatography ($SiO_2$, 40% EtOAc in Petrol 40-60). $\delta_H$ ($CDCl_3$) 8.40 (s, 1H), 7.69-7.84 (m, 4H), 7.40-7.53 (m, 4H), 4.88 (d, J 5.2 Hz, 2H), 1.87 (t, J 5.6 Hz, 1H). LCMS (ES+) 270, 272 (M+H)+, RT 3.05 minutes (Method 5).

Intermediate 99

1-(2-Chloro-8-methylquinolin-3-yl)ethanol

To a suspension of 2-chloro-8-methylquinoline-3-carboxaldehyde (10 g, 48.6 mmol) in dry THF (100 mL) under nitrogen cooled to −78° C. was added dropwise over 1 h methylmagnesium bromide (40 mL, 121.6 mmol, 3.0M solution in Et$_2$O). The reaction was allowed to warm to r.t. and stirred for a further 1 h before being poured slowly into NH$_4$Cl solution (100 mL). The mixture was extracted with EtOAc (2×200 mL) and the organic layers were combined, dried (MgSO$_4$), filtered and concentrated in vacuo to afford the title compound as an off-white solid (8.0 g, 74%). δ$_H$ (CDCl$_3$) 8.33 (s, 1H), 7.68 (d, J 8.0 Hz, 1H), 7.55 (d, J 7.2 Hz, 1H), 7.44 (t, J 7.6 Hz, 1H), 5.34-5.40 (m, 1H), 2.77 (s, 3H), 1.61 (d, J 6.4 Hz, 3H). LCMS (ES+) 222, 224 (M+H)$^+$, RT 3.01 minutes (Method 5).

Intermediate 100

1-(2-Chloro-8-methylquinolin-3-yl)ethanone

To a solution of Intermediate 99 (8.0 g, 36.1 mmol) in toluene (150 mL) was added manganese dioxide (31.4 g, 360.9 mmol). The reaction mixture was heated at 80° C. for 18 h. After cooling to r.t. the manganese dioxide was filtered off and washed with toluene. The filtrate was concentrated in vacuo to afford the title compound as a light yellow solid (6.25 g, 79%). δ$_H$ (CDCl$_3$) 8.35 (s, 1H), 7.72 (d, J 8.4 Hz, 1H), 7.66 (d, J 6.8 Hz, 1H), 7.50 (t, J 7.6 Hz, 1H), 2.78 (s, 3H), 2.77 (s, 3H). LCMS (ES+) 220, 222 (M+H)$^+$, RT 3.22 minutes (Method 5).

Intermediate 101

(S)-1-(2-Chloro-8-methylquinolin-3-yl)ethanol

To a solution of (R)-(+)-2-methyl-CBS-oxazaborolidine (378 mg, 1.36 mmol) in dry DCM (2 mL) under nitrogen was added borane-dimethyl sulphide complex (13.6 mL, 13.6 mmol, 1M solution in DCM) and the mixture was stirred at r.t. for 10 minutes. A solution of Intermediate 100 (3.0 g, 13.6 mmol) in dry DCM (12 mL) was added slowly over 2 h to this mixture. After standing overnight, 2 M HCl (50 mL) was added and the mixture extracted with DCM (200 mL). The organic layer was separated, dried (MgSO$_4$), filtered and concentrated in vacuo. The residue was recrystallised from isohexane to afford the title compound as a white solid (2.1 g, 70%). δ$_H$ (CDCl$_3$) 8.32 (s, 1H), 7.65 (d, J 8.0 Hz, 1H), 7.55 (dd, J 8.0, 1.2 Hz, 1H), 7.44 (dd, J 8.0, 7.2 Hz, 1H), 5.34-5.39 (m, 1H), 2.76 (s, 3H), 1.60 (d, J 6.4 Hz, 3H). LCMS (ES+) 222, 224 (M+H)$^+$, RT 3.02 minutes (Method 5).

Intermediate 102

(R)-2-Methylpropane-2-sulfinic acid 1-(2-chloro-8-methylquinolin-3-yl)-meth-(E)-ylideneamide To a solution of 2-chloro-8-methylquinoline-3-carboxaldehyde (2.05 g, 10 mmol) in dry THF (20 mL) under nitrogen was added titanium isopropoxide (5.68 g, 20 mmol) and the mixture stirred at r.t. for 10 minutes. (R)-(+)-2-Methyl-2-propanesulfinamide (1.21 g, 10 mmol) was added to the reaction which was stirred at r.t. for 72 h. Water (20 mL) was added and the mixture was extracted with DCM (150 mL). The organic layer was separated, dried (MgSO$_4$), filtered and the solvent removed in vacuo to afford the title compound as a pale yellow solid (2.4 g, 72%). δ$_H$(CDCl$_3$) 9.12 (s, 1H), 8.79 (s, 1H), 7.78 (d, J 8.4 Hz, 1H), 7.67 (d, J 6.8 Hz, 1H), 7.51 (t, J 7.8 Hz, 1H), 2.79 (s, 3H), 1.32 (s, 9H). LCMS (ES+) 309, 311 (M+H)$^+$, RT 3.66 minutes (Method 5).

Intermediate 103

(R)-2-Methylpropane-2-sulfinic acid [(S)-1-(2-chloro-8-methylquinolin-3-yl)ethyl]amide To a solution of Intermediate 102 (1.9 g, 6.15 mmol) in dry DCM (40 mL) under nitrogen cooled to −78° C. was added dropwise over 10 minutes a solution of methyl-magnesium bromide (4.1 mL, 12.3 mmol, 3.0M in DCM). The reaction mixture was allowed to warm to r.t. and stirred for 18 h. Saturated NH$_4$Cl solution (50 mL) was added and the aqueous layer was extracted with DCM (100 mL). The organic layers were combined, dried (MgSO$_4$), filtered and concentrated in vacuo to give a yellow oil. This was crystallised from petrol 40-60 to afford the title compound as a pale yellow solid (900 mg, 45%). δ$_H$ (CDCl$_3$) 8.17 (s, 1H), 7.64 (d, J 8.0 Hz, 1H), 7.56 (d, J 7.2 Hz, 1H), 7.45 (t, J 7.6 Hz, 1H), 5.09-5.12 (m, 1H), 3.44 (d, J 4.8 Hz, 1H), 2.77 (s, 3H), 1.71 (d, J 6.8 Hz, 3H), 1.25 (s, 9H). LCMS (ES+) 325, 327 (M+H)$^+$, RT 3.19 minutes (Method 5).

Intermediate 104

(S)-1-(2-Chloro-8-methylquinolin-3-yl)ethylamine

To a solution of Intermediate 103 (0.25 g, 0.77 mmol) in MeOH (2 mL) was added conc. HCl (1 mL) and the mixture stirred at r.t. for 2 hours. The reaction was poured into DCM (100 mL) and washed with 2M NaOH solution (50 mL). The organic layer was separated, dried (MgSO$_4$), filtered and the solvent removed in vacuo to afford the title compound as a white solid (0.16 g, 94%). δ$_H$ (CDCl$_3$) 8.29 (s, 1H), 7.66 (d, J 8.4 Hz, 1H), 7.53 (d, J 6.8 Hz, 1H), 7.41-7.45 (m, 1H), 4.61-4.67 (m, 1H), 2.76 (s, 3H), 1.50 (d, J 4.0 Hz, 3H). LCMS (ES+) 221, 223 (M+H)$^+$, RT 2.96 minutes (Method 6).

Intermediate 105

[(S)-1-(2-Chloro-8-methylquinolin-3-yl)ethyl]carbamic acid tert-butyl ester

To a solution of Intermediate 104 (1.83 g, 3.11 mmol) in dry DCM (10 mL) under nitrogen was added DIPEA (2.7 mL, 15.6 mL) followed by a solution of di-tert-butyl dicarbonate in DCM (10 mL) dropwise. The reaction mixture was stirred at r.t. for 3 h, then diluted with DCM (10 mL) and washed with saturated NaHCO$_3$ solution (15 mL) and brine (15 mL). The organic layer was separated, dried (Na$_2$SO$_4$), filtered and the solvent removed in vacuo. Purification by column chromatography (SiO$_2$, 0-30% EtOAc in Petrol 40-60) afforded the title compound as a white solid (897 mg, 34%). δ$_H$ (CDCl$_3$) 8.07 (s, 1H), 7.64 (d, J 8.0 Hz, 1H), 7.54 (d, J 7.2 Hz, 1H), 7.43 (t, J 7.6 Hz, 1H), 5.12-5.22 (m, 1H), 5.00-5.10 (m, 1H), 2.76 (s, 3H), 1.50-1.57 (m, 3H), 1.30-1.50 (m, 9H). LCMS (ES+) 321, 323 (M+H)$^+$, RT 3.58 minutes (Method 5).

Intermediate 106

3-(Hydroxymethyl)-2-phenylquinoline-8-carbonitrile

To a solution of Intermediate 98 (200 mg, 0.74 mmol) in DMF (3 mL) was added one drop of water followed by zinc cyanide (261 mg, 2.23 mmol), tris(dibenzylidene-acetone) dipalladium(0) (27 mg, 0.03 mmol) and 2-dicyclohexylphosphino-2',6'-dimethoxy-1,1'-biphenyl (27 mg, 0.067 mmol). The reaction mixture was degassed and heated in a microwave at 150° C. for 1 h. Water (5 mL) was added and the mixture was extracted with EtOAc (40 mL). The organic layer was washed with water (5 mL), washed with brine (5 mL), separated, dried (MgSO$_4$), filtered and the solvent removed in vacuo. Purification by column chromatography (SiO$_2$, 30-50% EtOAc in Petrol 40-60) afforded the title compound (42 mg, 22%) as an off-white solid. δ$_H$ (CDCl$_3$) 8.49 (s, 1H), 8.10-8.13 (m, 2H), 7.73-7.76 (m, 2H), 7.61 (dd, J 8.0, 7.2 Hz, 1H), 7.49-7.54 (m, 3H), 4.95 (d, J 4.4 Hz, 2H), 1.96 (t, J 5.4 Hz, 1H). LCMS (ES+) 261 (M+H)$^+$, RT 2.79 minutes (Method 5).

Intermediate 107

[2-(3-Methoxyphenyl)-8-methylquinolin-3-yl]methanol

To a solution of (2-chloro-8-methylquinolin-3-yl)methanol (300 mg, 1.45 mmol) in 1,4-dioxane/water (4 mL/1 mL) was added 3-methoxyphenylboronic acid (261 mg, 1.74 mmol), K$_2$CO$_3$ (400 mg, 2.9 mmol) and Pd(PPh$_3$)$_4$ (167 mg, 0.145 mmol). The mixture was degassed and heated in a microwave at 150° C. for 1 h. The solvent was removed in vacuo and the residue dissolved in DCM (50 mL) and washed with water (2×10 mL). The organic layer was separated, dried (MgSO$_4$), filtered and the solvent removed in vacuo. Purification by column chromatography (SiO$_2$, 10-20% EtOAc in Petrol 40-60) yielded the title compound (306 mg, 76%) as a colourless gum. δ$_H$ (CDCl$_3$) 8.25 (s, 1H), 7.66 (d, J 8.2 Hz, 1H), 7.54 (d, J 7.1 Hz, 1H), 7.32-7.45 (m, 2H), 7.21-7.26 (m, 2H), 6.96-7.00 (m, 1H), 4.79 (s, 2H), 3.85 (s, 3H), 2.81 (s, 3H), 2.06 (s, 1H). LCMS (ES+) 280 (M+H)$^+$, RT 3.03 minutes (Method 5).

Intermediate 108

(S)-1-(8-Methyl-2-phenylquinolin-3-yl)ethanol

The title compound was prepared in a similar manner to Intermediate 107, using Intermediate 101, and was obtained as a clear gum (94 mg, 80%) after purification by column chromatography (SiO$_2$, 20% EtOAc in Et$_2$O). δ$_H$ (CDCl$_3$) 8.32 (s, 1H), 7.62 (d, J=8.4 Hz, 1H), 7.50-7.55 (m, 2H), 7.33-7.49 (m, 5H), 5.19 (q, J 6.4 Hz, 1H), 2.70 (s, 3H), 1.96 (br s, 1H), 1.39 (d, J 6.4 Hz, 3H). LCMS (ES+) 264 (M+H)$^+$, RT 3.04 minutes (Method 5).

Intermediate 109

(S)-1-[8-Methyl-2-(pyridin-3-yl)quinolin-3-yl]ethanol

The title compound was prepared in a similar manner to Intermediate 107, using Intermediate 101, and was obtained as a pale yellow gum (81 mg, 68%) after purification by column chromatography (SiO$_2$, 20% EtOAc in Et$_2$O). δ$_H$ (CDCl$_3$) 8.92 (s, 1H), 8.70 (d, J 6.2 Hz, 1H), 8.45 (s, 1H), 8.02 (d, J 8.4 Hz, 1H), 7.69 (d, J 6.2 Hz, 1H), 7.58 (d, J=6.2 Hz, 1H), 7.51 (d, J 8.4 Hz, 1H), 7.48 (t, J 8.4 Hz, 1H), 5.25 (q, J 6.4 Hz, 1H), 2.85 (s, 3H), 1.85 (br s, 1H), 1.50 (d, J 6.4 Hz, 3H). LCMS (ES+) 265 (M+H)$^+$, RT 2.15 minutes (Method 5).

Intermediate 110

4-Chloro-N-(4-methoxybenzyl)-6-methyl-1,3,5-triazin-2-amine

To a solution of cyanuric chloride (3.69 g, 20 mmol) in DCM (100 mL) at −10° C. was added methylmagnesium bromide (20 mL, 60 mmol, 3.0M solution in ether) maintaining the temperature at −10° C. The reaction was stirred for 4 h at −10° C. and then quenched with saturated ammonium chloride solution (20 mL). The organic layer was separated, dried (MgSO$_4$) and filtered. The filtrate was cooled to 0° C. before the addition of 4-methoxybenzylamine (2.74 g, 20 mmol) and DIPEA (2.6 g, 20 mmol) took place. The reaction was stirred for 18 h at r.t. The organic layer was washed with water (2×20 mL), separated, dried (MgSO$_4$), filtered and the solvent removed in vacuo. The residue was crystallised from diisopropyl ether affording the title compound as a pale yellow solid (2.8 g, 51%). δ$_H$ (CDCl$_3$) 7.23 (d, J 9.2 Hz, 2H), 6.85 (d, J 9.2 Hz, 2H), 5.62 (br s, 1H), 4.56 (d, J 8.1 Hz, 2H), 3.79 (s, 3H), 2.38 (s, 3H). LCMS (ES+) 265 (M+H)$^+$, RT 2.80 minutes (Method 5).

Example 1

3-[(5-Methyl-3-phenylquinoxalin-2-yl)methyl]-3H-purin-6-amine, formic acid salt

A mixture of 3-bromo-1-phenylpropane-1,2-dione (1.0 g, 4.42 mmol), adenine (590 mg, 4.42 mmol) and 2,3-diaminotoluene (540 mg, 4.42 mmol) in EtOH (20 mL) was heated at 60° C. for 4 h. After cooling, the reaction mixture was partitioned between EtOAc and water. The organic phase was dried (MgSO$_4$) and concentrated in vacuo. The residue was purified by preparative HPLC (Method 1) to give the title compound (23 mg, 14%) as an off-white solid. δ$_H$ (DMSO-d$_6$) 8.46 (s, 1H), 7.88-8.05 (m, 4H), 7.59-7.72 (m, 6H), 7.53 (s, 1H), 5.94 (s, 2H), 2.74 (s, 3H). LCMS (ES+) 368.2 (M+H)$^+$, RT 2.15 minutes (Method 3).

Example 2

2-Phenyl-3-[(7H-purin-6-ylthio)methyl]quinoxaline

A mixture of Intermediate 1 (200 mg, 0.67 mmol) and 6-mercaptopurine (103 mg, 0.61 mmol) in 2N aqueous NaOH solution (4 mL) was stirred at r.t. for 2 h. DMF was added until a clear solution was obtained and stirring continued for 3 h. The reaction mixture was allowed to stand for 3 days, then adjusted to pH 5 with glacial AcOH. The precipitate was filtered off, washed sparingly with DCM and dried in vacuo to give the title compound (138 mg, 56%) as a pale yellow solid. δ$_H$ (DMSO-d$_6$) 13.45 (br. s, 1H), 8.50 (s, 1H), 8.41 (s, 1H), 8.06-8.17 (m, 2H), 7.77-7.91 (m, 4H), 7.49-7.61 (m, 3H), 5.05 (s, 2H). LCMS (ES+) 371.1 (M+H)$^+$, RT 2.95 minutes (Method 3).

Example 3

2-[(7H-Purin-6-ylthio)methyl]-3-[3-(trifluoromethyl)phenyl]quinoxaline

A solution of Intermediate 3 (80 mg, 0.22 mmol) and 6-mercaptopurine (37 mg, 0.22 mmol) in 2N aqueous NaOH solution (2 mL) and DMF (4 mL) was stirred at r.t. for 2.5 h. The mixture was adjusted to pH 5 with glacial AcOH and the solvent was removed in vacuo. The residue was suspended in water (10 mL) and filtered. The solid was washed sparingly with DCM and dried in vacuo to give the title compound (35 mg, 37%) as a white solid. δ$_H$ (DMSO-d$_6$) 8.45 (s, 1H), 8.33 (s, 1H), 7.99-8.18 (m, 4H), 7.83-7.93 (m, 2H), 7.63-7.78 (m, 2H), 5.10 (s, 2H). LCMS (ES+) 439.2 (M+H)$^+$, RT 3.43 minutes (Method 3).

Example 4

2-Phenyl-3-[7H-purin-6-ylthio)methyl]quinoline

A solution of Intermediate 5 (113 mg, 0.37 mmol) in DMF (2 mL) was added to a suspension of 6-mercaptopurine (64 mg, 0.37 mmol) in DMF (1 mL) and the solution was stirred at r.t. for 17.5 h. The reaction mixture was purified by preparative HPLC (Method 1) to give the title compound (75 mg, 54%) as a white solid. $\delta_H$ (DMSO-d$_6$) 8.63 (s, 1H), 8.61 (s, 1H), 8.40 (s, 1H), 7.96-8.04 (m, 2H), 7.72-7.79 (m, 1H), 7.66-7.71 (m, 2H), 7.56-7.64 (m, 1H), 7.46-7.55 (m, 3H), 4.82 (s, 2H). LCMS (ES+) 370.0 (M+H)$^+$, RT 2.52 minutes (Method 3).

Example 5

8-Methyl-2-phenyl-3-[(7H-purin-6-ylthio)methyl]quinoline

To a solution of Intermediate 7 (62 mg, 0.20 mmol) in DMF (0.5 mL) was added a suspension of 6-mercaptopurine (34 mg, 0.20 mmol) in DMF (2 mL) and the solution was stirred at r.t. for 16.5 h. The solvent was removed in vacuo and the residue purified by preparative HPLC (Method 1) to give the title compound (39 mg, 51%) as a white solid. $\delta_H$ (CDCl$_3$) 8.66 (s, 1H), 8.43 (s, 1H), 8.09 (s, 1H), 7.72-7.78 (m, 2H), 7.60-7.66 (m, 1H), 7.38-7.56 (m, 5H), 4.84 (s, 2H), 2.79 (s, 3H). LCMS (ES+) 384.1 (M+H)$^+$, RT 3.91 minutes (Method 3).

Example 6

4-Methyl-6-[(8-methyl-2-phenylquinolin-3-yl)methoxy]pyrimidin-2-amine, acetic acid salt A mixture of Intermediate 6 (50 mg, 0.2 mmol), 2-amino-4-chloro-6-methylpyrimidine (29 mg, 0.2 mmol) and sodium hydride (60% in mineral oil, 8 mg, 0.2 mmol) in DMF (2.0 mL) was stirred at r.t. overnight. The solvent was removed in vacuo and the residue was treated with water, concentrated in vacuo and purified by preparative HPLC (Method 1) to give the title compound (29 mg, 34%) as an off-white solid. $\delta_H$ (CDCl$_3$) 8.30 (s, 1H), 7.67-7.77 (m, 3H), 7.55-7.60 (m, 1H), 7.41-7.54 (m, 4H), 6.01 (s, 1H), 5.47 (s, 2H), 5.14 (s, 2H), 2.83 (s, 3H), 2.26 (s, 3H), 2.00 (s, 3H). LCMS (ES+) 357.1 (M+H)$^+$, RT 4.38 minutes (Method 3).

Example 7

2-(2-Methylphenyl)-3-[(7H-purin-6-ylthio)methyl]quinoline

The title compound was prepared in a similar manner to Example 4, using Intermediate 9, and was obtained as a white solid (66%) after purification by preparative HPLC (Method 1). $\delta_H$ (DMSO-d$_6$) 13.51 (br. s, 1H), 8.62 (s, 1H), 8.61 (s, 1H), 8.42 (s, 1H), 7.95-8.04 (m, 2H), 7.73-7.80 (m, 1H), 7.58-7.65 (m, 1H), 7.23-7.37 (m, 4H), 4.60 (br. s, 2H), 2.09 (s, 3H). LCMS (ES+) 384.1 (M+H)$^+$, RT 3.19 minutes (Method 3).

Example 8

8-Methyl-3-[(7H-purin-6-ylthio)methyl]-2-(thien-3-yl)quinoline

The title compound was prepared in a similar manner to Example 4, using Intermediate 58, and was obtained as an off-white powder (98 mg, 79%) after purification by preparative HPLC (Method 1). $\delta_H$ (CDCl$_3$) 8.77 (s, 1H), 8.41 (s, 1H), 8.13 (s, 1H), 8.09 (s, 1H), 7.84-7.89 (m, 1H), 7.66-7.70 (m, 1H), 7.60-7.64 (m, 1H), 7.50-7.55 (m, 1H), 7.38-7.50 (m, 2H), 5.00 (s, 2H), 2.82 (s, 3H). LCMS (ES+) 390.1 (M+H)$^+$, RT 3.68 minutes (Method 3).

Example 9

2-(2-Acetamidophenyl)-8-methyl-3-[(7H-purin-6-ylthio)methyl]quinoline

The title compound was prepared in a similar manner to Example 4, using Intermediate 59, and was obtained as a pale cream solid (82 mg, 82%) after purification by preparative HPLC (Method 1). $\delta_H$ (MeOD-d$_4$) 8.62 (br s, 1H), 8.55 (s, 1H), 8.32 (br s, 1H), 7.85 (d, J 9 Hz, 1H), 7.75 (d, J 9 Hz, 1H), 7.54-7.62 (m, 2H), 7.40-7.50 (m, 2H), 7.30 (t, J 9 Hz, 1H), 4.79 (s, 2H), 2.77 (s, 3H), 1.93 (s, 3H). LCMS (ES+) 441.1 (M+H)$^+$, RT 3.02 minutes (Method 3).

Example 10

8-Methyl-3-[(7H-purin-6-ylthio)methyl]-2-[2-(trifluoromethoxy)phenyl]quinoline The title compound was prepared in a similar manner to Example 4, using Intermediate 60, and was obtained as a white solid (195 mg, 90%) after purification by column chromatography (SiO$_2$, 94:5:1 DCM/MeOH/7M ammonia solution in MeOH). $\delta_H$ (CDCl$_3$) 11.50 (br s, 1H), 8.70 (s, 1H), 8.45 (s, 1H), 8.10 (s, 1H), 7.60-7.70 (m, 2H), 7.50-7.55 (m, 1H), 7.35-7.50 (m, 4H), 4.75-4.90 (m, 1H), 4.50-4.65 (m, 1H), 2.80 (s, 3H). LCMS (ES+) 468.1 (M+H)$^+$, RT 4.13 minutes (Method 4).

Example 11

8-Methyl-2-(2-methylphenyl)-3-[7H-purin-6-ylthio)methyl]quinoline, acetic acid salt The title compound was prepared in a similar manner to Example 4, using Intermediate 61, and was obtained as a white solid (41 mg, 34%) after purification by preparative HPLC (Method 2). $\delta_H$ (DMSO-d$_6$) 8.58 (s, 1H), 8.57 (s, 1H), 8.30 (s, 1H), 7.79-7.83 (m, 1H), 7.60 (d, J 9 Hz, 1H), 7.47 (t, J 9 Hz, 1H), 7.30-7.40 (m, 4H), 4.60 (br s, 2H), 2.64 (s, 3H), 2.13 (s, 3H) 1.74 (s, 3H). LCMS (ES+) 398.1 (M+H)$^+$, RT 3.96 minutes (Method 4).

Example 12

2-(2-Ethylphenyl)-8-methyl-3-[(7H-purin-6-ylthio)methyl]quinoline

The title compound was prepared in a similar manner to Example 4, using Intermediate 62, and was obtained as a white solid (40 mg, 31%) after purification by preparative HPLC (Method 1) and partitioning between DCM (30 mL) and 10% K$_2$CO$_3$ solution (20 mL). $\delta_H$ (CDCl$_3$) 11.74 (br s, 1H), 8.69 (br s, 1H), 8.43 (s, 1H), 8.09 (s, 1H), 7.61-7.66 (m, 1H), 7.52-7.56 (m, 1H), 7.30-7.44 (m, 5H), 4.40-4.80 (m, 2H), 2.75 (s, 3H), 2.35-2.64 (m, 2H), 1.44 (t, J 7.5 Hz), 3H). LCMS (ES+) 412.2 (M+H)$^+$, RT 3.99 minutes (Method 3).

Example 13

8-Methyl-2-(1-methyl-1H-pyrazol-4-yl)-3-[(7H-purin-6-ylthio)methyl]quinoline

Phosphorus tribromide (0.06 mL, 0.67 mmol) was added to a solution of Intermediate 30 (130 mg, 0.51 mmol) in DCM (6 mL) and the reaction mixture was stirred at r.t. for 75 minutes. The mixture was partitioned between DCM (50 mL) and 10% aqueous $K_2CO_3$ solution (20 mL). The organic layer was separated, dried ($MgSO_4$) and the solvent removed in vacuo to give an off-white solid (142 mg). A mixture of this solid (140 mg, 0.44 mmol), $K_2CO_3$ (64 mg, 0.47 mmol) and 6-mercaptopurine (79 mg, 0.47 mmol) in DMF (5 mL) was stirred at r.t. for 18 h. The mixture was partitioned between EtOAc (50 mL) and water (30 mL). The organic layer was separated, dried ($MgSO_4$) and the solvent removed in vacuo to give the title compound as a yellow solid (22 mg, 13%). $\delta_H$ (DMSO-$d_6$) 13.57 (br s, 1H), 8.74 (s, 1H), 8.46 (s, 2H), 8.43 (s, 1H), 8.12 (s, 1H), 7.67-7.75 (m, 1H), 7.52-7.58 (m, 1H), 7.36-7.42 (m, 1H), 5.04 (s, 2H), 3.94 (s, 3H), 2.73 (s, 3H). LCMS (ES+) 388.1 (M+H)$^+$, RT 2.86 minutes (Method 3).

Example 14

2-(2-Isopropoxyphenyl)-8-methyl-3-[(7H-purin-6-ylthio)methyl]quinoline

To a solution of Intermediate 63 (100 mg, 0.27 mmol) in DMF (5 mL) was added 6-mercaptopurine (48 mg, 0.28 mmol) and $K_2CO_3$ (39 mg, 0.28 mmol). The solution was stirred at r.t. for 26 h. The reaction mixture was diluted with EtOAc (30 mL) and washed with water (4×10 mL). The organic layer was separated, dried ($MgSO_4$), filtered and the solvent removed in vacuo to give the title compound (89 mg, 75%) as a white solid. $\delta_H$ (DMSO-$d_6$) 13.5 (br s, 1H), 8.60 (s, 1H), 8.45 (s, 1H), 8.38 (s, 1H), 7.79 (d, J 9 Hz, 1H), 7.56 (d, J 9 Hz, 1H), 7.35-7.50 (m, 3H), 7.13 (d, J 9 Hz, 1H), 7.05 (t, J 9 Hz, 1H), 4.75-4.85 (m, 1H), 4.55-4.70 (m, 2H), 2.67 (s, 3H), 1.30 (d, J 7.5 Hz, 3H), 1.08 (d, J 7.5 Hz, 3H). LCMS (ES+) 442.1 (M+H)$^+$, RT 3.81 minutes (Method 3).

Example 15

2-(2-Isopropylphenyl)-8-methyl-3-[(7H-purin-6-ylthio)methyl]quinoline

The title compound was prepared in a similar manner to Example 14, using Intermediate 64, and was obtained as a white solid (86 mg, 58%). $\delta_H$ (DMSO-$d_6$) 13.50 (br s, 1H), 8.60 (s, 1H), 8.55 (s, 1H), 8.38 (s, 1H), 7.82 (d, J 9 Hz, 1H), 7.60 (d, J 9 Hz, 1H), 7.20-7.50 (m, 5H), 4.54-4.68 (m, 2H), 2.65 (s, 3H), 2.55-2.65 (m, 1H), 1.18 (d, J 7.5 Hz, 6H). LCMS (ES+) 426.2 (M+H)$^+$, RT 4.26 minutes (Method 3).

Example 16

8-Methyl-2-(4-methylphenyl)-3-[(7H-purin-6-ylthio)methyl]quinoline

The title compound was prepared in a similar manner to Example 14, using Intermediate 65, and was obtained as a white solid (85 mg, 76%), after purification by column chromatography ($SiO_2$, 0-100% EtOAc in heptane). $\delta_H$ (DMSO-$d_6$) 13.52 (br s, 1H), 8.65 (s, 1H), 8.55 (s, 1H), 8.42 (s, 1H), 7.78-7.82 (m, 1H), 7.58-7.63 (m, 3H), 7.45-7.50 (m, 1H), 7.31 (d, J 7.9 Hz, 2H), 4.83 (s, 2H), 2.68 (s, 3H), 2.39 (s, 3H). LCMS (ES+) 398.2 (M+H)$^+$, RT 3.87 minutes (Method 3).

Example 17

8-Methyl-2-(3-methylphenyl)-3-[(7H-purin-6-ylthio)methyl]quinoline

The title compound was prepared in a similar manner to Example 14, using Intermediate 66, and was obtained as a white solid (133 mg, 88%). $\delta_H$ (DMSO-$d_6$) 13.53 (br s, 1H), 8.64 (s, 1H), 8.56 (s, 1H), 8.44 (s, 1H), 7.80 (d, J 9 Hz, 1H), 7.62 (d, J 9 Hz, 1H), 7.45-7.52 (m, 3H), 7.39 (d, J 9 Hz, 1H), 7.25 (d, J 9 Hz, 1H), 4.83 (s, 2H), 2.69 (s, 3H), 2.35 (s, 3H). LCMS (ES+) 398.2 (M+H)$^+$, RT 3.89 minutes (Method 3).

Example 18

2-(Biphenyl-2-yl)-8-methyl-3-[(7H-purin-6-ylthio)methyl]quinoline

The title compound was prepared in a similar manner to Example 14, using Intermediate 67, and was obtained as a white solid (63 mg, 30%) after purification by preparative HPLC (Method 1). $\delta_H$ (DMSO-$d_6$) 8.58 (s, 1H), 8.39 (s, 1H), 8.31 (s, 1H), 7.70-7.75 (m, 1H), 7.40-7.60 (m, 6H), 7.10-7.20 (m, 5H), 4.30-4.49 (m, 2H), 2.57 (s, 3H). LCMS (ES+) 460.2 (M+H)$^+$, RT 4.07 minutes (Method 4).

Example 19

8-Methyl-3-[(7H-purin-6-ylthio)methyl]-2-(1H-pyrazol-4-yl)quinoline

The title compound was prepared in a similar manner to Example 14, using Intermediate 68, and was obtained as a white solid (14 mg, 15%) after purification by preparative HPLC (Method 1). $\delta_H$ (DMSO-$d_6$) 13.56 (br s, 1H), 13.20 (br s, 1H), 8.74 (s, 1H), 8.44-8.47 (m, 2H), 8.41 (br s, 1H), 8.19 (br s, 1H), 7.73 (d, J 9 Hz, 1H), 7.57 (d, J 9 Hz, 1H), 7.49 (t, J 9 Hz, 1H), 5.04 (s, 2H), 2.73 (s, 3H). LCMS (ES+) 374.1 (M+H)$^+$, RT 2.59 minutes (Method 3).

Example 20

2-(2-Chlorophenyl)-8-methyl-3-[(7H-purin-6-ylthio)methyl]quinoline

The title compound was prepared in a similar manner to Example 14, using Intermediate 69, and was obtained as a pale yellow solid (134 mg, 54%) after trituration with diethyl ether and MeOH. $\delta_H$ (DMSO-$d_6$) 13.51 (br s, 1H), 8.58-8.61 (m, 2H), 8.41 (s, 1H), 7.83-7.89 (m, 1H), 7.38-7.68 (m, 6H), 4.67-4.79 (m, 1H), 4.54-4.64 (m, 1H), 2.65 (s, 3H). LCMS (ES+) 418.2 (M+H)$^+$, RT 3.77 minutes (Method 3).

Example 21

8-Methyl-2-(1,3-oxazol-2-yl)-3-[(7H-purin-6-ylthio)methyl]quinoline

To a solution of Intermediate 70 (81 mg, 0.27 mmol) in DMF (2 mL) was added 2N NaOH solution (4 mL) and 6-mercaptopurine (43 mg, 0.25 mmol). The reaction mixture was stirred at r.t. for 3 h. The mixture was acidified by adding AcOH and partitioned between EtOAc (30 mL) and aqueous $K_2CO_3$ solution (20 mL). The organic layer was separated, dried ($MgSO_4$) and the solvent removed in vacuo. Purification by preparative HPLC (Method 1) gave the title compound as a white solid (22 mg, 22%). $\delta_H$ (DMSO-$d_6$) 8.68 (s, 2H), 8.46 (s, 1H), 8.29 (s, 1H), 7.83 (d, J 9 Hz, 1H), 7.63-7.68 (m, 2H), 7.52-7.58 (m, 1H), 5.34 (s, 2H), 2.76 (s, 3H). LCMS (ES+) 375.1 (M+H)$^+$, RT 3.30 minutes (Method 3).

Example 22

2-(3,5-Dimethylisoxazol-4-yl)-8-methyl-3-[(7H-purin-6-ylthio)methyl]quinoline

The title compound was prepared in a similar manner to Example 21, using Intermediate 71, and was obtained as a pale yellow solid (77 mg, 68%) after purification by preparative HPLC (Method 1). $\delta_H$ (DMSO-$d_6$) 8.61 (s, 1H), 8.58 (s, 1H), 8.40 (s, 1H), 7.83 (d, J 7.5 Hz, 1H), 7.62 (d, J 7.5 Hz, 1H), 7.50 (t, J 7.5, 1H), 4.75 (s, 2H), 2.66 (s, 3H), 2.38 (s, 3H), 2.13 (s, 3H). LCMS (ES+) 403.2 (M+H)$^+$, RT 3.22 minutes (Method 3).

Example 23

2-(2,6-Difluorophenyl)-8-methyl-3-[(7H-purin-6-ylthio)methyl]quinoline

The title compound was prepared in a similar manner to Example 14, using Intermediate 72, and was obtained as a white solid (102 mg, 56%) after purification by column chromatography ($SiO_2$, 75-100% EtOAc in heptane). $\delta_H$ ($CDCl_3$) 11.32 (br s, 1H), 8.66 (s, 1H), 8.46 (s, 1H), 8.11 (s, 1H), 7.63-7.67 (m, 1H), 7.50-7.55 (m, 1H), 7.33-7.46 (m, 2H), 7.00-7.10 (m, 2H), 4.71 (s, 2H), 2.78 (s, 3H). LCMS (ES+) 420.1 (M+H)$^+$, RT 3.65 minutes (Method 3).

Example 24

2-(2-Fluoro-6-methoxyphenyl)-8-methyl-3-[(7H-purin-6-ylthio)methyl]quinoline

The title compound was prepared in a similar manner to Example 4, using Intermediate 73, and was obtained as a white solid (62 mg, 42%) after purification by preparative HPLC (Method 2). $\delta_H$ ($CDCl_3$) 11.45 (br s, 1H), 8.68 (s, 1H), 8.40 (s, 1H), 8.10 (s, 1H), 7.63 (d, J 9 Hz, 1H), 7.50 (d, J 9 Hz, 1H), 7.27-7.43 (m, 2H), 6.74-6.88 (m, 2H), 4.76 (d, J 12 Hz, 1H), 4.59 (d, J 12 Hz, 1H), 3.80 (s, 3H), 2.77 (s, 3H). LCMS (ES+) 432.1 (M+H)$^+$, RT 3.60 minutes (Method 4).

Example 25

2-(2-Methoxyphenyl)-8-methyl-3-[(7H-purin-6-ylthio)methyl]quinoline

To a solution of (2-chloro-8-methylquinolin-3-yl)methanol (250 mg, 1.20 mmol) in DME (4 mL) and water (1 mL) was added 2-methoxybenzeneboronic acid (200 mg, 1.32 mmol), potassium phosphate tribasic (306 mg, 1.44 mmol) and Pd(PPh$_3$)$_4$ (69 mg, 0.06 mmol). The reaction mixture was heated to 120° C. under microwave irradiation for 1 h. The product was diluted with EtOAc (40 mL) and washed with water (10 mL). The organic layer was separated, dried (MgSO$_4$), filtered and concentrated in vacuo to give a yellow oil, which was purified by column chromatography (SiO$_2$, 30% EtOAc in heptane) to give a yellow foam. To a solution of this product (200 mg) in DCM (10 mL) was added phosphorus tribromide (0.13 mL, 1.43 mmol) and the mixture was stirred at r.t. for 2 h. The mixture was partitioned between DCM (75 mL) and aqueous NaHCO$_3$ solution (20 mL). The organic layer was washed with water (20 mL), separated, dried (MgSO$_4$) and the solvent removed in vacuo to give a yellow oil. To a solution of this oil (200 mg) in DMF (10 mL) was added K$_2$CO$_3$ (89 mg, 0.64 mmol) and 6-mercaptopurine (109 mg, 0.64 mmol) and the reaction mixture was stirred at r.t. for 18 h. The reaction mixture was diluted with EtOAc (150 mL) and washed with water (7×30 mL). The organic layer was separated, dried (MgSO$_4$) and the solvent removed in vacuo to give a colourless oil. Trituration in DCM/diethyl ether gave the title compound (112 mg, 22%) as an off-white solid. $\delta_H$ (DMSO-$d_6$) 13.50 (br s, 1H), 8.63 (s, 1H), 8.46 (s, 1H), 8.42 (s, 1H), 7.80 (d, J 9 Hz, 1H), 7.58-7.60 (m, 1H), 7.35-7.50 (m, 3H), 7.02-7.16 (m, 2H), 4.60-4.70 (m, 2H), 3.78 (s, 3H), 2.65 (s, 3H). LCMS (ES+) 414.2 (M+H)$^+$, RT 3.40 minutes (Method 3).

Example 26

8-Methyl-3-[(7H-purin-6-ylthio)methyl]-2-(pyridin-3-yl)quinoline

A mixture of (2-chloro-8-methylquinolin-3-yl)methanol (250 mg, 1.21 mmol), pyridine-3-boronic acid (178 mg, 1.45 mmol) and K$_2$CO$_3$ (250 mg, 1.81 mmol) in DME (4 mL) and water (0.4 mL) was degassed for 5 minutes. Pd(PPh$_3$)$_4$ (70 mg, 0.06 mmol) was added and the reaction mixture was degassed for a further 5 minutes and heated to 120° C. under microwave irradiation for 1 h. The solvent was removed in vacuo and the product obtained was dissolved in DCM (19 mL). Phosphorus tribromide (0.83 mL, 8.8 mmol) was added to the mixture, which was stirred at r.t. for 90 minutes. The mixture was partitioned between DCM (50 mL) and 10% aqueous K$_2$CO$_3$ solution (30 mL). The organic layer was dried (MgSO$_4$) and the solvent removed in vacuo. The product obtained was dissolved in DMF (5 mL) and to the mixture was added K$_2$CO$_3$ (64 mg, 0.46 mmol) and 6-mercaptopurine (78 mg, 0.46 mmol). After stirring at r.t. for 18 h, the reaction mixture was diluted with EtOAc (150 mL) and washed with water (7×50 mL). The organic layer was separated, dried (MgSO$_4$), filtered and the solvent removed in vacuo. Purification by column chromatography (SiO$_2$, 1-10% MeOH in DCM) gave the title compound (49 mg, 10%) as an off-white solid. $\delta_H$ (DMSO-$d_6$) 13.51 (br s, 1H), 8.92-8.94 (m, 1H), 8.62-8.65 (m, 1H), 8.61 (s, 1H), 8.58 (s, 1H), 8.40 (s, 1H), 8.18 (d, J 7.7 Hz, 1H), 7.85 (d, J 7.7 Hz, 1H), 7.50-7.66 (m, 3H), 4.86 (s, 2H), 2.70 (s, 3H). LCMS (ES+) 385.1 (M+H)$^+$, RT 2.45 minutes (Method 3).

Example 27

2-(4-Fluorophenyl)-8-methyl-3-[(7H-purin-6-ylthio)methyl]quinoline

To a solution of (2-chloro-8-methylquinolin-3-yl)methanol (250 mg, 1.21 mmol) in DME (4 mL) and water (0.4 mL) was added 4-fluorophenylboronic acid (203 mg, 1.45 mmol) and K$_2$CO$_3$ (250 mg, 1.81 mmol). The mixture was degassed by bubbling through N$_2$ for 5 minutes before adding Pd(PPh$_3$)$_4$ (70 mg, 0.06 mmol) and degassing for a further 5 minutes. The reaction mixture was heated to 120° C. under microwave irradiation for 1 h. The mixture was diluted with EtOAc (100 mL) and washed with water (30 mL). The organic layer was separated, dried (MgSO$_4$) and concentrated in vacuo. Purification by column chromatography (SiO$_2$, 0-50% EtOAc in heptane) gave a white solid. To a solution of this solid (230 mg) in DCM (10 mL) was added phosphorus tribromide (0.4 mL, 4.31 mmol) and the mixture was stirred at r.t. for 90 minutes. The mixture was partitioned between DCM (100 mL) and 10% aqueous K$_2$CO$_3$ solution (30 mL). The organic layer was separated, dried (MgSO$_4$) and the solvent removed in vacuo to give a white solid. To a solution of this solid in DMF (30 mL) was added potassium carbonate (352 mg, 2.55 mmol) and 6-mercaptopurine (433 mg, 2.55 mmol). The reaction mixture was stirred at r.t. for 18 h. The mixture was diluted with EtOAc (100 mL) and washed with water (7×40 mL). The organic layer was separated, dried (MgSO$_4$) and the solvent removed in vacuo to give the title compound (217 mg, 45%) as a white solid. $\delta_H$ (DMSO-d$_6$) 13.54 (br s, 1H), 8.63 (s, 1H), 8.57 (s, 1H), 8.42 (s, 1H), 7.75-7.83 (m, 3H), 7.60-7.65 (m, 1H), 7.45-7.55 (m, 1H), 7.30-7.38 (m, 2H), 4.85 (s, 2H), 2.69 (s, 3H). LCMS (ES+) 402.2 (M+H)$^+$, RT 3.79 minutes (Method 3).

Example 28

2-(2-Chloro-6-fluorophenyl)-8-methyl-3-[(7H-purin-6-ylthio)methyl]quinoline

To a solution of (2-chloro-8-methylquinolin-3-yl)methanol (250 mg, 1.21 mmol) in DME (4 mL) and water (1 mL) was added 2-chloro-6-fluorophenylboronic acid (230 mg, 1.32 mmol), potassium phosphate tribasic (306 mg, 1.44 mmol), potassium hydrogenfluoride (188 mg, 2.4 mmol) and Pd(PPh$_3$)$_4$ (69 mg, 0.06 mmol). The reaction mixture was heated to 120° C. under microwave irradiation for 1 h. The product was diluted with EtOAc (30 mL) and washed with water (10 mL). The organic layer was separated, dried (MgSO$_4$), filtered and concentrated in vacuo to give a yellow oil. Purification by column chromatography (SiO$_2$, 0-50% EtOAc in heptane) followed by preparative HPLC (Method 1) gave a white solid. To a solution of this solid (150 mg) in DCM (7 mL) was added phosphorus tribromide (0.2 mL, 2.48 mmol). The mixture was stirred at r.t. for 3 h and partitioned between DCM (50 mL) and 10% aqueous K$_2$CO$_3$ solution (20 mL). The organic layer was separated, dried (MgSO$_4$) and the solvent removed in vacuo to give a clear oil. To a solution of this oil in DMF (7 mL) was added K$_2$CO$_3$ (72 mg, 0.52 mmol) and 6-mercaptopurine (88 mg, 0.52 mmol) and the mixture stirred at r.t. for 18 h. The reaction mixture was diluted with EtOAc (100 mL) and washed with water (7×30 mL). The organic layer was separated, dried (MgSO$_4$) and the solvent was removed in vacuo to give the title compound (102 mg, 19%) as a white solid. $\delta_H$ (DMSO-d$_6$) 13.46 (br s, 1H), 8.64 (s, 1H), 8.57 (s, 1H), 8.41 (s, 1H), 7.89 (d, J 6 Hz, 1H), 7.65 (d, J 6 Hz, 1H), 7.56 (t, J 6 Hz, 1H), 7.40-7.50 (m, 2H), 7.24-7.30 (m, 1H), 4.64-4.72 (m, 2H), 2.64 (s, 3H). LCMS (ES+) 436.2 (M+H)$^+$, RT 3.77 minutes (Method 3).

Example 29

8-Methyl-3-[(7H-purin-6-ylthio)methyl]-2-(pyridin-4-yl)quinoline

The title compound was prepared in a similar manner to Example 26 and was obtained as a white solid (37 mg, 8%) after purification by column chromatography (SiO$_2$, 1-10% MeOH in DCM) followed by preparative HPLC (Method 1). $\delta_H$ (DMSO-d$_6$) 13.50 (m, 1H), 8.73 (m, 2H), 8.62 (d, J 7.7 Hz, 2H), 8.41 (s, 1H), 7.85 (d, J 8.1 Hz, 1H), 7.74-7.77 (m, 2H), 7.63 (d, J 7.5 Hz, 1H), 7.53 (t, J 7.5 Hz, 1H), 4.86 (s, 2H), 2.69 (s, 3H). LCMS (ES+) 385.0 (M+H)$^+$, RT 2.28 minutes (Method 3).

Example 30

2-(2-Methoxypyridin-3-yl)-8-methyl-3-[(7H-purin-6-ylthio)methyl]quinoline

The title compound was prepared in a similar manner to Example 26 and was obtained as an off-white solid (94 mg, 18%) after purification by column chromatography (SiO$_2$, 1-10% MeOH in DCM). $\delta_H$ (DMSO-d$_6$) 13.64 (s br, 1H), 8.74 (s, 1H), 8.66 (s, 1H), 8.55 (s, 1H), 8.36-8.38 (m, 1H), 7.93-8.00 (m, 2H), 7.76 (d, J 9 Hz, 1H), 7.65 (t, J 9 Hz, 1H), 7.20-7.24 (m, 1H), 4.85 (s, 2H), 4.03 (s, 3H), 2.80 (s, 3H). LCMS (ES+) 415.1 (M+H)$^+$, RT 3.23 minutes (Method 3).

Example 31

8-Methyl-3-[(7H-purin-6-ylthio)methyl]-2-(thien-2-yl)quinoline

The title compound was prepared in a similar manner to Example 4, using Intermediate 74, and was obtained as an off-white solid (56 mg, 34%) after purification by preparative HPLC (Method 2). $\delta_H$ (DMSO-d$_6$) 8.75 (s, 1H), 8.56 (s, 1H), 8.46 (s, 1H), 7.85 (d, J 6 Hz, 1H), 7.77 (d, J 7.5 Hz, 2H), 7.61 (d, J 7.5 Hz, 1H), 7.45 (t, J 7.5 Hz, 1H), 7.19-7.26 (m, 1H), 5.12 (s, 2H), 2.72 (s, 3H). LCMS (ES+) 390.1 (M+H)$^+$, RT 4.10 minutes (Method 4).

Example 32

4-Methyl-2-(2-methylphenyl)-3-[(7H-purin-6-ylthio)methyl]quinoline

A mixture of 2-aminoacetophenone (2 g, 14.8 mmol) and ethyl (2-methyl-benzoyl)acetate (3.66 g, 17.8 mmol) in toluene (70 mL) was heated at reflux for 18 h using a Dean-Stark condenser. After cooling, the reaction mixture was concentrated in vacuo and the residue purified by column chromatography (SiO$_2$, 0-50% EtOAc in heptane) to give a yellow oil (407 mg). To a solution of this oil (350 mg, 1.15 mmol) in THF (15 mL) under N$_2$ cooled to 0° C. was added dropwise a 1.0M solution of lithium aluminium hydride in THF (2.3 mL, 2.30 mmol). The reaction mixture was allowed to warm to r.t. and stirred for 90 minutes. The mixture was re-cooled to 0° C. and quenched with water (0.2 mL), 15% NaOH solution (0.2 mL) and water (0.6 mL), allowed to warm to r.t. and stirred for 30 minutes. The mixture was filtered through MgSO$_4$ and washed with THF (20 mL). The filtrate was concentrated in vacuo to give a yellow oil (250 mg). This was dissolved in DCM (10 mL) and to the solution was added phosphorus tribromide (0.11 mL, 1.2 mmol). The mixture was stirred at r.t. for 90 minutes and then poured into cold 10% K$_2$CO$_3$ solution (20 mL) and extracted with DCM (2×50 mL). The organic layers were combined, dried (MgSO$_4$) and concentrated in vacuo. Purification by column chromatography (SiO$_2$, 0-50% EtOAc in heptane) gave a clear colourless oil. This was dissolved in DMF (3 mL) and to this solution was added 6-mercaptopurine (14 mg, 0.08 mmol) and K$_2$CO$_3$ (11 mg, 0.08 mmol). The mixture was stirred at r.t. for 72 h. The mixture was diluted with EtOAc (100 mL) and washed with water (5×30 mL). The organic layer was separated, dried (MgSO$_4$), filtered and concentrated in vacuo. Purification by column chromatography (SiO$_2$, 0-10% MeOH in DCM) gave the title compound (14 mg, 0.3%) as a white solid. $\delta_H$ (CDCl$_3$) 12.11 (br s, 1H), 8.64 (s, 1H), 8.22 (d, J 10 Hz, 1H), 8.10 (d, J 10 Hz, 1H), 7.86 (s, 1H), 7.75 (t, J 8 Hz, 1H), 7.62 (t, J 8 Hz, 1H), 7.35 (d, J 10 Hz, 1H), 7.30-7.10 (m, 9H), 4.92 (d, J 12.5 Hz, 1H), 4.57 (d, J 12.5 Hz, 1H), 2.91 (s, 3H), 2.12 (s, 3H). LCMS (ES+) 398.2 (M+H)$^+$, RT 2.32 minutes (Method 1).

Example 33

5-Fluoro-8-methyl-2-(2-methylphenyl)-3-[(7H-purin-6-ylthio)methyl]quinoline The title compound was prepared in a similar manner to Example 14, using Intermediate 75, and was obtained as a white solid (90 mg, 88%). $\delta_H$ (DMSO-d$_6$) 13.52 (br s, 1H), 8.70 (s, 1H), 8.60 (s, 1H), 8.42 (s, 1H), 7.55-7.62 (m, 1H), 7.25-7.40 (m, 5H), 4.60-4.70 (m, 2H), 2.60 (s, 3H), 2.12 (s, 3H). LCMS (ES+) 416.2 (M+H)$^+$, RT 3.95 minutes (Method 3).

Example 34

5-Chloro-8-methyl-2-(2-methylphenyl)-3-[(7H-purin-6-ylthio)methyl]quinoline A mixture of (2,5-dichloro-8-methylquinolin-3-yl)methanol (500 mg, 2.06 mmol), o-tolylboronic acid (337 mg, 2.48 mmol) and K$_2$CO$_3$ (428 mg, 3.09 mmol) in DME (8 mL) and water (2 mL) was degassed by bubbling N$_2$ through it for 5 minutes. Pd(PPh$_3$)$_4$ (119 mg, 0.1 mmol) was added and the reaction mixture was degassed for a further 5 minutes and then heated to 120° C. under microwave irradiation for 1 h. The solvent was removed in vacuo and the product was dissolved in DCM (40 mL). To this solution was added phosphorus tribromide (1.34 mL, 14.23 mmol) and the reaction mixture was stirred at r.t. for 3 h. The mixture was partitioned between DCM (100 mL) and 10% aqueous K$_2$CO$_3$ solution (50 mL). The organic layer was separated, dried (MgSO$_4$) and the solvent removed in vacuo. The product obtained was dissolved in DMF (10 mL) and to this solution was added K$_2$CO$_3$ (147 mg, 1.06 mmol) and 6-mercaptopurine (180 mg, 1.06 mmol). The reaction mixture was stirred at r.t. for 18 h. The mixture was diluted with EtOAc (150 mL) and was washed with water (7×50 mL). The organic layer was separated, dried (MgSO$_4$) and the solvent removed in vacuo. Purification by column chromatography (SiO$_2$, 0-5% MeOH in DCM), then by preparative HPLC (Method 1), gave the title compound (149 mg, 16%) as an off-white solid. $\delta_H$ (DMSO-d$_6$) 13.48 (br s, 1H), 8.86 (s, 1H), 8.62 (s, 1H), 8.43 (s, 1H), 7.66 (d, J 9 Hz, 1H), 7.59 (d, J 9 Hz, 1H), 7.35 (m, 4H), 4.68 (br s, 2H), 2.62 (s, 3H), 2.12 (s, 3H). LCMS (ES+) 432.2, 434.1 (M+H)$^+$, RT 4.25 minutes (Method 3).

Example 35

6-Methyl-2-phenyl-3-[(7H-purin-6-ylthio)methyl]quinoline

The title compound was prepared in a similar manner to Example 5, using Intermediate 76, and was obtained as a white solid (72 mg, 48%). $\delta_H$ (DMSO-d$_6$) 13.54 (br s, 1H), 8.64 (s, 1H), 8.49 (s, 1H), 8.41 (s, 1H), 7.90 (d, J 8.7 Hz, 1H), 7.75 (s, 1H), 7.65-7.68 (m, 2H), 7.66 (dd, J 8.7, 1.9 Hz, 1H), 7.44-7.54 (m, 3H), 4.80 (s, 2H), 2.50 (s, 3H). LCMS (ES+) 384.2 (M+H)$^+$, RT 3.35 minutes (Method 4).

Example 36

6-Fluoro-2-(2-methylphenyl)-3-[(7H-purin-6-ylthio)methyl]quinoline

The title compound was prepared in a similar manner to Example 14, using Intermediate 77, and was obtained as a white solid (40 mg, 82%) after purification by column chromatography (SiO$_2$, 0-60% EtOAc in heptane). $\delta_H$ (CDCl$_3$) 11.55 (br s, 1H), 8.71 (s, 1H), 8.45 (s, 1H), 8.15-8.22 (m, 1H), 7.99 (s, 1H), 7.25-7.50 (m, 6H), 4.50-4.80 (m, 2H), 2.18 (s, 3H). LCMS (ES+) 402.2 (M+H)$^+$, RT 3.15 minutes (Method 3).

Example 37

6-Methoxy-2-phenyl-3-[(7H-purin-6-ylthio)methyl]quinoline

The title compound was prepared in a similar manner to Example 4, using Intermediate 78, and was obtained as a white solid (125 mg, 52%) after purification by preparative HPLC (Method 1). $\delta_H$ (DMSO-d$_6$) 10.70 (br s, 1H), 9.08 (s, 1H), 8.63 (s, 1H), 8.48 (s, 1H), 8.12 (d, J 9 Hz, 1H), 7.81-7.87 (m, 2H), 7.65-7.74 (m, 5H), 4.82 (s, 2H), 3.94 (s, 3H). LCMS (ES+) 400.1 (M+H)$^+$, RT 3.21 minutes (Method 4).

Example 38

6,7-Difluoro-2-(2-methylphenyl)-3-[(7H-purin-6-ylthio)methyl]quinoline

A mixture of (2-chloro-6,7-difluoroquinolin-3-yl)methanol (200 mg, 0.87 mmol), K$_2$CO$_3$ (181 mg, 1.31 mmol) and o-tolylboronic acid (142 mg, 1.05 mmol in DME (4 mL) and water (0.4 mL) was degassed by bubbling through N$_2$ for 5 minutes. Pd(PPh$_3$)$_4$ (50 mg, 0.04 mmol) was added and the mixture heated in a microwave at 120° C. for 1 h. The solvent was removed in vacuo to give a clear gum (162 mg). To a solution of this gum (250 mg, 0.88 mmol) in DCM (10 mL) was added phosphorus tribromide (0.4 mL, 4.39 mmol) and the reaction mixture was stirred at r.t. for 75 minutes. The mixture was partitioned between DCM (100 mL) and 10% aqueous K$_2$CO$_3$ solution (30 mL). The organic layer was separated, dried (MgSO$_4$) and the solvent removed in vacuo to give a yellow gum. A mixture of this gum (185 mg, 0.53 mmol), K$_2$CO$_3$ (77 mg, 0.56 mmol) and 6-mercaptopurine (95 mg, 0.56 mmol) in DMF (5 mL) was stirred at r.t. for 18 h. Purification by column chromatography (SiO$_2$, 5-100% EtOAc in heptane) gave the title compound as a white solid (85 mg, 52%). $\delta_H$ (DMSO-d$_6$) 13.53 (br s, 1H), 8.63 (s, 1H), 8.60 (s, 1H), 8.42 (s, 1H), 8.10-8.18 (m, 1H), 7.95-8.05 (m, 1H), 7.25-7.38 (m, 4H), 4.50-4.60 (m, 2H), 2.08 (s, 3H). LCMS (ES+) 420.1 (M+H)$^+$, RT 3.45 minutes (Method 3).

Example 39

7-Fluoro-2-(2-methylphenyl)-3-[(7H-purin-6-ylthio)methyl]quinoline

The title compound was prepared in a similar manner to Example 21, using Intermediate 79, and was obtained as a white solid (43 mg, 27%) after purification by column chromatography (SiO$_2$, 0-100% EtOAc in heptane) then by preparative HPLC (Method 1). $\delta_H$ (DMSO-d$_6$) 13.51 (br s, 1H), 8.66 (s, 1H), 8.60 (s, 1H), 8.41 (s, 1H), 8.10-8.15 (m, 1H), 7.70-7.75 (m, 1H), 7.50-7.60 (m, 1H), 7.20-7.45 (m, 4H), 4.55-4.65 (m, 2H), 2.09 (s, 3H). LCMS (ES+) 402.1 (M+H)+, RT 3.16 minutes (Method 3).

Example 40

7-Methyl-2-phenyl-3-[(7H-purin-6-ylthio)methyl]quinoline

The title compound was prepared in a similar manner to Example 4, using Intermediate 80, and was obtained as a white solid (34 mg, 22%) after purification by preparative HPLC (Method 1). $\delta_H$ (DMSO-$d_6$) 13.52 (br s, 1H), 8.63 (s, 1H), 8.55 (s, 1H), 8.40 (s, 1H), 7.89 (d, J 8.3 Hz, 1H), 7.80 (s, 1H), 7.67 (br s, 2H), 7.42-7.55 (m, 4H), 4.80 (s, 2H), 2.52 (s, 3H). LCMS (ES+) 384.19 (M+H)+, RT 3.34 minutes (Method 4).

Example 41

7-Methyl-2-(2-methylphenyl)-3-[(7H-purin-6-ylthio)methyl]quinoline

The title compound was prepared in a similar manner to Example 4, using Intermediate 81, and was obtained as a white solid (58 mg, 40%) after purification by preparative HPLC (Method 1). $\delta_H$ (DMSO-$d_6$) 13.50 (br s, 1H), 8.61 (s, 1H), 8.54 (s, 1H), 8.42 (s, 1H), 7.89 (d, J 8.5 Hz, 1H), 7.76 (d, J 0.8 Hz, 1H), 7.45 (dd, J 8.3, 1.5 Hz, 1H), 7.25-7.35 (m, 4H), 4.57 (br s, 2H), 2.50 (s, 3H), 2.08 (s, 3H). LCMS (ES+) 398.2 (M+H)+, RT 3.45 minutes (Method 4).

Example 42

7-Fluoro-8-methyl-2-(2-methylphenyl)-3-[(7H-purin-6-ylthio)methyl]quinoline

The title compound was prepared in a similar manner to Example 3, using Intermediate 82, and was obtained as a white solid (60 mg, 50%) after purification by preparative HPLC (Method 1). $\delta_H$ (DMSO-$d_6$) 13.26 (br s, 1H), 8.63 (s, 1H), 8.59 (s, 1H), 8.40 (s, 1H), 7.91-7.96 (m, 1H), 7.52 (t, J 7.5 Hz 1H), 7.25-7.39 (m, 4H), 4.60 (br s, 2H), 2.54 (d, J 3 Hz, 3H), 2.12 (s, 3H). LCMS (ES+) 414.2 (M+H)+, RT 3.96 minutes (Method 3).

Example 43

8-Ethyl-2-phenyl-3-[(7H-purin-6-ylthio)methyl]quinoline

To a solution of Intermediate 53 (90 mg, 0.34 mmol) in DCM (2 mL) under $N_2$ was added phosphorus tribromide (0.16 mL, 1.7 mmol). The reaction mixture was stirred at room temperature for 2 h. The mixture was poured into $K_2CO_3$ solution (20 mL) and extracted with DCM (30 mL). The organic layer was separated, dried (MgSO$_4$) and concentrated in vacuo to give a white solid. To a solution of this solid (72 mg, 0.22 mmol) in DMF (2.5 mL) under $N_2$ was added a solution of 6-mercaptopurine (34 mg, 0.2 mmol) in DMF (0.5 mL). The reaction mixture was stirred at room temperature for 18 h. Purification by preparative HPLC (Method 1) gave the title compound as a white solid (51 mg, 38%). $\delta_H$ (DMSO-$d_6$) 13.51 (br s, 1H), 8.64 (s, 1H), 8.58 (s, 1H), 8.41 (s, 1H), 7.82 (dd, J 8.1, 1.3 Hz, 1H), 7.70-7.75 (m, 2H), 7.59-7.63 (m, 1H), 7.46-7.57 (m, 4H), 4.85 (s, 2H), 3.17 (q, J 7.5 Hz, 2H), 1.30 (t, J 7.5 Hz, 3H). LCMS (ES+) 398.0 (M+H)+, RT 4.04 minutes (Method 3).

Example 44

8-Benzyl-2-(2-methylphenyl)-3-[(7H-purin-6-ylthio)methyl]quinoline

A mixture of Intermediate 54 (250 mg, 0.88 mmol), $K_2CO_3$ (183 mg, 1.33 mmol) and o-tolylboronic acid (126 mg, 0.93 mmol) in DME (4 mL) and water (0.4 mL) was degassed by bubbling $N_2$ through it for 5 minutes. Pd(PPh$_3$)$_4$ (51 mg, 0.04 mmol) was added and the mixture heated in a microwave at 120° C. for 1 h. Purification by column chromatography (SiO$_2$, 0-50% EtOAc in heptane) gave a yellow gum (119 mg), which was dissolved in DCM (5 mL). Phosphorus tribromide (0.02 mL, 0.22 mmol) was added dropwise and the mixture was stirred at r.t. for 70 minutes. The mixture was partitioned between DCM (100 mL) and 10% aqueous $K_2CO_3$ solution (50 mL). The organic layer was separated, dried (MgSO$_4$) and the solvent removed in vacuo to give a yellow gum. A mixture of this gum (66 mg, 0.16 mmol), $K_2CO_3$ (23 mg, 0.17 mmol) and 6-mercaptopurine (29 mg, 0.17 mmol) in DMF (2 mL) was stirred at r.t. for 4 h. Purification by preparative HPLC (Method 1) gave the title compound as a white solid (40 mg, 52%). $\delta_H$ (CDCl$_3$) 11.33 (br s, 1H), 8.69 (s, 1H), 8.43 (s, 1H), 8.11 (s, 1H), 7.60-7.70 (m, 1H), 7.35-7.45 (m, 3H), 7.10-7.30 (m, 8H), 4.50-4.70 (m, 4H), 2.14 (s, 3H). LCMS (ES+) 474.2 (M+H)+, RT 4.32 minutes (Method 3).

Example 45

8-Methyl-2-phenyl-3-[1-(7H-purin-6-ylthio)ethyl]quinoline, formic acid salt

The title compound was prepared in a similar manner to Example 4, using Intermediate 83, and was obtained as a white solid (33 mg, 49%). $\delta_H$ (CDCl$_3$) 12.31 (br s, 1H), 8.54 (s, 1H), 8.48 (br s, 1H), 8.09 (s, 1H), 7.78-7.84 (m, 2H), 7.64-7.69 (m, 1H), 7.37-7.55 (m, 6H), 5.62-5.72 (m, 1H), 2.79 (s, 3H) 1.82 (d, J 7 Hz, 3H). LCMS (ES+) 398.1 (M+H)+, RT 3.81 minutes (Method 3).

Example 46

8-Methyl-3-[1-(7H-purin-6-ylthio)ethyl]-2-(pyridin-3-yl)quinoline

The title compound was prepared in a similar manner to Example 4, using Intermediate 84, and was obtained as a white solid (17 mg, 24%) after purification by preparative HPLC (Method 1). $\delta_H$ (DMSO-$d_6$) 13.20 (br s, 1H), 8.88 (d, J 2.3 Hz, 1H), 8.78 (s, 1H), 8.64 (dd, J 4.7, 1.5 Hz, 1H), 8.45 (s, 1H), 8.39 (s, 1H), 8.10-8.16 (m, 1H), 7.91 (d, J 7.5 Hz, 1H), 7.61-7.67 (m, 1H), 7.48-7.57 (m, 2H), 5.57 (q, J 7.0 Hz, 1H), 2.69 (s, 3H), 1.88 (d, J 7.0 Hz, 3H). LCMS (ES+) 399.0 (M+H)+, RT 2.60 minutes (Method 3).

Example 47

8-Methyl-2-phenyl-3-[1-(7H-purin-6-ylthio)propyl]quinoline, formic acid salt

The title compound was prepared in a similar manner to Example 4, using Intermediate 85, and was obtained as a white solid (10 mg, 17%). $\delta_H$ (CDCl$_3$) 11.40 (br s, 1H), 8.52 (s, 1H), 8.44 (s, 1H), 8.08 (s, 1H), 7.77-7.82 (m, 2H), 7.62-7.68 (m, 1H), 7.40-7.55 (m, 5H), 5.64-5.73 (m, 1H), 2.79 (s, 3H), 2.10-2.20 (m, 2H), 0.95 (t, J 7.2 Hz, 3H). LCMS (ES+) 412 (M+H)$^+$, RT 4.04 minutes (Method 3).

Example 48

4-Methyl-6-{[8-methyl-2-(3-thienyl)quinolin-3-yl]methoxy}pyrimidin-2-amine

To a suspension of 2-amino-4-hydroxy-6-methylpyrimidine (43 mg, 0.35 mmol) in anhydrous DMF (3 mL) under N$_2$ was added NaH (60% dispersion in oil, 16 mg, 0.39 mmol). After 25 minutes, Intermediate 58 (100 mg, 0.31 mmol) was added and the mixture heated at 100° C. for 75 minutes. The reaction was cooled, diluted with 50% brine (20 mL) and extracted with 2:1 EtOAc-MTBE (2×30 mL). The organic layer was separated, dried (MgSO$_4$) and concentrated in vacuo. Purification by preparative HPLC (Method 1) followed by flash chromatography (SiO$_2$, 25% heptane in EtOAc) gave the title compound (72.8 mg, 65%) as a colourless solid. $\delta_H$ (MeOD-d$_4$) 8.32 (s, 1H), 7.78-7.80 (m, 1H), 7.64-7.70 (m, 2H), 7.58 (d, J 9 Hz, 1H), 7.40-7.48 (m, 2H), 6.05 (s, 1H), 5.54 (s, 2H), 2.81 (s, 3H), 2.28 (s, 3H). LCMS (ES+) 363.1 (M+H)$^+$, RT 4.34 minutes (Method 4).

Example 49

4-Methyl-6-({8-methyl-2-[2-(trifluoromethoxy)phenyl]quinolin-3-yl}methoxy)pyrimidin-2-amine The title compound was prepared in a similar manner to Example 6, using Intermediate 26, and was obtained as a white solid (44 mg, 20%) after purification by preparative HPLC (Method 1). $\delta_H$ (CDCl$_3$) 8.30 (s, 1H), 7.65-7.75 (m, 1H), 7.55-7.60 (m, 2H), 7.40-7.55 (m, 4H), 5.95 (s, 1H), 5.55 (br s, 2H), 5.35 (br s, 2H), 2.80 (s, 3H), 2.25 (s, 3H). LCMS (ES+) 441.1 (M+H)$^+$, RT 2.76 minutes (Method 3).

Example 50

4-{[2-(2-Isopropoxyphenyl)-8-methylquinolin-3-yl]methoxy}-6-methylpyrimidin-2-amine The title compound was prepared in a similar manner to Example 6, using Intermediate 31, but with additional heating at 100° C. in a sealed tube for 2 days, and was obtained as a clear colourless oil (16 mg, 13%) after purification by preparative HPLC (Method 1). $\delta_H$ (CDCl$_3$) 8.21 (s, 1H), 7.68 (d, J 9 Hz, 1H), 7.49-7.55 (m, 2H), 7.36-7.44 (m, 2H), 7.07-7.13 (m, 1H), 7.00 (d, J 9 Hz, 1H), 5.95 (s, 1H), 5.46-5.51 (m, 1H), 5.25-5.30 (m, 1H), 4.81 (br s, 2H), 4.40-4.54 (m, 1H), 2.80 (s, 3H), 2.21 (s, 3H), 1.31 (d, J 7.5 Hz, 3H), 1.08 (d, J 7.5 Hz, 3H). LCMS (ES+) 415.2 (M+H)$^+$, RT 2.70 minutes (Method 3).

Example 51

4-{[2-(2-Isopropylphenyl)-8-methylquinolin-3-yl]methoxy}-6-methylpyrimidin-2-amine The title compound was prepared in a similar manner to Example 6, using Intermediate 32, but with additional heating at 100° C. in a sealed tube for 2 days, and was obtained as a clear colourless oil (78 mg, 43%) after purification by preparative HPLC (Method 1). $\delta_H$ (CDCl$_3$) 8.25 (s, 1H), 7.70 (d, J 7.5 Hz, 1H), 7.57 (d, J 7.5 Hz, 1H), 7.35-7.50 (m, 3H), 7.22-7.27 (m, 2H), 5.98 (s, 1H), 5.13-5.30 (m, 2H), 5.06 (br s, 2H), 2.67-2.83 (m, 4H), 2.25 (s, 3H), 1.23 (d, J 6 Hz, 3H), 1.15 (d, J 6 Hz, 3H). LCMS (ES+) 399.2 (M+H)$^+$, RT 2.97 minutes (Method 3).

Example 52

4-{[2-(3,5-Dimethylisoxazol-4-yl)-8-methylquinolin-3-yl]methoxy}-6-methylpyrimidin-2-amine, formic acid salt The title compound was prepared in a similar manner to Example 48, using Intermediate 71, and was obtained as a white solid (43 mg, 41%) after purification by preparative HPLC (Method 1). $\delta_H$ (MeOD-d$_4$) 8.53 (s, 1H), 8.24 (br s, 1H), 7.85 (d, J 7.5 Hz, 1H), 7.68 (d, J 7.5 Hz, 1H), 7.54 (t, J 7.5 Hz, 1H), 6.02 (s, 1H), 5.43 (s, 2H), 2.78 (s, 3H), 2.38 (s, 3H), 2.26 (s, 3H), 2.20 (s, 3H). LCMS (ES+) 376.1 (M+H)$^+$, RT 2.32 minutes (Method 3).

Example 53

4-Methyl-6-{[8-methyl-2-(pyridin-3-yl)quinolin-3-yl]methoxy}pyrimidin-2-amine, formic acid salt The title compound was prepared in a similar manner to Example 6, using Intermediate 43, and was obtained as a white solid (40 mg, 28%) after purification by preparative HPLC (Method 1). $\delta_H$ (DMSO-d$_6$) 8.90 (dd, J 2.1, 0.6 Hz, 1H), 8.69 (dd, J 4.7, 1.7 Hz, 1H), 8.61 (s, 1H), 8.19 (s, 1H), 8.10-8.15 (m, 1H), 7.91 (d, J 7.5 Hz, 1H), 7.65-7.70 (m, 1H), 7.52-7.55 (m, 2H), 6.48 (br s, 2H), 5.94 (s, 1H), 5.42 (s, 2H), 2.73 (s, 3H), 2.14 (s, 3H). LCMS (ES+) 358.0 (M+H)$^+$, RT 1.96 minutes (Method 3).

Example 54

4-[(5-Fluoro-8-methyl-2-phenylquinolin-3-yl)methoxy]-6-methylpyrimidin-2-amine

The title compound was prepared in a similar manner to Example 48, using Intermediate 46, and was obtained as a white solid (21 mg, 27%). $\delta_H$ (DMSO-d$_6$) 8.62 (s, 1H), 7.62-7.74 (m, 3H), 7.50-7.56 (m, 3H), 7.38 (dd, J 10.0, 7.9 Hz, 1H), 6.45 (br s, 2H), 5.99 (s, 1H), 5.45 (s, 2H), 2.68 (s, 3H), 2.15 (s, 3H). LCMS (ES+) 375.2 (M+H)$^+$, RT 2.65 minutes (Method 3).

Example 55

4-{[5-Chloro-8-methyl-2-(2-methylphenyl)quinolin-3-yl]methoxy}-6-methylpyrimidin-2-amine A mixture of (2,5-dichloro-8-methylquinolin-3-yl)methanol (500 mg, 2.06 mmol), o-tolylboronic acid (337 mg, 2.48 mmol) and K$_2$CO$_3$ (428 mg, 3.09 mmol) in DME (8 mL) and water (2 mL) was degassed for 5 minutes. Pd(PPh$_3$)$_4$ (119 mg, 0.1 mmol) was added and the reaction mixture was degassed for a further 5 minutes then heated to 120° C. under microwave irradiation for 1 h. The solvent was removed in vacuo and the residue was dissolved in DMF (30 mL). To this solution was added sodium hydride (60% in mineral oil, 102 mg, 4.27 mmol) and the mixture was stirred at r.t. for 30 minutes. 2-Amino-4-chloro-6-methylpyrimidine (490 mg, 3.41 mmol) was added and the mixture was stirred at r.t. for 18 h. The mixture was diluted with EtOAc (150 mL) and washed with water (7×30 mL). The organic layer was separated, dried (MgSO$_4$) and the solvent removed in vacuo. Purification by column chromatography (SiO$_2$, 0-5% MeOH in DCM) then by preparative HPLC (Method 1) gave the title compound as a white solid (100 mg, 12%). $\delta_H$ (CDCl$_3$) 8.72 (s, 1H), 7.44-7.55 (m, 2H), 7.24-7.36 (m, 4H), 5.99 (s, 1H), 5.27 (s, 2H), 4.92 (br s, 2H), 2.73 (s, 3H), 2.24 (s, 3H), 2.18 (s, 3H). LCMS (ES+) 405.1, 407.0 (M+H)$^+$, RT 2.91 minutes (Method 3).

Example 56

4-{[6-Fluoro-2-(2-methylphenyl)quinolin-3-yl]methoxy}-6-methylpyrimidin-2-amine, formic acid salt The title compound was prepared in a similar manner to Example 6, using Intermediate 29, and was obtained as an orange solid (8 mg, 6%) after purification by preparative HPLC (Method 1). $\delta_H$ (MeOD-d$_4$) 8.58 (s, 1H), 8.20 (s, 1H), 8.05-8.10 (m, 1H), 7.70-7.78 (m, 1H), 7.60-7.69 (m, 1H), 7.30-7.40 (m, 4H), 6.04 (s, 1H), 5.30 (s, 2H), 2.26 (s, 3H), 2.11 (s, 3H). LCMS (ES+) 375.1 (M+H)$^+$, RT 2.27 minutes (Method 3).

Example 57

4-Methyl-6-[(7-methyl-2-phenylquinolin-3-yl)methoxy]pyrimidin-2-amine

The title compound was prepared in a similar manner to Example 6, using Intermediate 50, and was obtained as a white solid (18 mg, 12%) after purification by preparative HPLC (Method 2). $\delta_H$ (CDCl$_3$) 8.28 (s, 1H), 7.95 (d, J 0.7 Hz, 1H), 7.75 (d, J=8.5 Hz, 1H), 7.61-7.65 (m, 2H), 7.41-7.51 (m, 3H), 7.39 (dd, J 8.3, 1.1 Hz, 1H), 6.01 (s, 1H), 5.40 (s, 2H), 5.08 (s, 2H), 2.57 (s, 3H), 2.27 (s, 3H). LCMS (ES+) 357.3 (M+H)$^+$, RT 3.79 minutes (Method 4).

Example 58

4-Methyl-6-{[7-methyl-2-(2-methylphenyl)quinolin-3-yl]methoxy}pyrimidin-2-amine

The title compound was prepared in a similar manner to Example 6, using Intermediate 51, and was obtained as a white solid (18 mg, 15%) after purification by preparative HPLC (Method 2). $\delta_H$ (CDCl$_3$) 8.25 (s, 1H), 7.93 (d, J 0.8 Hz, 1H), 7.77 (d, J=7.5 Hz, 1H), 7.41 (dd, J 8.3, 1.5 Hz, 1H), 7.24-7.32 (m, 4H), 5.97 (s, 1H), 5.22 (s, 2H), 5.02 (br s, 2H), 2.57 (s, 3H), 2.26 (s, 3H), 2.13 (s, 3H). LCMS (ES+) 371.2 (M+H)$^+$, RT 3.84 minutes (Method 4).

Example 59

4-{[7-Fluoro-8-methyl-2-(2-methylphenyl)quinolin-3-yl]methoxy}-6-methyl-pyrimidin-2-amine The title compound was prepared in a similar manner to Example 48, using Intermediate 82, and was obtained as a white solid (50 mg, 44%) after purification by preparative HPLC (Method 1). $\delta_H$ (DMSO-d$_6$) 8.60 (s, 1H), 8.00 (dd, J 97.5 Hz, 1H), 7.56 (t, J 9 Hz, 1H), 7.25-7.42 (m, 4H), 6.42 (br s, 2H), 5.89 (s, 1H), 5.15 (s, 2H), 2.56 (d, J 3 Hz, 3H), 2.12 (s, 3H), 2.07 (s, 3H). LCMS (ES+) 389.2 (M+H)$^+$, RT 2.68 minutes (Method 3).

Example 60

4-[(8-Ethyl-2-phenylquinolin-3-yl)methoxy]-6-methylpyrimidin-2-amine

The title compound was prepared in a similar manner to Example 6, using Intermediate 53, and was obtained as a white solid (28 mg, 21%) after purification by preparative HPLC (Method 1). $\delta_H$ (DMSO-d$_6$) 8.55 (s, 1H), 7.88 (d, J 7.0 Hz, 1H), 7.46-7.73 (m, 7H), 6.47 (br s, 2H), 5.97 (s, 1H), 5.40 (s, 2H), 3.22 (q, J 7.5 Hz, 2H), 2.14 (s, 3H), 1.32 (t, J 7.5 Hz, 3H). LCMS (ES+) 371.0 (M+H)$^+$, RT 2.65 minutes (Method 3).

Example 61

4-{[8-Benzyl-2-(2-methylphenyl)quinolin-3-yl]methoxy}-6-methylpyrimidin-2-amine, formic acid salt A mixture of Intermediate 54 (250 mg, 0.88 mmol), K$_2$CO$_3$ (183 mg, 1.33 mmol) and o-tolylboronic acid (126 mg, 0.93 mmol) in DME (4 mL) and water (0.4 mL) was degassed by bubbling through N$_2$ for 5 minutes. Pd(PPh$_3$)$_4$ (51 mg, 0.04 mmol) was added and the mixture heated in a microwave at 120° C. for 1 h. Purification by column chromatography (SiO$_2$, 0-50% EtOAc in heptane) gave a yellow gum (119 mg). To a solution of the yellow gum (58 mg, 0.17 mmol) in DMF (2 mL) stirring under N$_2$ was added sodium hydride (60% in mineral oil, 10 mg, 0.26 mmol) and the mixture stirred for 2 h. 2-Amino-4-chloro-6-methylpyrimidine (29 mg, 0.21 mmol) was added and the mixture was stirred at r.t. for 4 h. Purification by preparative HPLC (Method 1) gave the title compound as a yellow solid (8 mg, 10%). $\delta_H$ (CDCl$_3$) 8.26 (s, 1H), 7.72 (dd, J 7.0, 2.4 Hz, 1H), 7.45-7.50 (m, 2H), 7.10-7.35 (m, 10H), 6.15 (br s, 2H), 5.94 (s, 1H), 5.27 (s, 2H), 4.64 (br s, 2H), 2.29 (s, 3H), 2.09 (s, 3H). LCMS (ES+) 447.2 (M+H)$^+$, RT 2.94 minutes (Method 3).

Example 62

4-Methyl-6-[1-(8-methyl-2-phenylquinolin-3-yl)ethoxy]pyrimidin-2-amine

The title compound was prepared in a similar manner to Example 6, using Intermediate 55, and was obtained as a white solid (17 mg, 29%) after purification by preparative HPLC (Method 1). $\delta_H$ (CDCl$_3$) 8.29 (s, 1H), 7.71-7.77 (m, 2H), 7.67 (d, J 7.5 Hz, 1H), 7.48-7.58 (m, 4H), 7.41 (t, J 7.5 Hz, 1H), 6.38 (q, J 6.6 Hz, 1H), 5.92 (s, 1H), 4.71 (br s, 2H), 2.80 (s, 3H), 2.18 (s, 3H), 1.65 (d, J 6.6 Hz, 3H). LCMS (ES+) 371.2 (M+H)$^+$, RT 2.65 minutes (Method 3).

Example 63

4-Methyl-6-{1-[8-methyl-2-(pyridin-3-yl)quinolin-3-yl]ethoxy}pyrimidin-2-amine

The title compound was prepared in a similar manner to Example 6, using Intermediate 56, and was obtained as a white solid (33 mg, 31%) after purification by preparative HPLC (Method 1). $\delta_H$ (DMSO-d$_6$) 8.87 (d, J 1.5 Hz, 1H), 8.71 (dd, J 4.9, 1.7 Hz, 1H), 8.47 (s, 1H), 8.13-8.21 (m, 1H), 7.89 (d, J 7.9 Hz, 1H), 7.49-7.63 (m, 3H), 6.13-6.27 (m, 3H), 5.94 (s, 1H), 2.69 (s, 3H), 2.11 (s, 3H), 1.51 (d, J 6.4 Hz, 3H). LCMS (ES+) 372.0 (M+H)$^+$, RT 2.13 minutes (Method 3).

Example 64

4-Methyl-6-({8-methyl-2-[2-(trifluoromethyl)phenyl]quinolin-3-yl}methoxy)-pyrimidin-2-amine The title compound was prepared in a similar manner to Example 6, using Intermediate 38, and was obtained as a pale yellow solid (34 mg, 17%) after purification by preparative HPLC (Method 1). $\delta_H$ (DMSO-$d_6$) 8.57 (s, 1H), 7.90 (d, J 7.5 Hz, 2H), 7.54-7.80 (m, 5H), 6.46 (br s, 2H), 5.85 (s, 1H), 5.18 (s, 2H), 2.65 (s, 3H), 2.11 (s, 3H). LCMS (ES+) 425.1 (M+H)$^+$, RT 2.63 minutes (Method 3).

Example 65

4-Isopropyl-6-[(8-methyl-2-phenylquinolin-3-yl)methoxy]pyrimidin-2-amine

A mixture of Intermediate 6 (100 mg, 0.32 mmol), 2-amino-4-chloro-6-isopropylpyrimidine (58 mg, 0.38 mmol) and sodium hydride (60% in mineral oil, 18 mg, 0.45 mmol) in DMF (2 mL) was stirred at 100° C. for 45 minutes. Purification was by preparative HPLC (Method 1) followed by partitioning between DCM (20 mL) and 10% aqueous $K_2CO_3$ solution (10 mL). The organic layer was separated, dried (MgSO$_4$) and concentrated in vacuo to give the title compound as a white solid (37 mg, 30%). $\delta_H$ (CDCl$_3$) 8.32 (s, 1H), 7.71-7.77 (m, 2H), 7.69 (d, J 8.1 Hz, 1H), 7.57 (d, J 9 Hz, 1H), 7.41-7.53 (m, 4H), 6.03 (s, 1H), 5.47 (s, 2H), 4.82 (br s, 2H), 2.83 (s, 3H), 2.64-2.79 (m, 1H), 1.21 (d, J 7 Hz, 6H). LCMS (ES+) 385.2 (M+H)$^+$, RT 2.92 minutes (Method 3).

Example 66

6-[(6-Methoxy-2-phenylquinolin-3-yl)methoxy]pyrimidine-2,4-diamine

The title compound was prepared in a similar manner to Example 6, using Intermediate 48, and was obtained as a white solid (36 mg, 38%) after purification by preparative HPLC (Method 1). $\delta_H$ (CDCl$_3$) 8.23 (s, 1H), 8.05 (d, J 9.2 Hz, 1H), 7.60-7.65 (m, 2H), 7.44-7.52 (m, 3H), 7.11 (d, J 2.8 Hz, 1H), 6.02 (s, 1H), 5.42 (s, 2H), 4.93 (br s, 2H), 3.95 (s, 3H), 2.27 (s, 3H). LCMS (ES+) 373.2 (M+H)$^+$, RT 2.02 minutes (Method 3).

Example 67

4-[(8-Methyl-2-phenylquinolin-3-yl)methoxy]-6-methyl-1,3,5-triazin-2-amine

To a solution of Intermediate 7 (100 mg, 0.32 mmol) in MeCN (5 mL) was added Cs$_2$CO$_3$ (313 mg, 0.96 mmol) and 4-amino-6-methyl-1,3,5-triazin-2-ol (57 mg, 0.45 mmol). The reaction mixture was heated at 80° C. for 18 h, filtered and the solvent removed in vacuo. Purification by preparative HPLC (Method 2) gave the title compound as an off-white solid (13 mg, 11%). $\delta_H$ (CDCl$_3$) 8.41 (s, 1H), 7.65-7.76 (m, 3H), 7.40-7.60 (m, 5H), 5.55 (s, 2H), 5.24 (br s, 2H), 2.82 (s, 3H), 2.38 (s, 3H). LCMS (ES+) 358 (M+H)$^+$, RT 3.82 minutes (Method 4).

Example 68

4-[(8-Methyl-2-phenylquinolin-3-yl)methoxy]pyrimidine-2-amine

The title compound was prepared in a similar manner to Example 67, using Intermediate 7 and 2-amino-4-hydroxypyrimidine, and was obtained as an off-white solid (14 mg, 13%) after purification by preparative HPLC (Method 2). $\delta_H$ (CDCl$_3$) 8.31 (s, 1H), 8.03 (d, J 7.5 Hz, 1H), 7.68-7.78 (m, 3H), 7.55-7.60 (m, 1H), 7.40-7.54 (m, 4H), 6.14-6.17 (m, 1H), 5.49 (s, 2H), 4.98 (br s, 2H), 2.83 (s, 3H). LCMS (ES+) 343.2 (M+H)$^+$, RT 4.21 minutes (Method 4).

Example 69

4-[(8-Methyl-2-phenylquinolin-3-yl)methoxy]pyrido[3,4-d]pyrimidine

A mixture of Intermediate 7 (100 mg, 0.32 mmol), 3H-pyrido[3,4-d]pyrimidin-4-one (56 mg, 0.38 mmol) and sodium hydride (60% in mineral oil, 18 mg, 0.45 mmol) in DMF (2 mL) was stirred at r.t for 45 minutes. The crude mixture was purified by preparative HPLC (Method 1). The product obtained was partitioned between DCM (50 mL) and 10% aqueous $K_2CO_3$ solution (25 mL). The organic layer was separated, dried (MgSO$_4$) and concentrated in vacuo to give the title compound (10 mg, 8%) as a tan solid. $\delta_H$ (CDCl$_3$) 9.10 (s, 1H), 8.70 (d, J 5.3 Hz, 1H), 8.17 (s, 1H), 8.01 (dd, J 5.3, 0.9 Hz, 1H), 7.52-7.60 (m, 7H), 7.42-7.48 (m, 2H), 5.42 (s, 2H), 2.78 (s, 3H). LCMS (ES+) 379.3 (M+H)$^+$, RT 3.65 minutes (Method 3).

Example 70

4-[(8-Methyl-2-phenylquinolin-3-yl)methoxy]pyrido[2,3-d]pyrimidine

The title compound was prepared in a similar manner to Example 69, using Intermediate 7 and 3H-pyrido[2,3-d]pyrimidin-4-one, and was obtained as a clear glass (17 mg, 14%) after purification by preparative HPLC (Method 1) and partitioning between DCM (50 mL) and 10% aqueous $K_2CO_3$ solution (20 mL). $\delta_H$ (CDCl$_3$) 8.98 (dd, J 4.5, 2.0 Hz, 1H), 8.58 (dd, J 7.9, 2.0 Hz, 1H), 8.13 (s, 1H), 7.70 (s, 1H), 7.50-7.66 (m, 7H), 7.40-7.48 (m, 2H), 5.42 (s, 2H), 2.79 (s, 3H). LCMS (ES+) 379.2 (M+H)$^+$, RT 3.47 minutes (Method 3).

Example 71

1-[(8-Methyl-2-phenylquinolin-3-yl)methoxy]isoquinolin-3-amine

The title compound was prepared in a similar manner to Example 6, using Intermediate 7 and 1-bromoisoquinolin-3-ylamine, and was obtained as a beige solid (6.4 mg, 8%) after purification by preparative HPLC (Method 2). $\delta_H$ (CDCl$_3$) 8.42 (s, 1H), 8.08 (d, J 9 Hz, 1H), 7.79-7.84 (m, 2H), 7.70 (d, J 9 Hz, 1H), 7.54 (d J 9 Hz, 1H), 7.48-7.52 (m, 7H), 7.12-7.20 (m, 1H), 6.30 (s, 1H), 5.68 (s, 2H), 4.18 (br s, 2H), 2.85 (s, 3H). LCMS (ES+) 392.1 (M+H)$^+$, RT 4.93 minutes (Method 4).

Example 72

2-Amino-6-{[7-fluoro-8-methyl-2-(2-methylphenyl)quinolin-3-yl]methoxy}-pyrimidin-4-ol The title compound was prepared in a similar manner to Example 48, using Intermediate 82 and 2-amino-4,6-dihydroxypyrimidine, and was obtained as a white solid (8 mg, 7%) after purification by preparative HPLC (Method 1). $\delta_H$ (MeOD-$d_4$) 8.47 (s, 1H), 7.84-7.93 (m, 1H), 7.26-7.47 (m, 5H), 5.15 (s, 2H), 4.99 (s, 1H), 2.64 (m, 3H), 2.15 (s, 3H). LCMS (ES+) 391.2 (M+H)+, RT 3.43 minutes (Method 3).

Example 73

4-{1-[8-Methyl-2-(pyridin-3-yl)quinolin-3-yl]ethoxy}pyrimidin-2-amine

The title compound was prepared in a similar manner to Example 6, using Intermediate 56, and was obtained as a yellow gum (5 mg, 5%) after purification by preparative HPLC (Method 1). $\delta_H$ (CDCl$_3$) 9.04 (d, J 1.7 Hz, 1H), 8.74 (dd, J 4.9, 1.7 Hz, 1H), 8.34 (s, 1H), 8.06 (dt, J 7.9, 2.1 Hz, 1H), 7.83-7.88 (m, 1H), 7.70 (d, J 8.3 Hz, 1H), 7.55-7.60 (m, 1H), 7.42-7.53 (m, 2H), 6.38 (q, J 6.6 Hz, 1H), 6.05-6.10 (m, 1H), 5.41 (br s, 2H), 2.79 (s, 3H), 1.68 (d, J 6.6 Hz, 3H). LCMS (ES+) 358.1 (M+H)+, RT 2.04 minutes (Method 3).

Example 74

N-[(8-Methyl-2-phenylquinolin-3-yl)methyl]quinoxalin-6-amine

To a solution of 8-methyl-2-phenylquinoline-3-carboxaldehyde (80 mg, 0.32 mmol) in THF (5 mL) was added di-n-butyltin dichloride (10 mg, 0.032 mmol), phenylsilane (70 mg, 0.64 mmol) and 6-aminoquinoxaline (46 mg, 0.32 mmol). The mixture was heated in a microwave at 100° C. for 3 h. Purification by preparative HPLC (Method 2) gave the title compound as an off-white solid (45 mg, 37%). $\delta_H$ (CDCl$_3$) 8.61 (d, J 2.1 Hz, 1H), 8.51 (d, J 1.9 Hz, 1H), 8.24 (s, 1H), 7.84 (d, J 9.0 Hz, 1H), 7.71-7.76 (m, 1H), 7.61-7.66 (m, 1H), 7.40-7.58 (m, 6H), 7.10 (dd, J 9.2, 2.6 Hz, 1H), 6.88 (d, J 2.6 Hz, 1H), 4.64-4.69 (m, 2H), 4.52-4.60 (m, 1H), 2.82 (s, 3H). LCMS (ES+) 377.2 (M+H)+, RT 4.23 minutes (Method 4).

Example 75

2-Chloro-6-methyl-N-[(8-methyl-2-phenylquinolin-3-yl)methyl]pyrimidin-4-amine

To a solution of Intermediate 88 (100 mg, 0.4 mmol) in THF (5 mL) was added 2,4-dichloro-6-methylpyrimidine (66 mg, 0.4 mmol). The mixture was heated in a microwave at 80° C. for 1 h. Purification by preparative HPLC (Method 1) gave the title compound as an off-white solid (35 mg, 23%). $\delta_H$ (CDCl$_3$) 8.16 (s, 1H), 7.40-7.66 (m, 8H), 5.92 (s, 1H), 5.20 (br s, 1H), 4.65-4.75 (m, 2H), 2.82 (s, 3H), 2.28 (s, 3H). LCMS (ES+) 375.2, 377.2 (M+H)+, RT 4.12 minutes (Method 3).

Example 76

4-Chloro-6-methyl-N-[(8-methyl-2-phenylquinolin-3-yl)methyl]pyrimidin-2-amine

Also obtained from the procedure of Example 75, to give the title compound as an off-white solid (32 mg, 21%). $\delta_H$ (CDCl$_3$) 8.22 (s, 1H), 7.65-7.71 (m, 3H), 7.40-7.55 (m, 5H), 6.48 (s, 1H), 5.35-5.39 (m, 1H), 4.82 (d, J 6.2 Hz, 2H), 2.82 (s, 3H), 2.29 (s, 3H). LCMS (ES+) 375.2, 377.2 (M+H)+, RT 4.71 minutes (Method 3).

Example 77

6-Methyl-N$^4$-[(8-methyl-2-phenylquinolin-3-yl)methyl]pyrimidine-2,4-diamine, di-acetic acid salt To a solution of Intermediate 88 (50 mg, 0.2 mmol) in NMP (3 mL) was added 2-amino-4-chloro-6-methylpyrimidine (32 mg, 0.22 mmol) and DIPEA (29 mg, 0.22 mmol) The mixture was heated in a microwave at 220° C. for 1 h. Purification by preparative HPLC (Method 1; followed by Method 2) gave the title compound as an off-white solid (25 mg, 35%). $\delta_H$ (CDCl$_3$) 8.11 (s, 1H), 7.42-7.59 (m, 8H), 5.43 (s, 1H), 5.10-5.15 (m, 1H), 4.65-4.75 (m, 2H), 2.81 (s, 3H), 2.18 (s, 3H) 2.05 (s, 6H). LCMS (ES+) 356.2 (M+H)+, RT 2.20 minutes (Method 3).

Example 78

N$^4$-[(8-Methyl-2-phenylquinolin-3-yl)methyl]pyrimidine-2,4-diamine, di-acetic acid salt The title compound was prepared in a similar manner to Example 77, using Intermediate 88 and 2-amino-4-chloropyrimidine, and was obtained as an off-white solid (22 mg, 32%), after purification by preparative HPLC (Method 1; followed by Method 2). $\delta_H$ (CDCl$_3$) 8.12 (s, 1H), 7.40-7.69 (m, 9H), 5.60-5.65 (m, 1H), 4.65-4.76 (m, 2H), 2.81 (s, 3H) 2.05 (s, 6H). LCMS (ES+) 342.2 (M+H)+, RT 2.18 minutes (Method 3).

Example 79

N$^4$,6-Dimethyl-N$^4$-[(8-methyl-2-phenylquinolin-3-yl)methyl]pyrimidine-2,4-diamine A mixture of 8-methyl-2-phenylquinoline-3-carboxaldehyde (100 mg, 0.4 mmol), methylamine hydrochloride (120 mg, 1.8 mmol) and DIPEA (230 mg, 1.8 mmol) in DCM (20 mL) was treated with titanium(IV) n-propoxide (228 mg, 0.8 mmol). The reaction mixture was stirred at r.t. for 18 h. The solvent was removed in vacuo and the residue dissolved in THF (20 mL) before triacetoxyborohydride (170 mg, 0.8 mmol) was added. The reaction mixture was stirred at r.t. for 2 h, the solvent removed in vacuo and the residue partitioned between DCM (100 mL) and water (30 mL). The organic layer was separated, dried (MgSO$_4$) and the solvent removed in vacuo. The residue was dissolved in NMP (2 mL) and to this solution was added DIPEA (230 mg, 1.8 mmol) and 2-amino-4-chloro-6-methylpyrimidine (57 mg, 0.4 mmol). The mixture was heated in a microwave at 220° C. for 2 h. Purification by preparative HPLC (Method 1) gave the title compound as an off-white solid (30 mg, 20%). $\delta_H$ (CDCl$_3$) 7.82 (s, 1H), 7.62-7.70 (m, 2H), 7.61 (d, J 7.9 Hz, 1H), 7.46-7.55 (m, 5H), 5.75 (s, 1H), 4.93 (s, 2H), 4.67 (s, 2H), 2.93 (s, 3H), 2.82 (s, 3H), 2.22 (s, 3H). LCMS (ES+) 370.2 (M+H)+, RT 2.36 minutes (Method 3).

Example 80

N$^2$,6-Dimethyl-N$^4$-[(8-methyl-2-phenylquinolin-3-yl)methyl]pyrimidine-2,4-diamine To a solution of Example 75 (50 mg, 0.13 mmol) in NMP (2 mL) was added methylamine hydrochloride (18 mg, 0.26 mmol) and DIPEA (0.5 mL). The mixture was heated in a microwave at 220° C. for 2 h. Purification by preparative HPLC (Method 1) gave the title compound as an off-white solid (23 mg, 44%). $\delta_H$ (CDCl$_3$) 8.17 (s, 1H), 7.63-7.70 (m, 3H), 7.38-7.57 (m, 5H), 5.47 (s, 1H), 4.80-4.95 (m, 2H), 4.69 (d, J 5.8 Hz, 2H), 2.91 (d, J 5.1 Hz, 3H), 2.81 (s, 3H), 2.14 (s, 3H). LCMS (ES+) 370.2 (M+H)$^+$, RT 2.34 minutes (Method 3).

Example 81

$N^2,N_2,6$-Trimethyl-$N^4$-[(8-methyl-2-phenylquinolin-3-yl)methyl]pyrimidine-2,4-diamine, formic acid salt The title compound was prepared in a similar manner to Example 80, using Example 75, and was obtained as an off-white solid (26 mg, 41%) after purification by preparative HPLC (Method 1). $\delta_H$ (CDCl$_3$) 8.38 (s, 1H), 8.12 (s, 1H), 7.38-7.68 (m, 8H), 6.22 (br s, 1H), 5.56 (s, 1H), 4.68-4.75 (m, 2H), 3.07 (s, 6H), 2.80 (s, 3H), 2.24 (s, 3H). LCMS (ES+) 384.2 (M+H)$^+$, RT 2.31 minutes (Method 3).

Example 82

6-Methyl-$N^4$-[(8-methyl-2-phenylquinolin-3-yl)methyl]-$N^2$-phenylpyrimidine-2,4-diamine, formic acid salt The title compound was prepared in a similar manner to Example 80, using Example 75, and was obtained as an off-white solid (29 mg, 47%), after purification by preparative HPLC (Method 1). $\delta_H$ (CDCl$_3$) 11.60 (br, s, 1H), 8.59 (s, 1H), 8.05 (s, 1H), 7.40-7.63 (m, 10H), 7.22-7.30 (m, 2H), 7.04-7.10 (m, 1H), 5.56 (s, 2H), 4.75-4.85 (m, 2H), 2.80 (s, 3H), 2.27 (s, 3H). LCMS (ES+) 432.3 (M+H)$^+$, RT 2.56 minutes (Method 3).

Example 83

$N^2$-(tert-Butyl)-6-methyl-$N^4$-[(8-methyl-2-phenylquinolin-3-yl)methyl]pyrimidine-2,4-diamine, formic acid salt The title compound was prepared in a similar manner to Example 80, using Example 75, and was obtained as an off-white solid (22 mg, 36%), after purification by preparative HPLC (Method 1). $\delta_H$ (CDCl$_3$) 9.52 (br, s, 1H), 8.63 (s, 1H), 8.07 (s 1H), 7.41-7.65 (m, 8H), 5.42-5.55 (m, 2H), 4.78-4.88 (m, 2H), 2.81 (s, 3H), 2.22 (s, 3H), 1.33 (s, 9H). LCMS (ES+) 412.2 (M+H)$^+$, RT 2.69 minutes (Method 3).

Example 84

4-Amino-6-methyl-1-[(8-methyl-2-phenylquinolin-3-yl)methyl]-1,3,5-triazin-2(1H)-one To a solution of Intermediate 7 (100 mg, 0.32 mmol) in MeCN (5 mL) was added 2-amino-4-hydroxy-6-methyl-1,3,5-triazine (57 mg, 0.45 mmol) and Cs$_2$CO$_3$ (313 mg, 0.96 mmol). The reaction mixture was heated at 80° C. for 18 h, filtered and concentrated in vacuo. Purification by preparative HPLC (Method 2) gave the title compound as an off-white solid (25 mg, 22%). $\delta_H$ (CDCl$_3$) 7.94 (s, 1H), 7.87 (d, J 7.9 Hz, 1H), 7.70-7.74 (m, 2H), 7.45-7.62 (m, 5H), 7.36 (s, 2H), 5.20 (s, 2H), 2.71 (s, 3H), 2.23 (s, 3H). LCMS (ES+) 358.2 (M+H)$^+$, RT 2.94 minutes (Method 3).

Example 85

3-{([(2-Chloro-6-methylpyrimidin-4-yl)thio]methyl}-8-methyl-2-phenylquinoline

To a solution of Intermediate 7 (891 mg, 2.85 mmol) in DMF (20 mL) was added thiolacetic acid (0.41 mL, 5.71 mmol) and K$_2$CO$_3$ (803 mg, 5.8 mmol). The reaction mixture was stirred at r.t. for 18 h and partitioned between Et$_2$O (100 mL) and water (50 mL). The organic layer was washed with water (4×30 mL), separated, dried (MgSO$_4$) and concentrated in vacuo to give a brown gum. To a solution of this gum (833 mg, 2.71 mmol) in MeOH (20 mL) was added sodium methoxide (270 mg, 5 mmol) and the mixture was stirred at r.t. for 1 h. 2,4-Dichloro-6-methylpyrimidine (652 mg, 4 mmol) was added and the reaction mixture was stirred at r.t. for 2 h. The solvent was removed in vacuo. Purification by column chromatography (SiO$_2$, 0-50% EtOAc in heptane) gave the title compound as a pale yellow solid (227 mg, 20%). $\delta_H$ (DMSO-d$_6$) 8.53 (s, 1H), 7.80-7.85 (m, 1H), 7.62-7.72 (m, 3H), 7.45-7.55 (m, 4H), 7.32 (s, 1H), 4.65 (s, 2H), 2.69 (s, 3H), 2.32 (s, 3H). LCMS (ES+) 392.2, 394.1 (M+H)$^+$, RT 5.00 minutes (Method 3).

Example 86

4-Methyl-6-{[(8-methyl-2-phenylquinolin-3-yl)methyl]thio}pyrimidin-2-amine

To a solution of Example 85 (100 mg, 0.26 mmol) in THF (1 mL) was added 7N ammonia in methanol (5 mL). The reaction mixture was heated in a microwave at 120° C. for 1 h and concentrated in vacuo. Purification by preparative HPLC (Method 1) gave the title compound as an off-white solid (24 mg, 20%). $\delta_H$ (DMSO-d$_6$) 8.60 (s, 1H), 8.27 (s, 1H), 7.84 (d, J 8.1 Hz, 1H), 7.66-7.70 (m, 2H), 7.60-7.65 (m, 1H), 7.45-7.58 (m, 3H), 6.61 (br s, 2H), 6.28 (s, 1H), 4.54 (s, 2H), 2.69 (s, 3H), 2.08 (s, 3H). LCMS (ES+) 373.2 (M+H)$^+$, RT 2.99 minutes (Method 3).

Example 87

N,6-Dimethyl-2-{[(8-methyl-2-phenylquinolin-3-yl)methyl]thio}pyrimidin-4-amine

To a solution of Intermediate 7 (891 mg, 2.85 mmol) in DMF (20 mL) was added thiolacetic acid (0.41 mL, 5.71 mmol) and K$_2$CO$_3$ (803 mg, 5.8 mmol). The reaction mixture was stirred at r.t. for 18 h and then partitioned between Et$_2$O (100 mL) and water (40 mL). The organic layer was washed with water (4×30 mL), separated, dried (MgSO$_4$) and concentrated in vacuo to give a brown gum. To a solution of this gum (833 mg, 2.71 mmol) in MeOH (20 mL) was added sodium methoxide (270 mg, 5 mmol). After stirring at r.t. for 1 h, 2,4-dichloro-6-methylpyrimidine (652 mg, 4 mmol) was added to the reaction mixture, which was stirred at r.t. for 2 h. The solvent was removed in vacuo. Purification by column chromatography (SiO$_2$, 0-50% EtOAc in heptane) gave a yellow oil. A mixture of this oil (115 mg, 0.29 mmol) and 2M methylamine in THF (5 mL) was heated in a microwave at 120° C. for 1 h and the solvent removed in vacuo. Purification by preparative HPLC (Method 1) gave the title compound as a pale yellow solid (6 mg, 2%). $\delta_H$ (DMSO-d$_6$) 8.52 (s, 1H), 7.81 (d, J 7.7 Hz, 1H), 7.67-7.73 (m, 2H), 7.58-7.63 (m, 1H), 6.95-7.55 (m, 4H), 7.25 (br s, 1H), 5.97 (s, 1H), 4.53 (s, 2H), 2.67-2.71 (m, 6H), 2.11 (s, 3H). LCMS (ES+) 387.2 (M+H)$^+$, RT 2.66 minutes (Method 3).

Example 88

N,4-Dimethyl-6-{[(8-methyl-2-phenylquinolin-3-yl)methyl]thio}pyrimidin-2-amine

A mixture of Example 85 (100 mg, 0.29 mmol), THF (1 mL) and 2M methylamine in THF (5 mL) was heated in a microwave at 120° C. for 1 h. The solvent was removed in vacuo. Purification by preparative HPLC (Method 1) gave the title compound as a white solid (12 mg, 10%). δ$_H$ (DMSO-d$_6$) 8.52-8.55 (m, 1H), 7.82 (dd, J 8.3, 0.4 Hz, 1H), 7.68-7.72 (m, 2H), 7.59-7.64 (m, 1H), 7.45-7.55 (m, 4H), 6.95-7.05 (m, 1H), 6.30 (s, 1H), 4.55-4.65 (m, 2H), 2.68-2.75 (m, 6H), 2.11 (s, 3H). LCMS (ES+) 387.3 (M+H)$^+$, RT 3.26 minutes (Method 3).

Example 89

N-[(8-Methyl-2-phenylquinolin-3-yl)methyl]-7H-purin-6-amine

To a solution of Intermediate 87 (950 mg, 2.51 mmol) in EtOH (50 mL) under N$_2$ was added hydrazine monohydrate (0.14 mL, 2.76 mmol). The reaction mixture was stirred at r.t. for 5 h, diluted with EtOH (30 mL), stirred at r.t. for 18 h and heated at 50° C. for 4 h. The mixture was concentrated in vacuo and partitioned between DCM (40 mL) and water (10 mL). The organic layer was separated, dried (MgSO$_4$) and the solvent removed in vacuo to give a yellow oil. A mixture of this oil (60 mg, 0.24 mmol), DIPEA (0.05 ml, 0.27 mmol) and 6-chloropurine (41 mg, 0.27 mmol) in n-butanol (2 mL) was heated in a microwave at 120° C. for 2 h. Purification by preparative HPLC (Method 1) gave the title compound as a yellow solid (26 mg, 30%). δ$_H$ (DMSO-d$_6$) 13.00 (br s, 1H), 8.30 (br s, 1H), 8.23 (s, 1H), 8.10-8.20 (m, 2H), 7.62-7.78 (m, 3H), 7.40-7.60 (m, 5H), 4.89 (br s, 2H), 2.71 (s, 3H). LCMS (ES+) 367.2 (M+H)$^+$, RT 2.72 minutes (Method 3).

Example 90

N-[1-(8-Methyl-2-phenylquinolin-3-yl)ethyl]-7H-purin-6-amine

To a solution of Intermediate 89 (54 mg, 0.14 mmol) in EtOH (2 ml) under N$_2$ was added hydrazine monohydrate (0.01 ml, 0.28 mmol) and the reaction mixture was stirred at r.t. for 3 h. The solvent was removed in vacuo to give a yellow oil. A mixture of this oil (60 mg, 0.24 mmol), DIPEA (0.03 mL, 1.5 mmol) and 6-chloropurine (23 mg, 1.5 mmol) in n-butanol (2 mL) was heated in a microwave at 120° C. for 2 h. Purification by preparative HPLC (Method 1) gave the title compound as a beige solid (30 mg, 57%). δ$_H$ (DMSO-d$_6$) 8.46-8.50 (m, 1H), 8.26-8.38 (m, 1H), 8.25 (s, 1H), 8.06-8.15 (m, 2H), 7.80-7.88 (m, 2H), 7.72 (d, J 7.5 Hz, 1H), 7.40-7.57 (m, 5H), 5.60-5.73 (m, 1H), 2.67 (s, 3H), 1.35-1.47 (m, 3H). LCMS (ES+) 381.2 (M+H)$^+$, RT 2.82 minutes (Method 3).

Example 91

2-(3,5-Dimethylisoxazol-4-yl)-8-methyl-3-[(7H-purin-6-ylamino)methyl]quinoline

To a solution of Intermediate 93 (50 mg, 0.14 mmol) in DCM (10 mL) was added TFA (5 mL). The reaction mixture was stirred for 1 h at r.t. and concentrated in vacuo. The residue was dissolved in NMP (1 mL) and DIPEA (0.5 ml) was added followed by 6-chloropurine (30 mg, 0.19 mmol). The solution was heated at 130° C. for 30 minutes in a microwave. The mixture was poured into water (20 mL) and extracted with EtOAc (100 mL). The organic layer was separated, dried (MgSO$_4$) and concentrated in vacuo. Purification by column chromatography (SiO$_2$, 5% MeOH in DCM) gave the title compound as a white solid (6 mg, 10%). δ$_H$ (MeOD-d$_4$) 8.37 (s, 1H), 8.20 (s, 1H), 8.05 (s, 1H), 7.75 (d, J 7.5 Hz, 1H), 7.62 (d, J 7.5 Hz, 1H), 7.50 (t, J 7.5 Hz, 1H), 4.90 (s, 2H), 2.73 (s, 3H), 2.40 (s, 3H), 2.15 (s, 3H). LCMS (ES+) 386.2 (M+H)$^+$, RT 2.49 minutes (Method 3).

Example 92

N-{[8-Methyl-2-(2-methylphenyl)quinolin-3-yl]methyl}-7H-purin-6-amine

To a solution of Intermediate 92 (100 mg, 0.33 mmol), 2-methylbenzeneboronic acid (66.5 mg, 0.49 mmol) and Pd(PPh$_3$)$_4$ (22.6 mg; 0.02 mmol) in DME (3.3 mL) was added 1.57M aqueous potassium phosphate tribasic solution (0.83 mL, 1.30 mmol). The reaction mixture was degassed three times and heated at 120° C. under microwave irradiation for 1 h. The product was diluted with DCM (10 mL) and water (10 mL) and the aqueous layer was extracted with DCM (2×10 mL). The combined organic layers were washed with brine (10 mL), filtered and the solvent evaporated in vacuo to give a brown oil. To a solution of the crude product (174 mg) in DCM (0.86 mL) was added trifluoroacetic acid (0.37 mL, 4.80 mmol). The mixture was stirred at r.t. for 18 h. The solvent was removed in vacuo and the residue partitioned between DCM (20 mL) and sat. aqueous NaHCO$_3$ solution (20 mL). The aqueous layer was extracted with DCM (2×10 mL) and the combined organic layers were washed with brine (10 mL), dried (MgSO$_4$) and concentrated in vacuo to give a brown oil. To a solution of this oil in n-butanol (2 mL) were added DIPEA (0.09 mL, 0.51 mmol) and 6-chloropurine (78.4 mg, 0.51 mmol). The reaction mixture was heated at 120° C. under microwave irradiation for 2 h. The solvent was removed in vacuo. Purification by preparative HPLC (Method 1) gave the title compound as a white solid (38 mg, 30%). δ$_H$ (DMSO) 12.89 (br s, 1H), 8.19 (s, 1H), 8.10-8.18 (m, 2H), 8.09 (s, 1H), 7.76 (d, J 9 Hz, 1H), 7.57 (d, J 9 Hz, 1H), 7.40-7.47 (m, 1H), 7.28-7.37 (m, 4H), 4.57 (br s, 2H), 2.65 (s, 3H), 2.15 (s, 3H). LCMS (ES+) 381.1 (M+H)$^+$, RT 2.74 minutes (Method 3).

Example 93

N-{[8-Methyl-2-(thien-3-yl)quinolin-3-yl]methyl}-7H-purin-6-amine

To a solution of Intermediate 92 (100 mg, 0.33 mmol) in DME/water (3 mL/1 mL) was added thiophene-3-boronic acid (100 mg, 0.78 mmol) and potassium phosphate tribasic acid (200 mg, 0.94 mmol). The mixture was degassed and bis (triphenylphosphine)-palladium(II) chloride (10.0 mg, 0.01 mmol) was added. The reaction mixture was heated at 140° C. under microwave irradiation for 20 minutes. The solvent was removed in vacuo and the residue extracted with EtOAc (20 mL). The organic layer was separated, dried (MgSO$_4$) and concentrated in vacuo. To a solution of the crude product in DCM (10 mL) was added trifluoroacetic acid (2 mL, 26.0 mmol). The mixture was stirred at r.t. for 1 h and the solvent removed in vacuo. To a solution of the crude product in NMP (2 mL) was added 6-chloropurine (100 mg, 0.65 mmol) and DIPEA (0.3 mL, 1.68 mmol). The reaction mixture was heated at 140° C. under microwave irradiation for 1 h. The mixture was poured into water (20 mL) and extracted with EtOAc (50 mL). The solvent was removed in vacuo and the residue was triturated with DCM to give the title compound as a beige solid (20 mg, 16%). δ$_H$/(DMSO) 12.99 (br s, 1H), 8.39 (br s, 1H), 8.05-8.24 (m, 4H), 7.66-7.77 (m, 3H), 7.58 (d, J 9 Hz, 1H), 7.35-7.45 (m, 1H), 5.05 (br s, 2H), 2.75 (s, 3H). LCMS (ES+) 373.1 (M+H)$^+$, RT 2.79 minutes (Method 3).

Example 94

9-[(8-Methyl-2-phenylquinolin-3-yl)methyl]-9H-purin-6-amine

A mixture of Intermediate 7 (156 mg, 0.5 mmol), adenine (74 mg, 0.55 mmol) and $K_2CO_3$ (76 mg, 0.55 mmol) in DMF (4 mL) was sonicated for 30 minutes then stirred at r.t for 18 h. Purification by preparative HPLC (Method 1) gave the title compound as a white solid (75 mg, 41%). $\delta_H$(DMSO-$d_6$) 8.02 (s, 1H), 7.89 (s, 1H), 7.88 (s, 1H), 7.75 (d, J 8 Hz, 1H), 7.68-7.69 (m, 2H), 7.62 (d, J 8 Hz, 1H), 7.42-7.56 (m, 4H), 7.24 (s, 2H), 5.60 (s, 2H), 2.70 (s, 3H). LCMS (ES+) 367.2 (M+H)+, RT 3.27 minutes (Method 4).

Example 95

7-[(8-Methyl-2-phenylquinolin-3-yl)methyl]-7H-purin-6-amine

The title compound was prepared in a similar manner to Example 94, using Intermediate 7, and was obtained as a white solid (3 mg, 2%), after purification by preparative HPLC (Method 1). $\delta_H$ (DMSO-$d_6$) 8.21 (s, 1H), 8.11 (s, 1H), 7.74-7.75 (m, 2H), 7.61-7.67 (m, 2H), 7.42-7.59 (m, 5H), 6.70 (s, 2H), 5.60 (s, 2H), 2.70 (s, 3H). LCMS (ES+) 367.2 (M+H)+, RT 2.92 minutes (Method 4).

Example 96

3-[(8-Methyl-2-phenylquinolin-3-yl)methyl]-3H-purin-6-amine

The title compound was prepared in a similar manner to Example 94, using Intermediate 7, and was obtained as a white solid (22 mg, 12%) after purification by preparative HPLC (Method 1). $\delta_H$ (DMSO-$d_6$) 8.10 (s, 1H), 8.05 (br s, 1H), 7.95 (s, 1H), 7.72-7.77 (m, 3H), 7.51-7.62 (m, 5H), 7.48 (t, J 8 Hz, 1H), 5.72 (s, 2H), 2.70 (s, 3H). LCMS (ES+) 367.2 (M+H)+, RT 2.70 minutes (Method 4).

Example 97

9-[(2-Phenylquinolin-3-yl)methyl]-9H-purin-6-amine, formic acid salt

A mixture of Intermediate 5 (113 mg, 0.37 mmol) and adenine (51 mg, 0.37 mmol) in DMF (4 mL) was sonicated for 40 minutes at 40° C. then stirred at r.t. for 18 h. More adenine (51 mg, 0.37 mmol) was added and the reaction heated to 80° C. for 1 h. Purification by preparative HPLC (Method 1) gave the title compound as a pale yellow solid (5 mg, 4%). $\delta_H$ (DMSO-$d_6$) 8.00-8.10 (m, 2H), 7.85-7.95 (m, 3H), 7.75-7.85 (m, 1H), 7.50-7.70 (m, 5H), 7.20-7.30 (m, 2H), 5.55 (s, 2H). LCMS (ES+) 353.2 (M+H)+, RT 1.94 minutes (Method 3).

Example 98

7-[(2-Phenylquinolin-3-yl)methyl]-7H-purin-6-amine, formic acid salt

The title compound was prepared in a similar manner to Example 97, using Intermediate 5, and was obtained as a white solid (6 mg, 5%) after purification by preparative HPLC (Method 1). $\delta_H$ (DMSO-$d_6$) 8.30 (s, 1H), 8.20 (s, 1H), 7.90-8.08 (m, 3H), 7.70-7.86 (m, 3H), 7.48-7.66 (m, 5H), 5.51 (s, 2H). LCMS (ES+) 353.2 (M+H)+, RT 2.02 minutes (Method 4).

Example 99

3-[(2-Phenylquinolin-3-yl)methyl]-3H-purin-6-amine, formic acid salt

The title compound was prepared in a similar manner to Example 97, using Intermediate 5, and was obtained as a white solid (69 mg, 53%) after purification by preparative HPLC (Method 1). $\delta_H$(DMSO-$d_6$)+TFA 8.70 (br s, 1H), 8.55 (s, 1H), 8.49 (s, 1H), 8.12-8.19 (m, 3H), 7.98 (t, J 8 Hz, 1H), 7.72-7.82 (m, 3H), 7.59-7.64 (m, 4H), 5.85 (s, 2H). LCMS (ES+) 353.2 (M+H)+, RT 1.57 minutes (Method 3).

Example 100

9-{[8-Methyl-2-(2-methylphenyl)quinolin-3-yl]methyl}-9H-purin-6-amine

A mixture of Intermediate 61 (98 mg, 0.3 mmol) and adenine (81 mg, 0.6 mmol) in DMF (3 mL) was stirred at 80° C. for 90 minutes. Purification by preparative HPLC (Method 2) gave the title compound as a white solid (6 mg, 6%). $\delta_H$ (DMSO-$d_6$) 8.30 (s, 1H), 8.16 (s, 1H), 7.66-7.69 (m, 1H), 7.55-7.59 (m, 1H), 7.26-7.49 (m, 5H), 7.09 (s, 1H), 5.53 (br s, 2H), 5.34 (s, 2H), 2.75 (s, 3H), 2.04 (s, 3H). LCMS (ES+) 381.2 (M+H)+, RT 3.37 minutes (Method 4).

Example 101

7-{[8-Methyl-2-(2-methylphenyl)quinolin-3-yl]methyl}-7H-purin-6-amine, acetic acid salt The title compound was prepared in a similar manner to Example 100, using Intermediate 61, and was obtained as a white solid (3 mg, 3%) after purification by preparative HPLC (Method 2). $\delta_H$ (DMSO-$d_6$) 8.11 (br s, 1H), 8.03 (s, 1H), 7.59-7.66 (m, 2H), 7.20-7.51 (m, 6H), 5.25 (s, 2H), 3.60 (br s, 2H), 2.76 (s, 3H), 2.09 (s, 3H) 2.03 (s, 3H). LCMS (ES+) 381.2 (M+H)+, RT 2.78 minutes (Method 4).

Example 102

3-{[8-Methyl-2-(2-methylphenyl)quinolin-3-yl]methyl}-3H-purin-6-amine

The title compound was prepared in a similar manner to Example 100, using Intermediate 61, and was obtained as a white solid (49 mg, 43%) after purification by preparative HPLC (Method 2). $\delta_H$ (DMSO-$d_6$) 8.45 (s, 1H), 8.00 (s, 1H), 7.70 (d, J 8.1 Hz, 1H), 7.58 (d, J 8 Hz, 1H), 7.25-7.50 (m, 5H), 7.10 (s, 1H), 5.54 (s, 2H), 2.74 (s, 3H), 2.01 (s, 3H). LCMS (ES+) 381.14 (M+H)+, RT 3.11 minutes (Method 4).

Example 103

3-{[2-(2-Methylphenyl)quinolin-3-yl]methyl}-3H-purin-6-amine

A mixture of Intermediate 9 (82 mg, 0.26 mmol) and adenine (70 mg, 0.52 mmol) in DMF (3 mL) was sonicated for 30 minutes at 40° C. then stirred at 80° C. for 1 h. Purification by preparative HPLC (Method 2) gave the title compound as a white solid (40 mg, 42%). $\delta_H$ (DMSO-$d_6$) 8.00 (s, 1H), 7.70-7.85 (m, 4H), 7.59-7.61 (m, 2H), 7.40-7.48 (m, 2H), 7.15-7.25 (m, 4H), 5.26 (s, 2H), 1.79 (s, 3H). LCMS (ES+) 367.1 (M+H)$^+$, RT 2.41 minutes (Method 4).

Example 104

4-(8-Methoxy-2-phenylquinolin-3-ylmethoxy)-6-methyl-1,3,5-triazin-2-ylamine

To a solution of Intermediate 97 (90 mg, 0.34 mmol) in dry 1,4-dioxane (10 mL) under nitrogen was added NaH (34 mg, 0.85 mmol, 60% dispersion in mineral oil). After stirring at r.t. for 5 minutes, addition of 2-amino-4-chloro-6-methyl-1,3,5-triazine (54 mg, 0.37 mmol) took place. The reaction mixture was heated at 80° C. for 2 h. The mixture was allowed to cool to r.t., water (10 mL) was added and the mixture was extracted with EtOAc (100 mL). The organic layer was separated, dried (MgSO$_4$), filtered and concentrated in vacuo. Purification by column chromatography (SiO$_2$, 60-80% EtOAc in Petrol 40-60) afforded the title compound (60 mg, 47%) as a white solid. $\delta_H$ (CDCl$_3$) 8.41 (s, 1H), 7.67 (dd, J 8.0, 1.6 Hz, 2H), 7.41-7.50 (m, 5H), 7.07 (dd, J 7.6, 1.2 Hz, 1H), 5.51 (s, 2H), 5.23 (br s, 2H), 4.07 (s, 3H), 2.38 (s, 3H). LCMS (ES+) 374 (M+H)$^+$, RT 2.62 minutes (Method 6).

Example 105

4-(8-Chloro-2-phenylquinolin-3-ylmethoxy)-6-methyl-1,3,5-triazin-2-ylamine

The title compound was prepared in a similar manner to Example 104, using Intermediate 98, and was obtained as a white solid (87 mg, 78%) after purification by column chromatography (SiO$_2$, 80% EtOAc in Petrol 40-60). $\delta_H$ (CDCl$_3$) 8.47 (s, 1H), 7.84 (dd, J 7.6, 1.2 Hz, 1H), 7.74-7.79 (m, 3H), 7.45-7.55 (m, 3H), 5.57 (s, 2H), 5.25 (br s, 2H), 2.38 (s, 3H). LCMS (ES+) 378, 380 (M+H)$^+$, RT 3.43 minutes (Method 6).

Example 106

3-(4-Amino-6-methyl-1,3,5-triazin-2-yloxymethyl)-2-phenylquinoline-8-carbonitrile The title compound was prepared in a similar manner to Example 104, using Intermediate 106, and was obtained as a white solid (37 mg, 65%) after purification by column chromatography (SiO$_2$, 0-1% MeOH in EtOAc). $\delta_H$ (CDCl$_3$) 8.54 (s, 1H), 8.14 (dd, J 7.2, 1.6 Hz, 1H), 8.09 (dd, J 8.4, 1.2 Hz, 1H), 7.77-7.79 (m, 2H), 7.61 (dd, J 8.0, 7.2 Hz, 1H), 5.61 (s, 2H), 5.22 (br s, 2H), 2.39 (s, 3H). LCMS (ES+) 369 (M+H)$^+$, RT 3.09 minutes (Method 6).

Example 107

4-{[8-Methyl-2-(1-methyl-1H-pyrazol-4-yl)quinolin-3-yl]methoxy}-1,3,5-triazin-2-amine To a solution of (2-chloro-8-methylquinolin-3-yl)methanol (150 mg, 0.72 mmol) in 1,4-dioxane/water (4 mL/1 mL) was added 1-methyl-4-(4,4,5,5-tetramethyl-[1,3,2]-dioxaborolan-2-yl)-1H-pyrazole (181 mg, 0.87 mmol), K$_2$CO$_3$ (199 mg, 1.44 mmol) and Pd(PPh$_3$)$_4$ (83 mg, 0.07 mmol). The mixture was degassed and heated in a microwave at 150° C. for 1 h. The solvent was removed in vacuo and the residue dissolved in DCM (50 mL) and washed with water (2×10 mL). The organic layer was separated, dried (MgSO$_4$), filtered and the solvent removed in vacuo. Purification by column chromatography (SiO$_2$, 0-20% EtOAc in Et$_2$O) afforded the desired intermediate. This was dissolved in 1,4-dioxane (6 mL) under nitrogen and to it was added NaH (55 mg, 1.36 mmol, 60% in mineral oil). The solution was stirred at r.t for 5 minutes before 4-chloro-1,3,5-triazin-2-amine (106 mg, 0.82 mmol) was added and the mixture heated at 80° C. for 48 h. The mixture was poured into EtOAc (50 mL) and washed with water (3×10 mL). Purification by column chromatography (SiO$_2$, 2-6% MeOH in DCM) yielded the title compound (38 mg, 16%) as a white solid. $\delta_H$ (DMSO-d$_6$) 8.42 (s, 1H), 8.37 (s, 1H), 8.34 (s, 1H), 8.04 (s, 1H), 7.83 (d, J 8.1 Hz, 1H), 7.57-7.69 (m, 3H), 7.47 (t, J 7.6 Hz, 1H), 5.69 (s, 2H), 3.99 (s, 3H), 2.78 (s, 3H). LCMS (ES+) 348 (M+H)$^+$, RT 2.75 minutes (Method 7).

Example 108

4-Methyl-6-{[8-methyl-2-(1-methyl-1H-pyrazol-4-yl)quinolin-3-yl]methoxy}-1,3,5-triazin-2-amine The title compound was prepared in a similar manner to Example 107, using (2-chloro-8-methylquinolin-3-yl)methanol, and was obtained as a white solid (35 mg, 14%) after purification by column chromatography (SiO$_2$, 2-8% MeOH in DCM). $\delta_H$ (DMSO-d$_6$) 8.43 (s, 1H), 8.33 (s, 1H), 8.05 (s, 1H), 7.83 (d, J 8.1 Hz, 1H), 7.64 (d, J 7.0 Hz, 1H), 7.42-7.52 (m, 3H), 5.67 (s, 2H), 3.99 (s, 3H), 2.78 (s, 3H), 2.28 (s, 3H). LCMS (ES+) 362 (M+H)$^+$, RT 3.82 minutes (Method 7).

Example 109

4-{[2-(3-Methoxyphenyl)-8-methylquinolin-3-yl]methoxy}-1,3,5-triazin-2-amine

To a solution of Intermediate 107 (150 mg, 0.53 mmol) in 1,4-dioxane (6 mL) under nitrogen was added NaH (54 mg, 1.34 mmol, 60% in mineral oil). After stirring at r.t. for 5 minutes addition of 4-chloro-1,3,5-triazin-2-amine (104 mg, 0.80 mmol) took place and the reaction was heated at 80° C. for 48 h. The mixture was poured into EtOAc (50 mL) and washed with water (3×10 mL). The organic layer was separated, dried (MgSO$_4$), filtered and the solvent removed in vacuo. Purification by column chromatography (SiO$_2$, 50-100% EtOAc in Petrol 40-60) yielded the title compound (52 mg, 26%) as a white solid. $\delta_H$ (CDCl$_3$) 8.39 (s, 1H), 8.37 (s, 1H), 7.69 (d, J 8.1 Hz, 1H), 7.58 (d, J 7.0 Hz, 1H), 7.38-7.48 (m, 2H), 7.26-7.29 (m, 2H), 7.02 (d, J 8.3 Hz, 1H), 5.56 (s, 2H), 5.37 (br s, 2H), 3.87 (s, 3H), 2.82 (s, 3H). LCMS (ES+) 374 (M+H)$^+$, RT 3.53 minutes (Method 7).

Example 110

4-{[2-(3-Methoxyphenyl)-8-methylquinolin-3-yl]methoxy}-6-methyl-1,3,5-triazin-2-amine The title compound was prepared in a similar manner to Example 109, using Intermediate 107, and was obtained as a white solid (27 mg, 13%) after column chromatography (SiO$_2$, 50-100% EtOAc in Petrol 40-60). $\delta_H$ (CDCl$_3$) 8.40 (s, 1H), 7.69 (d, J 8.1 Hz. 1H), 7.57 (d, J 7.0 Hz, 1H), 7.39-7.46 (m, 2H), 7.23-7.33 (m, 2H), 7.02 (dd, J 8.3, 2.5 Hz, 1H), 5.55 (s, 2H), 5.23 (br s, 2H), 3.87 (s, 3H), 2.82 (s, 3H), 2.38 (s, 3H). LCMS (ES+) 388 (M+H)$^+$, RT 3.43 minutes (Method 7).

Example 111

4-Methyl-6-{[8-methyl-2-(thien-3-yl)quinolin-3-yl]methoxy}-1,3,5-triazin-2-amine The title compound was prepared in a similar manner to Example 109, using Intermediate 24, and was obtained as a white solid (35 mg, 22%) after column chromatography (SiO$_2$, 50-100% EtOAc in Petrol 40-60). $\delta_H$ (CDCl$_3$) 8.40 (s, 1H), 7.82 (dd, J 3.0, 1.4 Hz, 1H), 7.66-7.74 (m, 2H), 7.56 (d, J 7.0 Hz, 1H), 7.39-7.47 (m, 2H), 5.66 (s, 2H), 5.35 (br s, 2H), 2.83 (s, 3H), 2.42 (s, 3H). LCMS (ES+) 364 (M+H)$^+$, RT 3.59 minutes (Method 6).

Example 112

(S)-4-Methyl-6-{1-[8-methyl-2-(1-methyl-1H-pyrazol-4-yl)quinolin-3-yl]ethoxy}-1,3,5-triazin-2-amine To a solution/suspension of Intermediate 101 (150 mg, 0.68 mmol) in DME/MeOH (4 mL/1 mL) was added 1-methylpyrazole-4-boronic acid (155 mg, 0.74 mmol) and CsF (103 mg, 0.68 mmol). The mixture was degassed before the addition of Pd(PPh$_3$)$_4$ (79 mg, 0.068 mmol) took place. Degassing was repeated and the mixture was heated at 150° C. in a microwave for 1 h. The solvents were removed in vacuo. The residue was dissolved in DCM (100 mL) and washed with water (2×50 mL). The organic layer was separated, dried (MgSO$_4$), filtered and the solvent removed in vacuo. Purification by column chromatography (SiO$_2$, 0-20% EtOAc in DCM) afforded the desired intermediate as pale yellow film. This was dissolved in dry 1,4-dioxane (10 mL) under nitrogen and to it was added NaH (68 mg, 1.70 mmol, 60% dispersion in mineral oil). After stirring at r.t. for 5 minutes, addition of 2-amino-4-chloro-6-methyltriazine (108 mg, 0.75 mmol) took place. The reaction mixture was heated at 80° C. for 18 h and then allowed to cool to r.t. Water (10 mL) was added and the mixture was extracted with EtOAc (100 mL). The organic layer was separated, dried (MgSO$_4$), filtered and concentrated in vacuo. Purification by column chromatography (SiO$_2$, 50-100% EtOAc in Petrol 40-60) gave a clear film, which upon lyophilisation afforded the title compound (32 mg, 25%) as a white solid. $\delta_H$ (CDCl$_3$) 8.36 (s, 1H), 8.14 (s, 1H), 8.02 (s, 1H), 7.63 (d, J 8.2 Hz, 1H), 7.56-7.48 (m, 1H), 7.36 (t, J 7.6 Hz, 1H), 6.73 (q, J 6.5 Hz, 1H), 4.04 (s, 3H), 2.80 (s, 3H), 2.32 (s, 3H), 1.69 (d, J 6.5 Hz, 3H). LCMS (ES+) 376 (M+H)$^+$, RT 2.82 minutes (Method 6).

Example 113

(S)-4-Methyl-6-[1-(8-methyl-2-phenylquinolin-3-yl)ethoxy]-1,3,5-triazine-2-amine The title compound was prepared in a similar manner to Example 109, using Intermediate 108, and was obtained as a white solid (34 mg, 27%) after column chromatography (SiO$_2$, 80% EtOAc in Petrol 40-60). $\delta_H$ (CDCl$_3$) 8.40 (s, 1H), 7.78 (d, J=8.4 Hz, 2H), 7.67 (d, J 8.4 Hz, 1H), 7.50-7.58 (m, 3H), 7.38-7.46 (m, 2H), 6.45 (q, J 6.8 Hz, 1H), 5.05 (br s, 2H), 2.79 (s, 3H), 2.27 (s, 3H), 1.65 (d, J 6.8 Hz, 3H). LCMS (ES+) 372 (M+H)$^+$, RT 3.72 minutes (Method 6).

Example 114

(S)-4-Methyl-6-{1-[8-methyl-2-(pyridin-3-yl)quinolin-3-yl]ethoxy}-1,3,5-triazin-2-amine The title compound was prepared in a similar manner to Example 109, using Intermediate 109, and was obtained as a white solid (26 mg, 24%) after column chromatography (SiO$_2$, 80% EtOAc in Petrol 40-60). $\delta_H$ (CDCl$_3$) 9.06 (s, 1H), 8.75 (d, J=6.4 Hz, 1H), 8.45 (s, 1H), 8.06 (d, J 8.2 Hz, 1H), 7.70 (d, J 8.2 Hz, 1H), 7.58 (d, J 6.4 Hz, 1H), 7.51 (d, J 6.4 Hz, 1H), 7.48 (t, J 8.2 Hz, 1H), 6.35 (q, J 6.4 Hz, 1H), 5.30 (br s, 2H), 2.79 (s, 3H), 2.28 (s, 3H), 1.69 (d, J 6.4 Hz, 3H). LCMS (ES+) 373 (M+H)$^+$, RT 2.63 minutes (Method 6).

Example 115

(S)-4-Methyl-6-{1-[2-(3,5-dimethylisoxazol-4-yl)-8-methylquinolin-3-yl]ethoxy}-1,3,5-triazin-2-amine To a solution/suspension of Intermediate 101 (250 mg, 1.13 mmol) in 1,4-dioxane/water (4 mL/0.8 mL) was added 3,5-dimethylisoxazole-4-boronic acid (159 mg, 1.13 mmol), K$_2$CO$_3$ (312 mg, 2.26 mmol) and Pd(PPh$_3$)$_4$ (65 mg, 0.056 mmol). The mixture was heated in a microwave at 160° C. for 90 minutes. Water (15 mL) was added and the mixture was extracted with DCM (3×20 mL). The organic layers were combined, dried (MgSO$_4$), filtered and concentrated in vacuo to give a yellow oil. Dioxane, water, boronic acid, K$_2$CO$_3$ and Pd(PPh$_3$)$_4$ were added to the oil in the same quantities as above. The mixture was degassed for 10 minutes and heated in a microwave at 160° C. for 90 minutes. Work-up was repeated using the procedure described above to yield an orange oil. Purification by column chromatography (SiO$_2$, 0-100% Et$_2$O in Petrol 40-60) afforded the desired intermediate as a yellow oil. To a solution of this oil in 1,4-dioxane (6 ml) under nitrogen was added NaH (13 mg, 0.316 mmol, 60% in mineral oil) and the mixture stirred at r.t. for 5 minutes. 2-Amino-4-chloro-6-methyl-1,3,5-triazine (46 mg, 0.316 mmol) was added and the reaction was heated at 80° C. for 18 h. Saturated NaHCO$_3$ solution (20 mL) was added and the mixture was extracted with DCM (3×20 mL). The organic layers were combined, passed through a hydrophobic frit and concentrated in vacuo to give a yellow solid. Purification by column chromatography (SiO$_2$, 0-100% EtOAc in cyclohexane) gave a clear film, which upon lyophilisation afforded the title compound (19.5 mg, 4%) as a white solid. $\delta_H$ (CDCl$_3$) 8.45 (s, 1H), 7.71 (d, J 8.18 Hz, 1H), 7.58 (d, J 6.96 Hz, 1H), 7.46 (t, J 7.60 Hz, 1H), 6.31 (q, J 6.5 Hz, 1H), 5.20 (br s, 2H), 2.77 (s, 3H), 2.44 (s, 3H), 2.33 (s, 3H), 2.25 (s, 3H), 1.51-1.64 (m, 3H). LCMS (ES+) 391 (M+H)$^+$, RT 3.28 minutes (Method 6).

Example 116

(S)-4-Methyl-6-{1-[8-methyl-2-(2-methylphenyl)quinolin-3-yl]ethoxy}-1,3,5-triazin-2-amine The title compound was prepared in a similar manner to Example 115, using Intermediate 101, and was obtained as a white solid (7.9 mg, 23%) after purification by column chromatography (SiO$_2$, 10-50% EtOAc in cyclohexane). $\delta_H$ (DMSO-d$_6$, 105° C.) 8.49 (s, 1H), 7.90 (d, J 8.2 Hz, 1H), 7.65 (d, J 7.0 Hz, 1H), 7.53 (t, J 7.6 Hz, 1H), 7.30-7.43 (m, 4H), 6.76 (br s, 2H), 6.20 (q, J 6.5 Hz, 1H), 2.72 (s, 3H), 2.20 (s, 3H), 2.14 (s, 3H), 1.51 (d, J 6.5 Hz, 3H). LCMS (ES+) 386 (M+H)$^+$, RT 3.76 minutes (Method 6).

Example 117

(S)—N$^2$-(4-Methoxybenzyl)-6-methyl-N$^4$-[1-(8-methyl-2-phenylquinolin-3-yl)ethyl]-1,3,5-triazine-2,4-diamine To a solution/suspension of Intermediate 103 (100 mg, 0.31 mmol) in DME (1 mL) was added phenylboronic acid (42 mg, 0.34 mmol), Na$_2$CO$_3$ solution (0.46 mL, 0.93 mmol, 2M) and Pd(PPh$_3$)$_4$ (36 mg, 0.031 mmol). The mixture was degassed for 10 minutes and heated in a microwave at 120° C. for 1 h. The reaction was allowed to cool to r.t., treated with conc. HCl (2 mL) and stirred for 30 minutes. Water (10 mL) was added and the mixture was washed with DCM (3×10 mL). The aqueous layer was basified by the addition of 15% NaOH and extracted with DCM (3×40 mL). The organic layers were combined, dried (MgSO$_4$), filtered and concentrated in vacuo. The residue was dissolved in n-BuOH (2.5 mL) and this solution was treated with DIPEA (0.28 mL, 1.55 mmol) and Intermediate 110 (123 mg, 0.47 mmol). The mixture was heated in a microwave at 140° C. for 90 minutes. The solvents were removed in vacuo and the residue was purified by preparative HPLC (Method 8) to afford the title compound (46 mg, 30%) as a white solid. $\delta_H$ (CDCl$_3$) 8.18 (s, 1H), 7.35-7.94 (m, 8H), 7.15-7.27 (m, 1H), 6.80-6.95 (m, 2H), 6.52-6.62 (m, 1H), 5.58-5.69 (m, 1H), 4.15-4.54 (m, 2H), 3.66-3.84 (m, 3H), 3.48 (s, 2H), 2.78 (s, 3H), 2.22 (br s, 3H), 1.32-1.42 (s, 3H). LCMS (ES+) 491 (M+H)$^+$, RT 2.92 mins (Method 6).

Example 118

(S)-6-Methyl-N$^2$-{1-[8-methyl-2-(thien-3-yl)quinolin-3-yl]ethyl}-1,3,5-triazine-2,4-diamine To a solution/suspension of Intermediate 105 (120 mg, 0.37 mmol) in DME/MeOH (2.2 mL/0.5 mL) was added 3-thiopheneboronic acid (53 mg, 0.41 mmol) and CsF (62 mg, 0.41 mmol). The mixture was degassed before the addition of Pd(PPh$_3$)$_4$ (43 mg, 0.037 mmol) took place. Degassing was repeated and the mixture was heated in a microwave at 150° C. for 1 h. The solvents were removed in vacuo and the residue was dissolved in DCM (100 mL) and washed with water (2×50 mL). The organic layer was separated, dried (MgSO$_4$), filtered and the solvent removed in vacuo. Purification by column chromatography (SiO$_2$, 0-20% EtOAc in Petrol 40-60) afforded the desired intermediate as a pale yellow solid. To a solution of this solid in DCM (2 mL), TFA (2 mL) was added dropwise. The mixture was stirred at r.t. for 2 h. The solvents were removed in vacuo and the residue was dissolved in n-BuOH (4 mL). To this solution, DIPEA (0.33 mL, 1.85 mmol) and 2-amino-4-chloro-6-methyltriazine (80 mg, 0.56 mmol) were added and the mixture was heated in a microwave at 150° C. for 1 h. The solvents were removed in vacuo and the residue was purified by column chromatography (SiO$_2$, Et$_2$O) to give a clear film. This was dissolved in DCM (100 mL) and washed with water (3×50 mL). The organic layer was separated, dried (MgSO$_4$), filtered and the solvent removed in vacuo to give a clear film, which upon lyophilisation afforded the title compound (45 mg, 32%) as a white solid. $\delta_H$(DMSO-d$_6$, 85° C.) 8.41 (s, 1H), 7.96 (d, J=2.4 Hz, 1H), 7.72 (d, J 8.2 Hz, 1H), 7.62-7.66 (m, 2H), 7.56 (d, J 7.1 Hz, 1H), 7.44 (t, J 7.6 Hz, 1H), 7.34 (d, J 7.9 Hz, 1H), 6.09 (s, 2H), 5.64-5.70 (m, 1H), 2.73 (s, 3H), 2.08 (s, 3H), 1.37 (d, J 6.9 Hz, 3H). LCMS (ES+) 377 (M+H)$^+$, RT 2.89 minutes (Method 6).

Example 119

(S)—N$^2$-{1-[2-(3,5-Dimethylisoxazol-4-yl)-8-methylquinolin-3-yl]ethyl}-6-methyl-1,3,5-triazine-2,4-diamine The title compound was prepared in a similar manner to Example 118, using Intermediate 105, and was obtained as an off-white solid (35 mg, 24%) after purification by column chromatography (SiO$_2$, Et$_2$O). $\delta_H$ (CDCl$_3$) 8.15 (s, 1H), 7.66 (d, J 8.15 Hz, 1H), 7.56 (d, J 7.00 Hz, 1H), 7.45 (t, J 7.57 Hz, 1H), 5.20-5.55 (m, 2H), 4.85-5.15 (m, 2H), 2.76 (s, 3H), 2.46 (s, 3H), 2.10-2.35 (m, 6H), 1.47-1.21 (m, 3H). LCMS (ES+) 390 (M+H)$^+$, RT 2.72 minutes (Method 6).

Example 120

(S)-6-Methyl-N$^2$-{1-[8-methyl-2-(1-methyl-1H-pyrazol-4-yl)quinolin-3-yl]ethyl}-1,3,5-triazine-2,4-diamine To a solution/suspension of Intermediate 103 (150 mg, 0.46 mmol) in 1,4-dioxane/water (3.8 mL/0.75 mL) was added 1-methyl-4-(4,4,5,5-tetramethyl-[1,3,2]-dioxaborolan-2-yl)-1H-pyrazole (115 mg, 0.55 mmol) and K$_2$CO$_3$ (128 mg, 0.92 mmol). The mixture was degassed before the addition of Pd(PPh$_3$)$_4$ (53 mg, 0.046 mmol) took place. Degassing was repeated and the mixture was heated in a microwave at 150° C. for 1 h. To this solution was added conc. HCl (4 mL) and the reaction was stirred at r.t. for 2 h. The mixture was washed with DCM (3×10 mL) and the aqueous layer was basified with 15% NaOH solution and extracted with DCM (2×50 mL). The organic layer was separated, dried (MgSO$_4$), filtered and the solvent removed in vacuo to give the desired intermediate as a dark oil. To a solution of this oil in n-BuOH (4 mL) was added DIPEA (0.41 mL, 2.3 mmol) and 2-amino-4-chloro-6-methyltriazine (100 mg, 0.69 mmol) and the mixture was heated in a microwave at 150° C. for 1 h. The solvents were removed in vacuo and the residue was purified by column chromatography (SiO$_2$, 50-100% EtOAc in Petrol 40-60) to give the title compound (69 mg, 44%) as an off-white solid. $\delta_H$(DMSO-d$_6$, 105° C.) 8.36 (s, 1H), 8.23 (s, 1H), 8.03 (s, 1H), 7.67 (d, J 8.1 Hz, 1H), 7.53 (d, J 7.0 Hz, 1H), 7.39 (t, J 7.5 Hz, 1H), 7.20 (s, 1H), 6.04 (s, 2H), 5.73-5.79 (m, 1H), 3.97 (s, 3H), 2.75 (s, 3H), 2.46-2.54 (m, 3H), 2.10 (s, 3H), 1.47 (d, J 6.8 Hz, 3H). LCMS (ES+) 375 (M+H)$^+$, RT 2.52 minutes (Method 6).

Example 121

(S)-6-Methyl-N$^2$-[1-(8-methyl-2-phenylquinolin-3-yl)ethyl]-1,3,5-triazine-2,4-diamine The title compound was prepared in a similar manner to Example 120, using Intermediate 103, and was obtained as an off-white solid (75 mg, 44%) after purification by column chromatography (SiO$_2$, 50-100% EtOAc in Petrol 40-60). $\delta_H$ (CDCl$_3$) 8.14 (s, 1H), 7.72-7.89 (m, 2H), 7.62 (d, J 8.18 Hz, 1H), 7.36-7.55 (m, 5H), 5.25-5.75 (m, 2H), 4.70-5.10 (m, 2H), 2.79 (s, 3H), 2.22 (s, 3H), 1.39 (s, 3H). LCMS (ES+) 371 (M+H)$^+$, RT 2.90 minutes (Method 6).

Example 122

(5)-6-Methyl-N$^2$-{1-[8-methyl-2-(2-methylphenyl)quinolin-3-yl]ethyl}-1,3,5-triazine-2,4-diamine To a solution/suspension of Intermediate 105 (120 mg, 0.37 mmol) in 1,4-dioxane/water (1 mL/0.2 mL) was added 2-tolueneboronic acid (50 mg, 0.37 mmol), K$_2$CO$_3$ (103 mg, 0.75 mmol) and Pd(PPh$_3$)$_4$ (22 mg, 0.019 mmol). The mixture was degassed for 10 minutes and then heated in a microwave at 160° C. for 90 minutes. Water (20 mL) was added and the mixture was extracted with DCM (3×40 mL) and passed through a hydrophobic fit. The solvent was removed in vacuo and the residue purified by column chromatography (SiO$_2$, 0-100% EtOAc in cyclohexane) to afford the desired intermediate as a white solid. To a solution of this solid in DCM (3 mL) was added TFA (1 mL), and the mixture was stirred at r.t. for 3 h. The solvents were removed in vacuo, saturated Na$_2$CO$_3$ solution (20 mL) was added and the mixture was extracted with DCM (3×30 mL) and passed through a hydrophobic frit. The organic layer was concentrated in vacuo and the residue was dissolved in n-BuOH (2 mL). To this solution, DIPEA (0.101 mL, 0.58 mmol) and 2-amino-4-chloro-6-methyltriazine (41 mg, 0.28 mmol) were added and the mixture was heated in a microwave at 140° C. for 1 h. The solvent was removed in vacuo and the residue was purified by column chromatography (SiO$_2$, 30-100% EtOAc in cyclohexane) to give a clear film, which after lyophilisation afforded the title compound (35 mg, 24%) as a white solid. $\delta_H$ (CDCl$_3$) 8.15 (s, 1H), 7.65 (d, J 8.2 Hz, 1H), 7.52 (d, J 7.0 Hz, 1H), 7.41 (t, J 7.6 Hz, 1H), 7.19-7.40 (m, 4H), 4.77-5.53 (m, 4H), 2.75 (s, 3H), 2.13-2.33 (m, 6H), 1.77 (br s, 3H). LCMS (ES+) 385 (M+H)$^+$, RT 2.43 minutes (Method 6).

Example 123

(S)—N$^4$-{1-[8-Methyl-2-(pyridin-3-yl)quinolin-3-yl]ethyl}-1H-pyrazolo[3,4-d]pyrimidin-4-amine To a solution/suspension of Intermediate 103 (120 mg, 0.37 mmol) in 1,4-dioxane/water (3 mL/0.6 mL) was added 3-pyridineboronic acid (136 mg, 1.11 mmol), K$_2$CO$_3$ (255 mg, 1.85 mmol) and Pd(PPh$_3$)$_4$ (53 mg, 0.046 mmol). The mixture was degassed for 10 minutes and heated in a microwave at 150° C. for 1 h. The solution was filtered through cotton wool then 3-pyridineboronic acid (68 mg), K$_2$CO$_3$ (198 mg) and Pd(PPh$_3$)$_4$ (53 mg, 0.046 mmol) were added and the reaction was heated in a microwave at 150° C. for 1 h. The reaction was allowed to cool to r.t., treated with conc. HCl (2 mL) and stirred for 30 minutes. Water (10 mL) was added and the mixture was washed with DCM (2×20 mL). The aqueous layer was basified by the addition of solid K$_2$CO$_3$ and extracted with DCM (2×40 mL). The organic layers were combined, dried (MgSO$_4$), filtered and concentrated in vacuo. The residue was purified by column chromatography (SiO$_2$, 0-10% MeOH and 0-1% aq. ammonia in DCM) to afford a yellow oil (0.132 g). A portion of the oil (44 mg) was dissolved in n-BuOH (2 mL) and this solution was treated with DIPEA (0.090 mL, 0.50 mmol) and 4-chloro-1H-pyrazolo[3,4-d]pyrimidine (39 mg, 0.25 mmol). The mixture was heated in a microwave at 140° C. for 1 h. The solvents were removed in vacuo and the residue was purified by column chromatography (SiO$_2$, 0-10% MeOH and 0-1% aq. ammonia in DCM), followed by passing through a C18-SPE cartridge (eluting with 40% MeCN in water) and lyophilisation, to give the title compound (9.4 mg, 8%) as a white solid. $\delta_H$ (CDCl$_3$) 9.09 (s, 1H), 8.69 (d, J 4.8 Hz, 1H), 8.26 (s, 1H), 8.26 (s, 1H), 8.18 (d, J 7.7 Hz, 1H), 7.92 (s, 1H), 7.62 (d, J 8.1 Hz, 1H), 7.54 (t, J 7.0 Hz, 1H), 7.40-7.43 (m, 2H), 5.95-6.15 (s, 1H), 5.78 (br s, 1H), 2.78 (s, 3H), 1.59 (d, J 6.8 Hz, 3H). LCMS (ES+) 382 (M+H)$^+$, RT 2.20 minutes (Method 6).

Example 124

(S)—N$^2$-{1-[8-Methyl-2-(pyridin-3-yl)quinolin-3-yl]ethyl}-1,3,5-triazine-2,4-diamine The title compound was prepared in a similar manner to Example 123, using Intermediate 103, and was obtained as a white solid (5 mg, 4%) after purification by passing through a C18-SPE cartridge (eluting with 40% MeCN in water). $\delta_H$ (CDCl$_3$) 9.13 (s, 1H), 8.67 (s, 1H), 8.27 (s, 1H), 8.13 (d, J 7.90 Hz, 1H), 8.01 (s, 1H), 7.69 (d, J=8.21 Hz, 1H), 7.40-7.59 (m, 4H), 5.48 (d, J 7.58 Hz, 1H), 2.61-3.04 (m, 5H), 1.39 (d, J=6.8 Hz, 3H). LCMS (ES+) 357 (M+H)$^+$, RT 2.05 minutes (Method 6).

Example 125

(S)—N$^4$-{1-[2-(3,5-Dimethylisoxazol-4-yl)-8-methylquinolin-3-yl]ethyl}-1H-pyrazolo[3,4-d]pyrimidin-4-amine The title compound was prepared in a similar manner to Example 123, using Intermediate 103, and was obtained as a white solid (15 mg, 12%) after purification by column chromatography (SiO$_2$, EtOAc in Petrol 40-60). $\delta_H$ (CDCl$_3$) 11.87 (s, 1H), 8.31 (s, 1H), 8.19 (s, 1H), 8.02 (s, 1H), 7.64 (d, J 8.14 Hz, 1H), 7.56 (d, J 6.97 Hz, 1H), 7.44 (t, J 7.59 Hz, 1H), 5.50-5.70 (m, 2H), 2.77 (s, 3H), 2.50 (s, 3H), 2.29 (s, 3H), 1.40-1.70 (m, 3H). LCMS (ES+) 400 (M+H)$^+$, RT 2.69 minutes (Method 6).

Example 126

(S)—N$^2$-{1-[2-(3,5-Dimethylisoxazol-4-yl)-8-methylquinolin-3-yl]ethyl}-1,3,5-triazine-2,4-diamine The title compound was prepared in a similar manner to Example 123, using Intermediate 103, and was obtained as a white solid (22 mg, 19%) after purification by column chromatography (SiO$_2$, 50-100% EtOAc in Petrol 40-60). $\delta_H$ (DMSO-d$_6$) 8.42 (s, 1H), 7.69-8.05 (m, 3H), 7.64 (d, J 6.9 Hz, 1H), 7.54 (t, J 7.6 Hz, 1H), 5.12-5.25 (m, 1H), 2.70 (s, 3H), 2.45 (br s, 3H), 2.17 (br s, 3H), 1.30-1.40 (m, 3H). LCMS (ES+) 376 (M+H)$^+$, RT 2.42 minutes (Method 6).

The invention claimed is:

1. A compound of formula (IA) or an N-oxide thereof, or a pharmaceutically acceptable salt thereof:

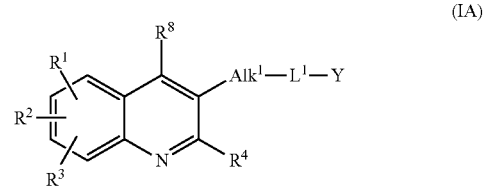

(IA)

wherein
Alk$^1$ represents a straight or branched C$_{1-3}$ alkylene chain;
L$^1$ represents NR$^9$;
Y represents pyrrolyl, pyridin-2-yl, pyridin-3-yl, indolyl, isoquinolinyl, imidazolyl, pyrazolyl, triazolyl, pyridazinyl, pyrimidin-5-yl, pyrazinyl, triazinyl, indazolyl, furopyridinyl, benzoxazolyl, benzothiazolyl, cinnolinyl, phthalazinyl, quinazolinyl, purin-1-yl, purin-2-yl, purin-3-yl, purin-7-yl, purin-8-yl, pyrazolo[3,4-d]pyrimidin-4-yl, triazolopyrimidinyl, naphthyridinyl, pteridinyl or pyridopyrimidin-4-yl, any of which groups may be optionally substituted by one, two or three substituents independently selected from halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, C$_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, oxo and arylamino;

$R^1$, $R^2$ and $R^3$ independently represent hydrogen, halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;

$R^4$ represents a group of formula (a):

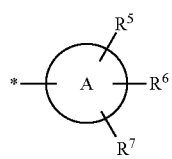

(a)

in which *—— represents the bond attaching the ring A to the rest of the molecule;

A represents a monocyclic aryl or heteroaryl group;

$R^5$, $R^6$ and $R^7$ independently represent hydrogen, halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylamino-sulfonyl, $C_{3-7}$ cycloalkyl or $C_{3-6}$ heterocycloalkyl, or optionally substituted monocyclic aryl or heteroaryl;

$R^8$ represents hydrogen, halogen, $C_{1-6}$ alkyl or $C_{1-6}$ alkoxy; and $R^9$ represents hydrogen or $C_{1-6}$ alkyl.

2. A compound as claimed in claim 1, wherein Y represents isoquinolinyl, triazinyl, purin-3-yl, purin-7-yl, or pyridopyrimidin-4-yl, any of which groups may be optionally substituted by one, two or three substituents.

3. A compound as claimed in claim 1 wherein Y represents optionally substituted triazinyl.

4. A compound as claimed in claim 1 or an N-oxide thereof, or a pharmaceutically acceptable salt thereof, wherein
Y represents pyridopyrimidin-4-yl, which may be optionally substituted by one, two or three substituents.

5. A compound as claimed in claim 1 wherein $R^8$ represents hydrogen.

6. A compound as claimed in claim 1 wherein $R^9$ represents hydrogen.

7. A compound as claimed in claim 1 wherein $Alk^1$ represents —$CH_2$—, —$CH(CH_3)$— or —$CH(CH_2CH_3)$—.

8. A compound as claimed in claim 7 wherein $Alk^1$ represents —$CH(CH_3)$—.

9. A compound as claimed in claim 1 wherein the moiety A represents phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl or triazinyl.

10. A compound as claimed in claim 9 wherein the moiety A represents phenyl.

11. A compound as claimed in claim 9 wherein the moiety A represents pyridinyl.

12. A pharmaceutical composition comprising a compound of formula (IA) as claimed in claim 1 or an N-oxide thereof, or a pharmaceutically acceptable salt thereof, in association with a pharmaceutically acceptable carrier.

* * * * *